(12) United States Patent
Chang et al.

(10) Patent No.: US 9,278,982 B2
(45) Date of Patent: Mar. 8, 2016

(54) TARGETING HUMAN THYMIDYLATE KINASE INDUCES DNA REPAIR TOXICITY IN MALIGNANT TUMOR CELLS

(75) Inventors: Zee Fen Chang, Taipei (TW); Jim-Min Fang, Taipei (TW); Chun-Mei Hu, New Taipei (TW); Ming-Tyng Yeh, Taipei (TW)

(73) Assignees: NATIONAL YANG-MING UNIVERSITY, Taipei (TW); NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 13/990,398

(22) PCT Filed: Nov. 29, 2011

(86) PCT No.: PCT/CN2011/083103
§ 371 (c)(1),
(2), (4) Date: May 29, 2013

(87) PCT Pub. No.: WO2012/072019
PCT Pub. Date: Jun. 7, 2012

(65) Prior Publication Data
US 2013/0252953 A1    Sep. 26, 2013

Related U.S. Application Data

(60) Provisional application No. 61/417,648, filed on Nov. 29, 2010.

(51) Int. Cl.
| | | |
|---|---|---|
| C07D 513/04 | (2006.01) | |
| C07D 275/04 | (2006.01) | |
| C07D 275/06 | (2006.01) | |
| A61K 31/403 | (2006.01) | |
| A61K 31/425 | (2006.01) | |
| A61K 31/704 | (2006.01) | |
| A61K 45/06 | (2006.01) | |

(52) U.S. Cl.
CPC ............ *C07D 513/04* (2013.01); *A61K 31/403* (2013.01); *A61K 31/425* (2013.01); *A61K 31/704* (2013.01); *A61K 45/06* (2013.01); *C07D 275/04* (2013.01); *C07D 275/06* (2013.01)

(58) Field of Classification Search
None
See application file for complete search history.

(56) References Cited

U.S. PATENT DOCUMENTS

| 3,965,107 A | 6/1976 | Rainey et al. |
| 5,776,925 A | 7/1998 | Young et al. |
| 2005/0049207 A1 | 3/2005 | Kaufmann |

FOREIGN PATENT DOCUMENTS

| CN | 1185737 A | 6/1998 |
| CN | 1775025 A | 5/2006 |
| CN | 101427835 A | 5/2009 |
| JP | 2007210938 A | 8/2007 |
| KR | 20040014007 A | 2/2004 |
| PL | 314025 A1 | 10/1997 |
| PL | 317859 A1 | 7/1998 |
| PL | 180728 B1 | 3/2001 |
| PL | 185588 B1 | 6/2003 |

OTHER PUBLICATIONS

Haouz et al. disclose in J. Biol. Chem. 278, 4963-4971 (2003).*
Speziale et al. In Journal of the American Chemical Society 78, 5580-5584 (1056).*
"Aurora Fine Chemicals", RN 902589-96-2, Database Registry Chemical Abstracts Service, Columbus, Ohio, Accession No. RN 902589-96-2, Entered STN: Aug. 18, 2006.*
Ito et al. In Cancer Science 94(1), 3-8 (2003).*
"Aurora Fine Chemicals", RN 902872-75-7, Database Registry Chemical Abstracts Service, Columbus, Ohio, Accession No. RN 902872-75-7, Entered STN: Aug. 21, 2006.*
K. Hirai et al., "Reactivity of Some Benzothiazepine Derivatives," Annu. Rep. Sankyo Res. Lab. 44, 141-150 (1992).
C.M. Hu et al., "Synthetic Lethality by Lentiviral Short Hairpin RNA Silencing of Thymidylate Kinase and Doxorubicin in Colon Cancer Cells Regardless of the *p53* Status," Cancer Res 2008; 68: 2831-2840, publ. online Apr. 15, 2008.

\* cited by examiner

*Primary Examiner* — Dennis Heyer
(74) *Attorney, Agent, or Firm* — Muncy, Geissler, Olds & Lowe, P.C.

(57) ABSTRACT

The present invention relates to novel TMPK inhibitor compositions and their methods of use. In particular, it relates to novel TMPK inhibitor compositions and therapeutics that lead to dUTP-mediated DNA repair in tumor cells and acts as a novel chemosensitizer, which are useful in methods for treating or preventing cancers.

3 Claims, 22 Drawing Sheets

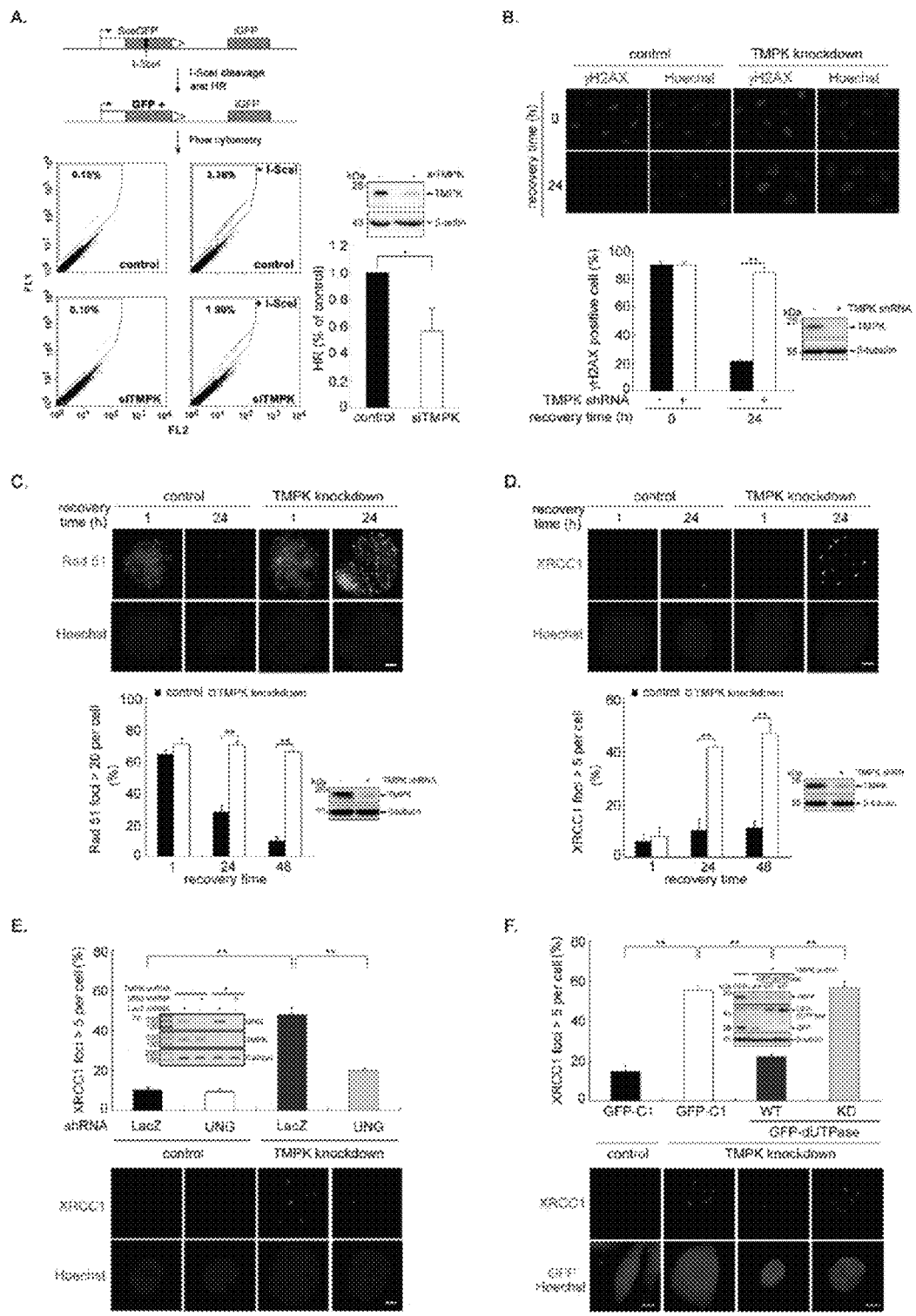
Figure 2. TMPK Knockdown causes DSB repair with dUTP incorporation

Figure 3. Effect of TMPK knockdown on viability in response to DNA damage
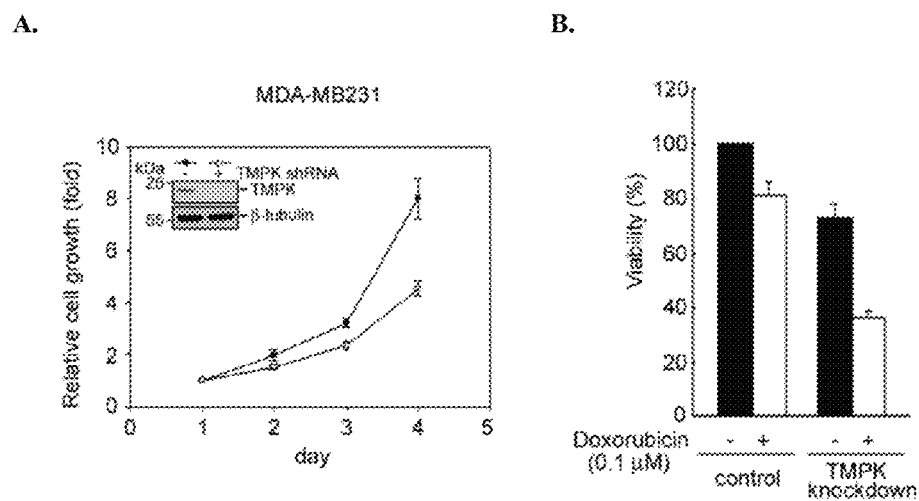

Figure 4. Measurement of recombinant human dUTPase activity
A.
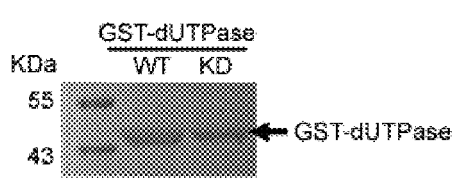
B.
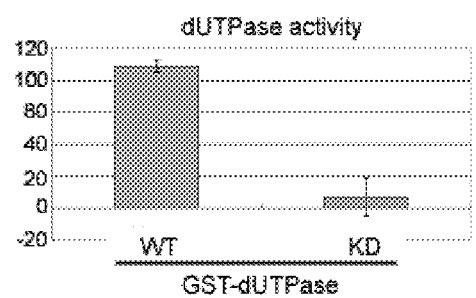

Figure 5. Overexpression of wild-type of dUTPase reduces XRCC1 foci formation and restores sustained DNA damage signal
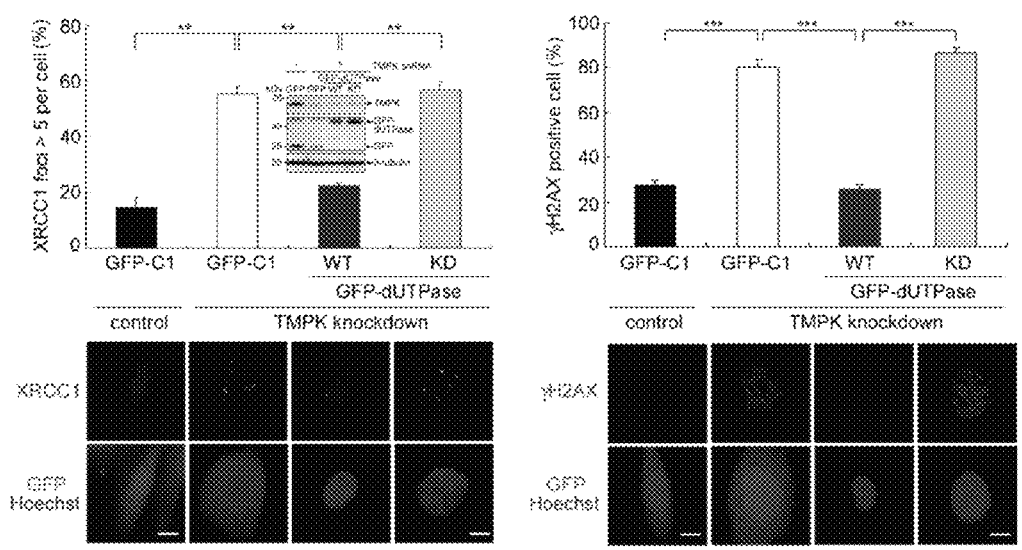

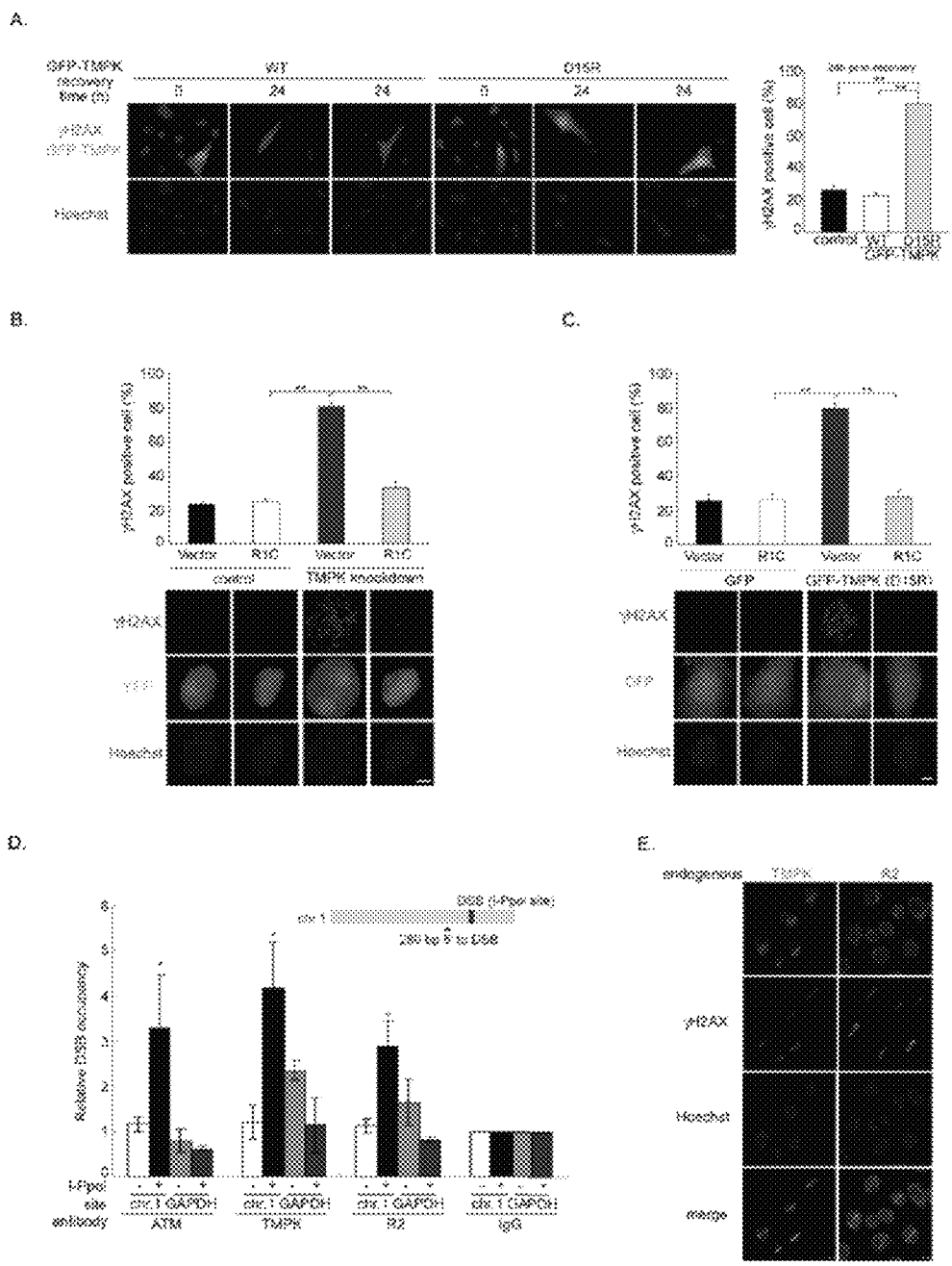
Figure 6. Functional coordination of TMPK and RNR at DNA damage site for repair Figure 7. Effect of TMPK knockdown on cellular dTTP level and cell growth
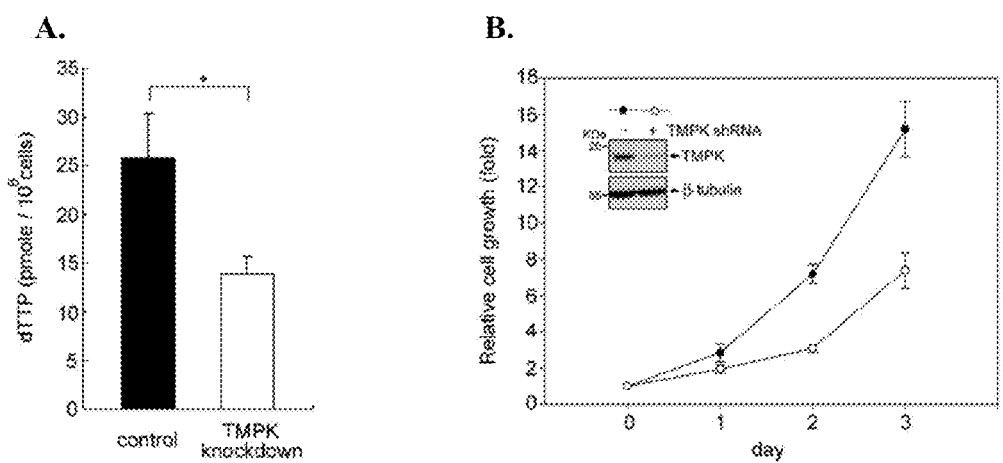

Figure 8. Purified hTMPK activity assay
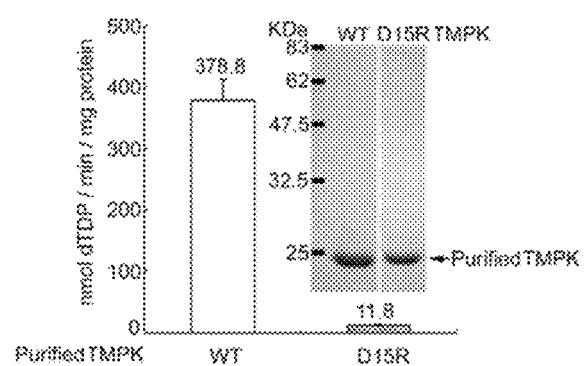

Figure 9. Effect of catalytic dead of GFP-TMPK on cellular dTTP level
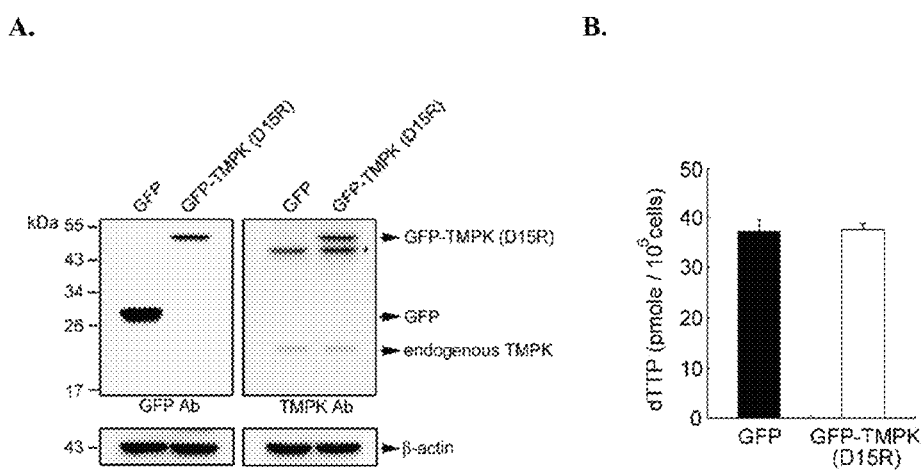

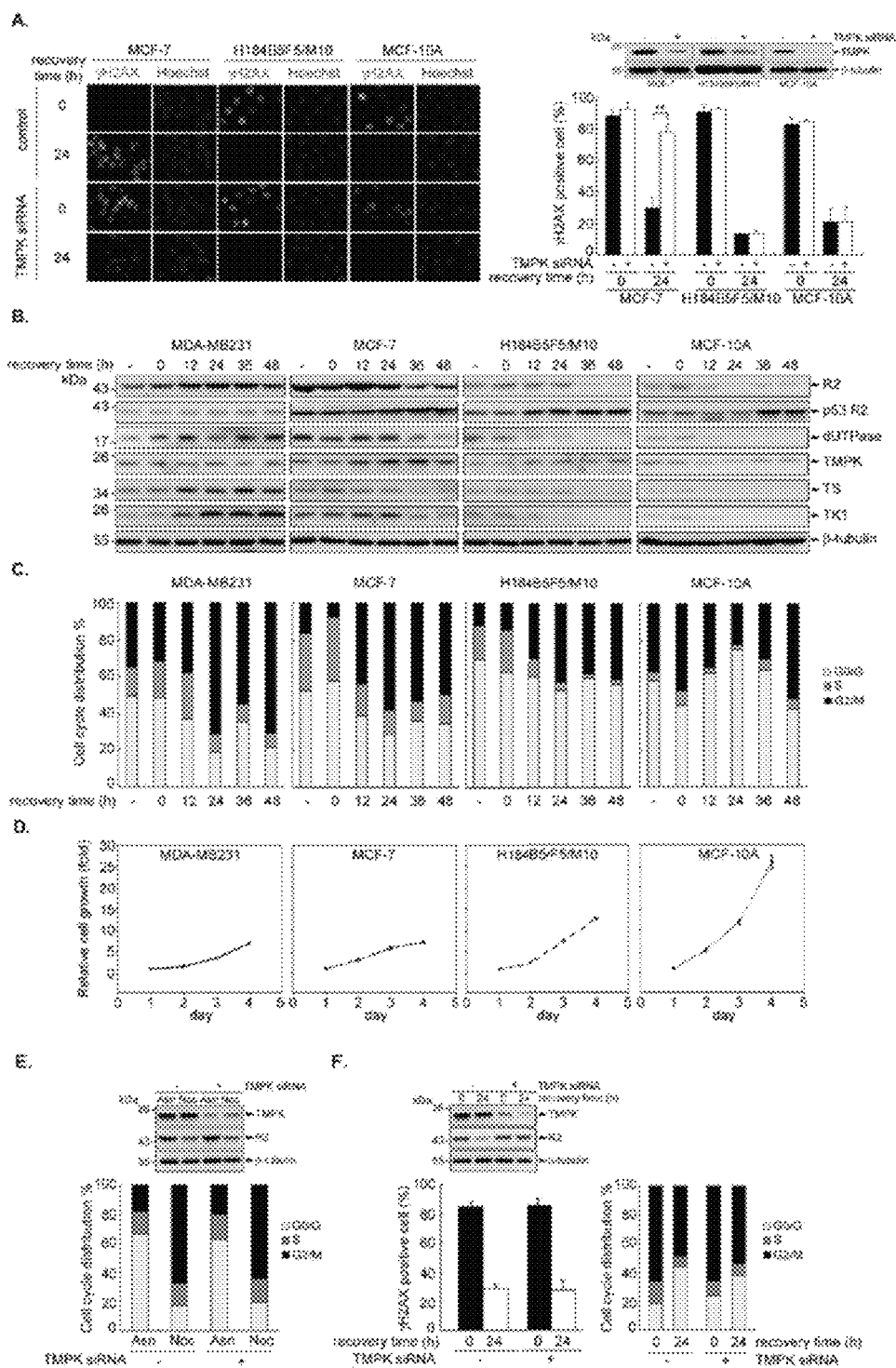
Figure 10. The cellular R2 level is correlated to the requirement of TMPK in DNA repair Figure 11. The contribution of R2 expression level to DNA repair impairment induced by TMPK knockdown
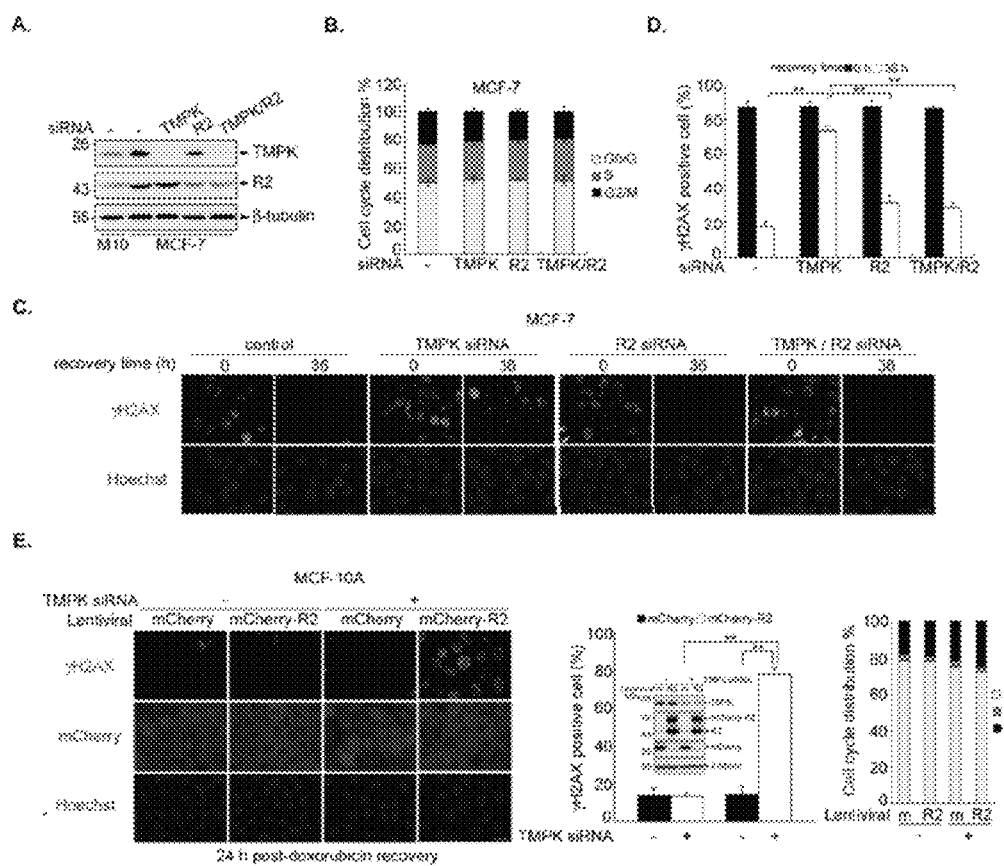

Figure 12. Identification of a novel hTMPK inhibitor
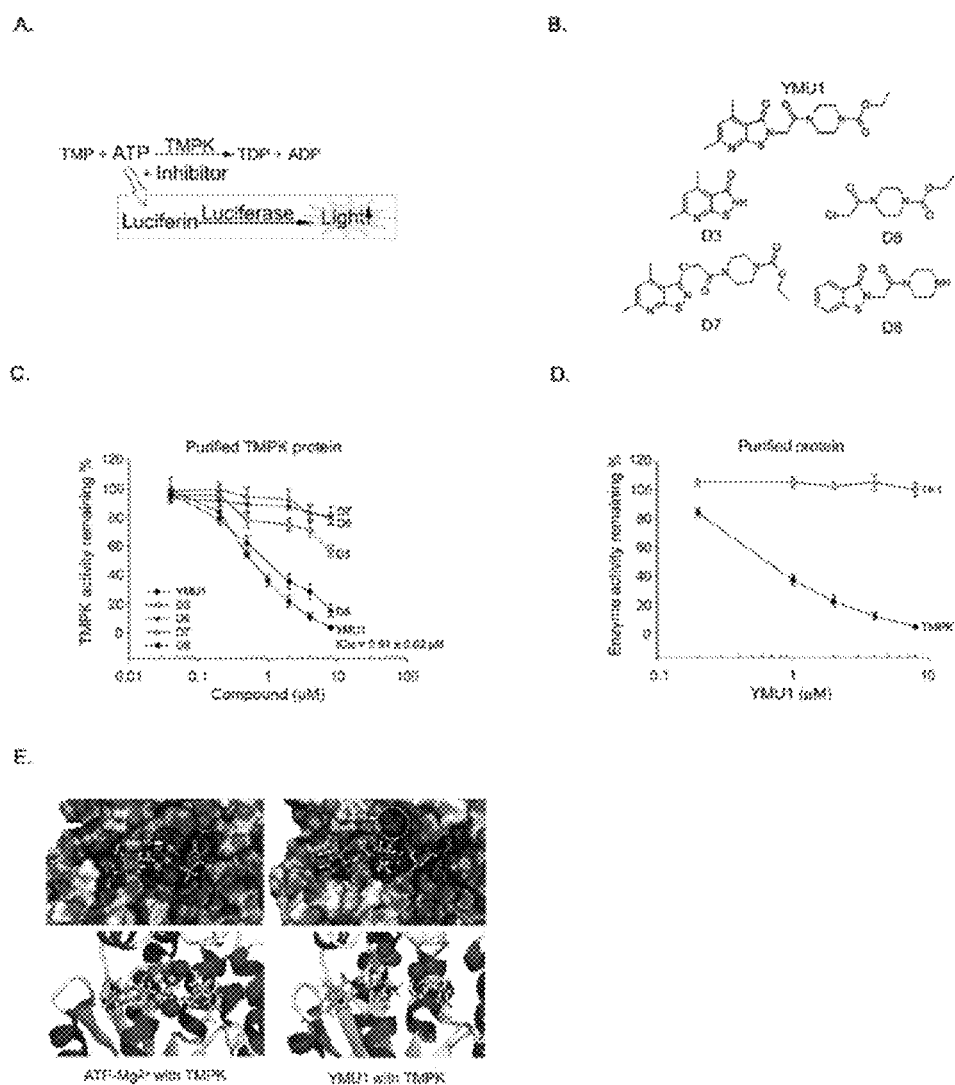

Figure 13. Effect of YMU1 on cellular dTTP level
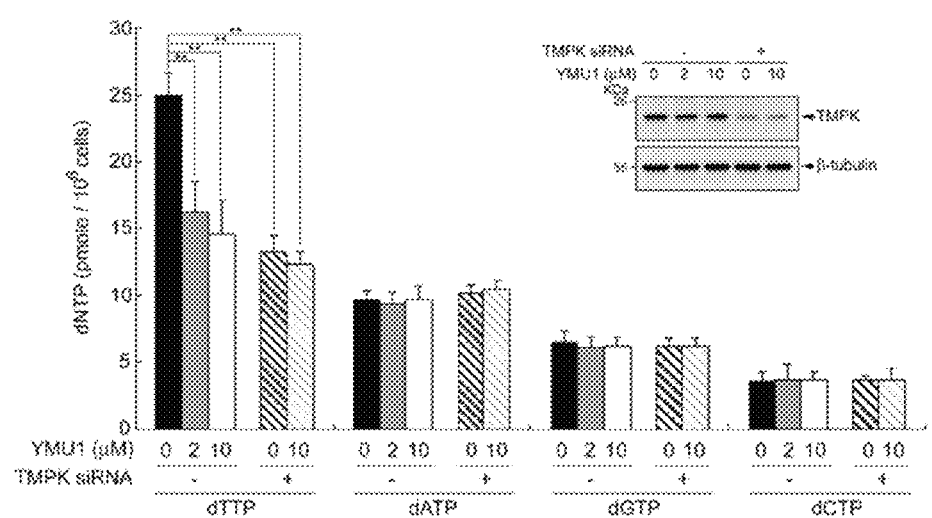

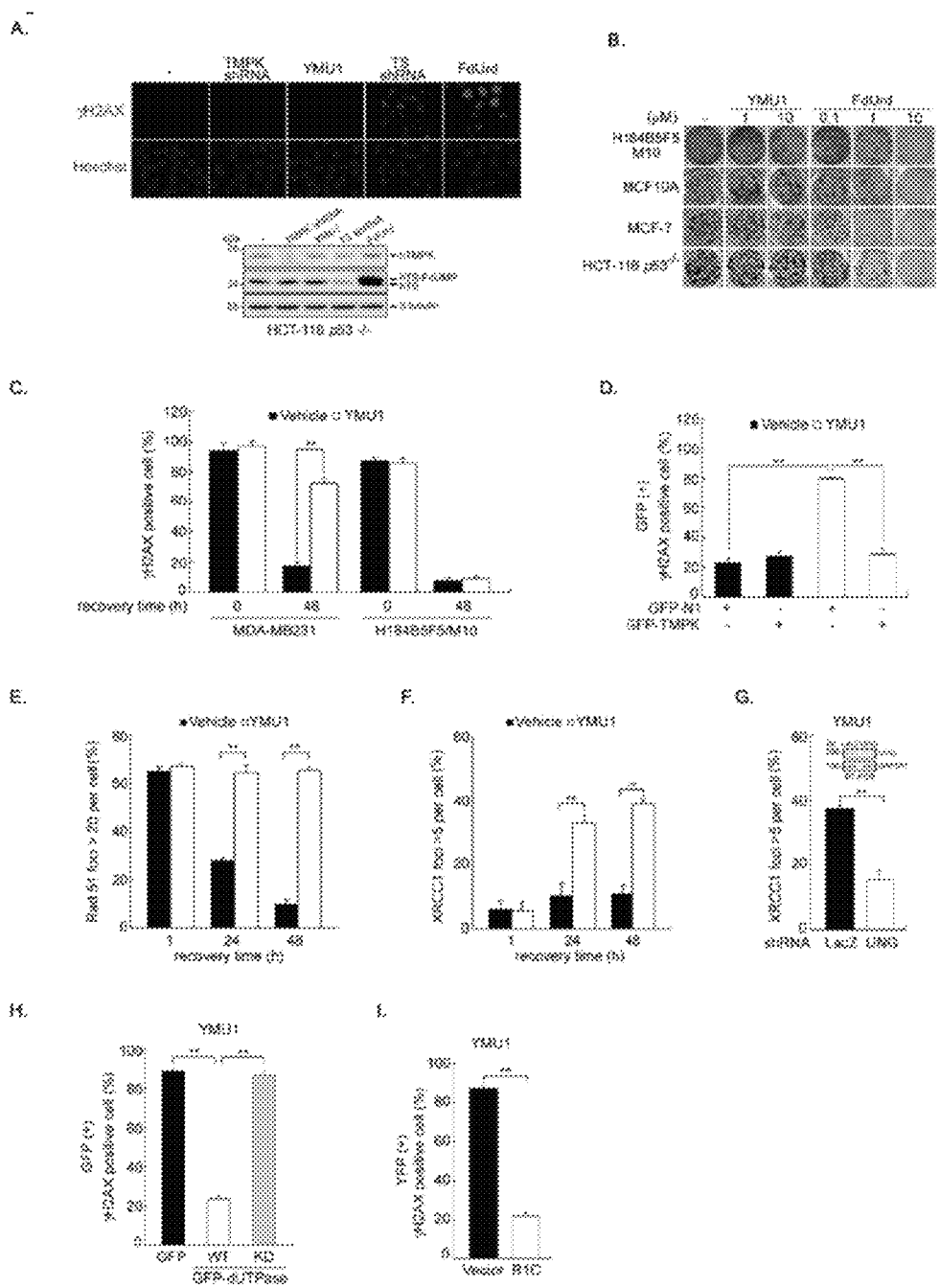
Figure 14. Effect of YMU1 on genomic toxicity and DNA repair

Figure 15. Impairment of DNA repair efficiency by YMU1 treatment in MDAMB231 cells
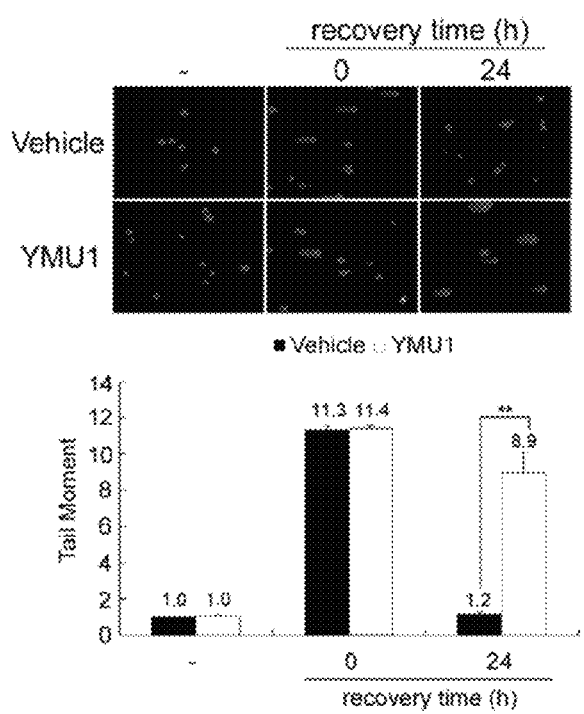

Figure 16. In vitro and in vivo effect of YMU1 on doxorubicin sensitization
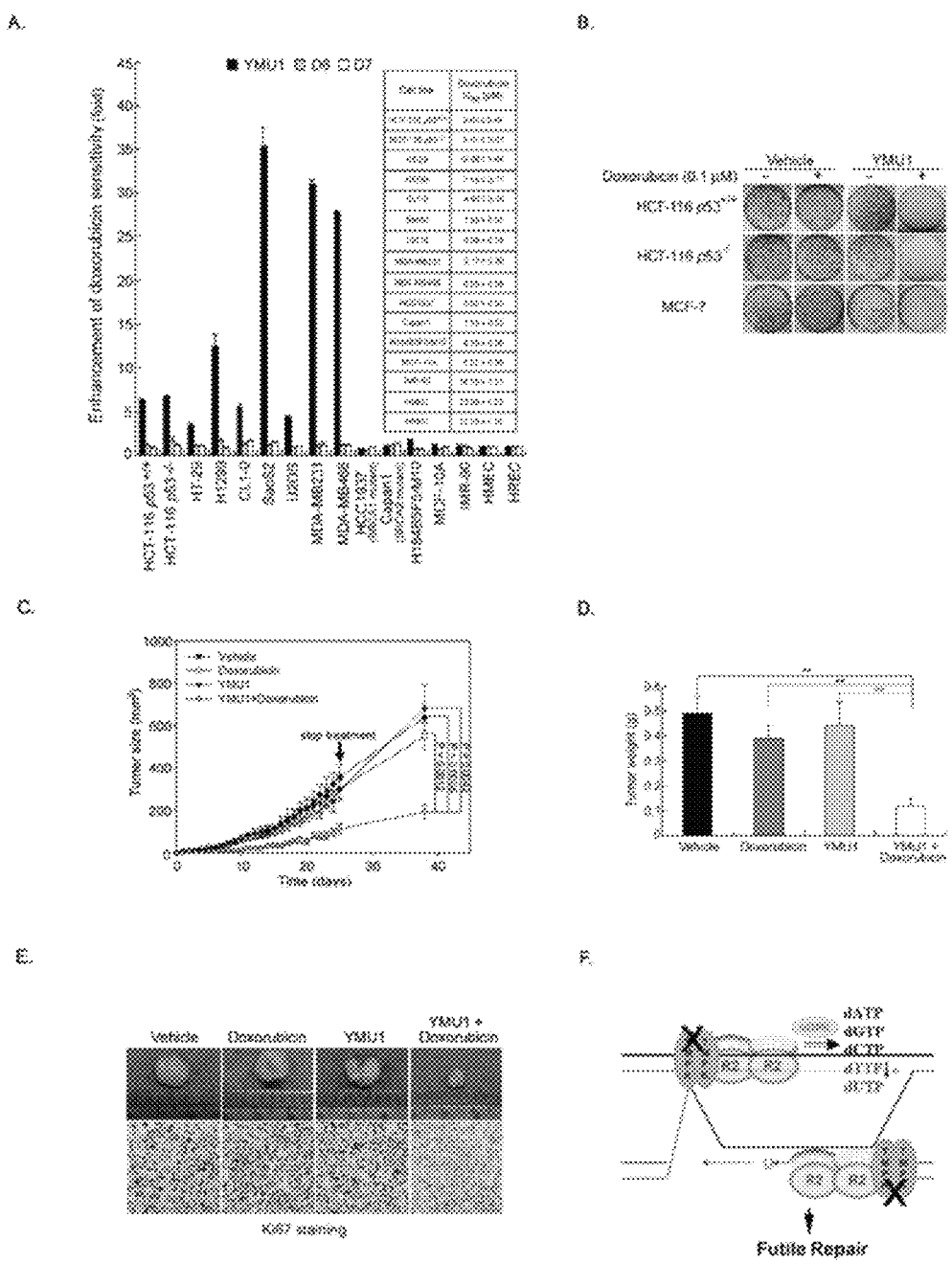

Figure 17. Doxorubicin sensitization by YMU1 is through TMPK inhibition
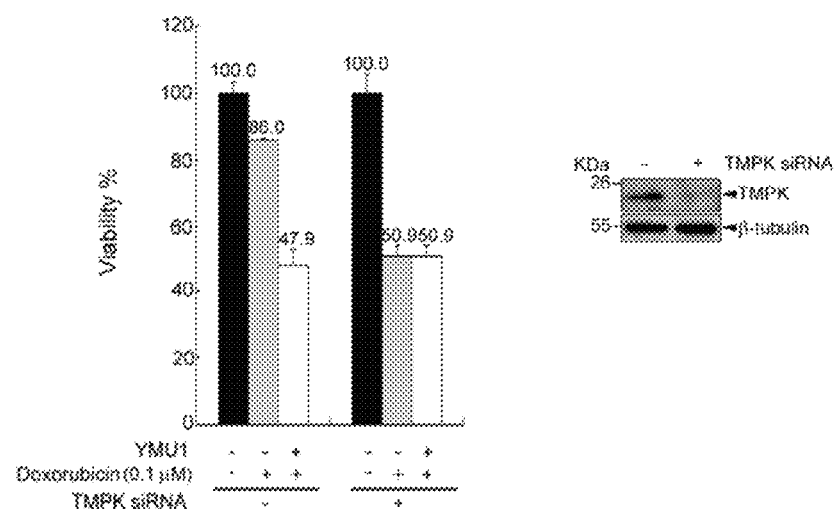

Figure 18. Reversal effect of doxorubicin sensitization with YMU1 treatment by overexpression of dUTPase
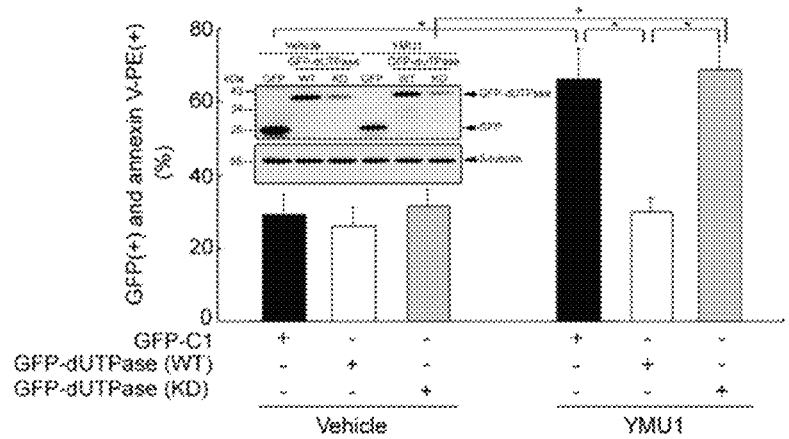

Figure 19. No effect of YMU1 on dUTPase activity
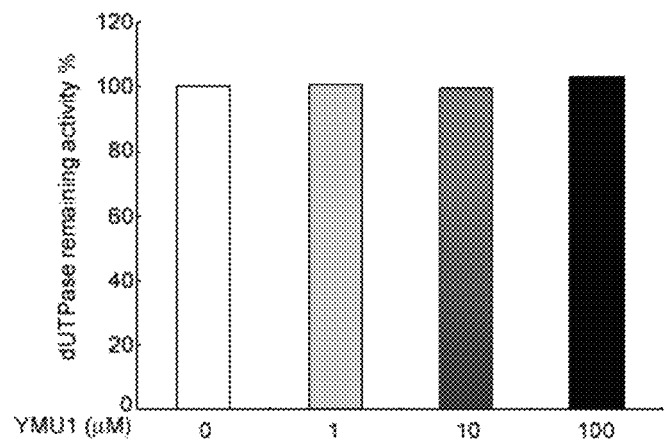

Figure 20. Verification of antibodies specificity
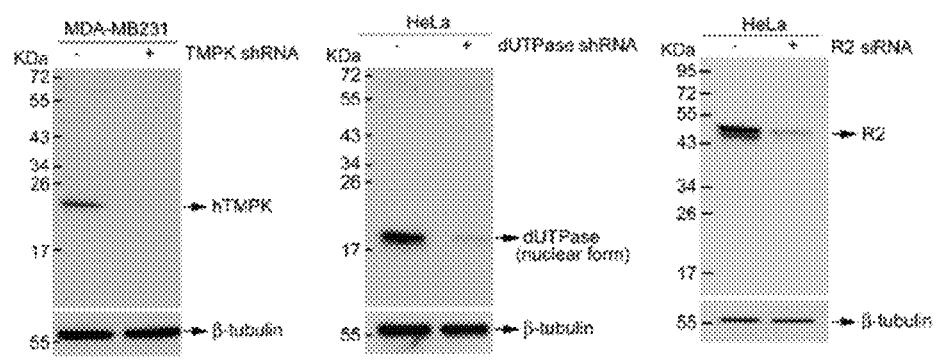

SEQUENCE LISTING

```
<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: LacZ shRNA targeting sequence

<400> SEQUENCE: 1
ctacacaaat cagcgattt                                              19

<210> SEQ ID NO 2
<211> LENGTH: 19
<212> TYPE: DNA
<213> ORGANISM: Artificial Sequence
<220> FEATURE:
<223> OTHER INFORMATION: TMPK shRNA targeting sequence
```

```
<400> SEQUENCE: 2
acacgacttt gaactggaa                                                    19

<210> SEQ ID NO 3
<211> LENGTH: 20
<212> TYPE: DNA
<213> ORGANISM: Artificial Sequence
<220> FEATURE:
<223> OTHER INFORMATION: TS shRNA targeting sequence

<400> SEQUENCE: 3
ggatattgtc agtctttagg                                                   20

<210> SEQ ID NO 4
<211> LENGTH: 21
<212> TYPE: DNA
<213> ORGANISM: Artificial Sequence
<220> FEATURE:
<223> OTHER INFORMATION: UNG shRNA targeting sequence

<400> SEQUENCE: 4
gtctacagac atagaggatt t                                                 21

<210> SEQ ID NO 5
<211> LENGTH: 21
<212> TYPE: DNA
<213> ORGANISM: Artificial Sequence
<220> FEATURE:
<223> OTHER INFORMATION: dUTPase shRNA targeting sequence

<400> SEQUENCE: 5
gcgctccctt ctgggtgtta t                                                 21

<210> SEQ ID NO 6
<211> LENGTH: 18
<212> TYPE: DNA
<213> ORGANISM: Artificial Sequence
<220> FEATURE:
<223> OTHER INFORMATION: R2 siRNA targeting sequence

<400> SEQUENCE: 6
accggaaaag aaaatgct                                                     18

<210> SEQ ID NO 7
<211> LENGTH: 20
<212> TYPE: DNA
<213> ORGANISM: Artificial Sequence
<220> FEATURE:
<223> OTHER INFORMATION: I-PpoI site primer

<400> SEQUENCE: 7
tcactgaaga cttggtggga                                                   20

<210> SEQ ID NO 8
<211> LENGTH: 20
<212> TYPE: DNA
<213> ORGANISM: Artificial Sequence
<220> FEATURE:
<223> OTHER INFORMATION: I-PpoI site primer

<400> SEQUENCE: 8
aaaccatacg tggcagagtg                                                   20

<210> SEQ ID NO 9
<211> LENGTH: 20
```

```
<212> TYPE: DNA
<213> ORGANISM: Artificial Sequence
<220> FEATURE:
<223> OTHER INFORMATION: GAPDH primer

<400> SEQUENCE: 9
gcttgccctg tccagttaat                                              20

<210> SEQ ID NO 10
<211> LENGTH: 20
<212> TYPE: DNA
<213> ORGANISM: Artificial Sequence
<220> FEATURE:
<223> OTHER INFORMATION: GAPDH primer

<400> SEQUENCE: 10
tagctcagct gcaccettta                                              20

<210> SEQ ID NO 11
<211> LENGTH: 20
<212> TYPE: DNA
<213> ORGANISM: Artificial Sequence
<220> FEATURE:
<223> OTHER INFORMATION: UNG primer

<400> SEQUENCE: 11
tcgtgcccat caagccaact                                              20

<210> SEQ ID NO 12
<211> LENGTH: 20
<212> TYPE: DNA
<213> ORGANISM: Artificial Sequence
<220> FEATURE:
<223> OTHER INFORMATION: UNG primer

<400> SEQUENCE: 12
gggagggatg agccgtctgt                                              20

<210> SEQ ID NO 13
<211> LENGTH: 23
<212> TYPE: DNA
<213> ORGANISM: Artificial Sequence
<220> FEATURE:
<223> OTHER INFORMATION: TMPK primer

<400> SEQUENCE: 13
aaatcgctgg gaacaagtgc cgt                                          23

<210> SEQ ID NO 14
<211> LENGTH: 21
<212> TYPE: DNA
<213> ORGANISM: Artificial Sequence
<220> FEATURE:
<223> OTHER INFORMATION: TMPK primer

<400> SEQUENCE: 14
tttgggaagg cccacgtctg g                                            21

<210> SEQ ID NO 15
<211> LENGTH: 19
<212> TYPE: DNA
<213> ORGANISM: Artificial Sequence
<220> FEATURE:
<223> OTHER INFORMATION: GAPDH primer

<400> SEQUENCE: 15
```

```
ccatgttcgt catgggtgt                                              19

<210> SEQ ID NO 16
<211> LENGTH: 19
<212> TYPE: DNA
<213> ORGANISM: Artificial Sequence
<220> FEATURE:
<223> OTHER INFORMATION: GAPDH primer

<400> SEQUENCE: 16
ccaggggtgc taagcagtt                                              19
```

TARGETING HUMAN THYMIDYLATE KINASE INDUCES DNA REPAIR TOXICITY IN MALIGNANT TUMOR CELLS

CROSS REFERENCE TO RELATED APPLICATIONS

This application claims priority to U.S. Application No. 61/417,648, filed Nov. 29, 2010, the entire contents of which is incorporated herein by reference.

STATEMENT OF GOVERNMENT LICENSE RIGHTS

This invention was made with grants NHRI-EX-100-10005NI from National Health Research Institute, NSC 96-2628-B-002-079-MY2 from National Science Council, Taiwan and a grant from Aim for the Top University plan in National Yang-Ming University supported by the Ministry of Education, Taiwan.

FIELD OF THE INVENTION

The present invention relates to novel TMPK inhibitor compositions and their methods of use. In particular, it relates to novel TMPK inhibitor compositions, synthesis scheme, and therapeutics that lead to dUTP-mediated DNA toxic repair in malignant tumor cells with elevation of ribonucleotide reductase. Such novel TMPK inhibitor compositions and therapeutics may acts as novel chemosensitizers, which are useful in methods for treating or preventing cancers.

BACKGROUND OF THE INVENTION

The main problem with cancer chemotherapy is the lack of differentiation between tumor- and rapidly-dividing cells in normal tissues. This causes substantial side effects, which can in the long run lead to secondary cancers induced by the treatment. Chemotherapeutic agents often cause unwanted general cytotoxicity, and activities of several DNA repair pathways enable tumor cells to survive by removing lesions (Helleday et al., 2008).

Small-molecule inhibitors of checkpoint pathways or DNA repair machineries were identified and used as cellular radio- and chemosensitization compounds in clinical trials (Bolderson et al., 2009). Given the differences in checkpoint and DNA repair alteration during tumorigenesis, the therapeutic efficacies of these strategies were found various depending on the checkpoint context of tumor (Jackson and Bartek, 2009; Jiang et al., 2009).

Moreover, derangement of DNA damage response could cause the accumulation of DNA error during therapy, which might provoke secondary tumor development (Mimeault et al., 2008). Therefore, it is important to develop a chemosensitization regimen that does not disrupt the checkpoint network while specifically inducing cancer cell death with little side effect.

An important process in DNA repair is the supply of balanced and sufficient quantities of four dNTPs (Niida et al., 2010b). Ribonucleotide reductase (RNR)-mediated reduction generates not only dADP, dGDP and dCDP but also dUDP, directly from the corresponding NDPs (Nordlund and Reichard, 2006). RNR is composed of R1 and R2 subunits, of which the level of R2 is cell-cycle-regulated (Bjorklund et al., 1992; Engstrom et al., 1985) and often elevated in tumor cells (Jensen et al., 1994; Zhang et al., 2009). It has been reported that R2 overexpression confers oncogenic potential (Fan et al., 1998). An analogue of R2, p53R2, can substitute for R2 to form RNR enzyme, and its function is important for DNA repair in quiescent cells (Hakansson et al., 2006; Pontarin et al., 2011). Nucleotide diphosphate kinase converts all these dNDPs to dNTPs, which include dUTP (Mathews, 2006; Reichard, 1988). Pyrophosphorolysis of dUTP by dUTPase or deamination of dCMP forms dUMP, which is converted to dTMP by thymidylate synthase (TS) (Mathews, 2006; Reichard, 1988). The action of thymidine kinase (TK) also generates dTMP from thymidine (Amer and Eriksson, 1995). Thymidylate kinase (TMPK) subsequently catalyzes the formation of dTDP (Ostermann et al., 2000; Reichard, 1988). Thus, dTDP is the only dNDP, the formation of which cannot be directly derived from RNR reaction.

Conventional anti-cancer therapies often directly induce genotoxicity (Garg et al., 2010). For example, thymidylate synthase (TS) inhibitor, 5-FU or 5-FdUrd, blocks the conversion of dUMP to dTMP, causing dUTP to accumulate and 5-FdUTP formation (Longley et al., 2003). Since DNA polymerases cannot discriminate between dUTP and dTTP (Bessman et al., 1958; Mosbaugh, 1988), excessive amounts of dUTP and 5FdUTP are mis-incorporated into DNA, triggering DNA damage-induced cell death (Ahmad et al., 1998). Consequently, such anti-metabolites produce excessive DNA damage due to erroneous nucleotide incorporation and causes cancer cells death while being highly toxic to normal cycling cells (Ahmad et al., 1998).

It is known that double-strand breaks (DSBs) in proliferating cells are mainly repaired by homologous recombination (HR) in which a single DSB needs more than 10 thousands of dNTPs new incorporation (Robert et al., 2011; San Filippo et al., 2008). As such, RNR function in supply of dNTPs is critical for HR repair (Burkhalter et al., 2009). Of note, blocking RNR on its own induces DNA damage signal and replication stress (Helleday et al., 2008). Since dTDP formation specifically requires TMPK function, we propose that blocking TMPK may decrease the efficiency of DSBs repair and sensitize tumor cells to genotoxic insults.

Accordingly, there is a need to develop novel therapeutics than can induce cancer cell death, when used alone or in combination with other anti-cancer therapies, while reducing the toxic effects caused by such treatments.

SUMMARY OF THE INVENTION

The present invention provides novel compositions, their synthesis schemes and their methods of use. More particularly, the inventors have identified novel compositions and therapeutics comprising TMPK inhibitors and methods of use in treating or preventing cancers.

The present invention provides a composition for inhibiting thymidylate kinase (TMPK) comprising a therapeutically effective amount of formula (I):

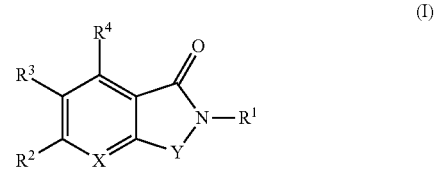

wherein

X=CH or N;

Y=S, SO$_2$, O, C=O, or NR$^5$, wherein R$^5$ is a substituent selected from the group consisting of hydrogen, a straight, branched or cyclic alkyl group, aralkyl, heteroaralkyl, heteroarakenyl, aryl, heteroaryl, optionally substituted with one or more substituents such as halogen, alkyl, hydroxyl, alkoxy, amino, nitro, cyano and carbonyl;

R$^1$=(CH$_2$)$_n$COR$^6$, wherein n is 0, 1, 2, or 3; and

R$^2$, R$^3$, R$^4$ and R$^6$ are substituents independently selected from the group consisting of hydrogen, a straight, branched or cyclic alkyl group, a straight, branched or cyclic alkenyl group, a straight, branched or cyclic alkoxyl group, fluoroalkyl, perfluoroalkyl, aralkyl, arakenyl, arakynyl, heteroaralkyl, heteroarakenyl, heteroarakynyl, aryl, heteroaryl, optionally substituted with one or more substituents such as halogen, alkyl, hydroxyl, alkoxy, amino, nitro, cyano and carbonyl;

or a pharmaceutically acceptable salt, hydrate or solvate thereof.

In some embodiments of the present invention, the composition comprises at least one of the following structures:

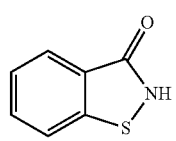

1

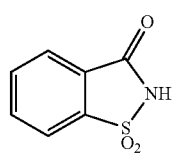

2

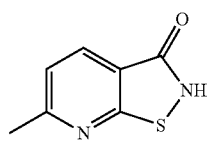

3

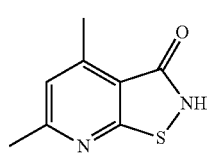

4

In some embodiments of the present invention, the composition comprises the following structure:

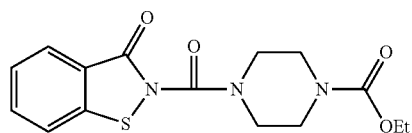

5

In some embodiments of the present invention, the composition comprises at least one of the following structures:

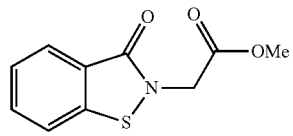

6

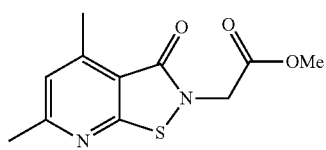

7

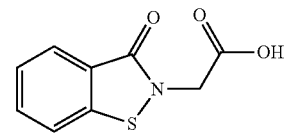

8

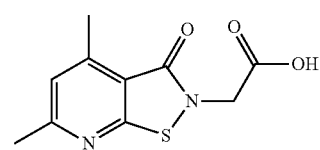

9

In some embodiments of the present invention, the composition comprises at least one of the following structures:

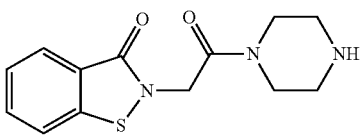

10

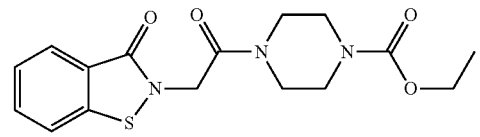

11

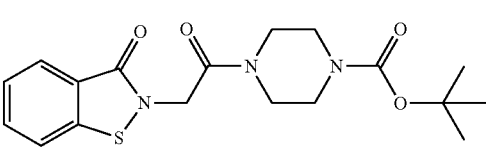

12

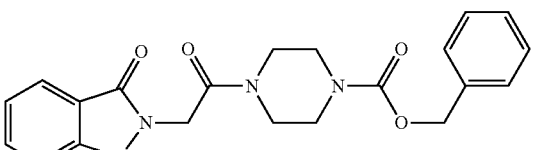

13

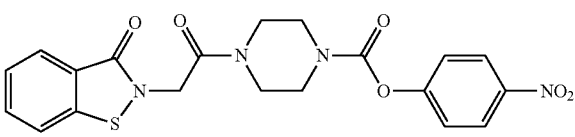

14

In some embodiments of the present invention, the composition comprises the following structure:

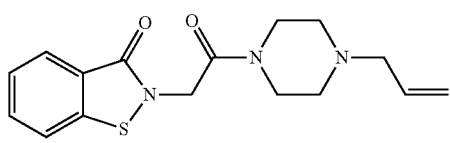

In some embodiments of the present invention, the composition comprises at least one of the following structures:

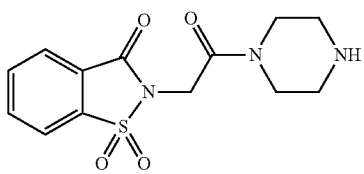

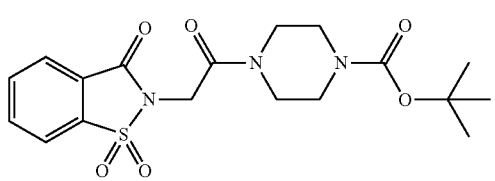

In some embodiments of the present invention, the composition comprises the following structure:

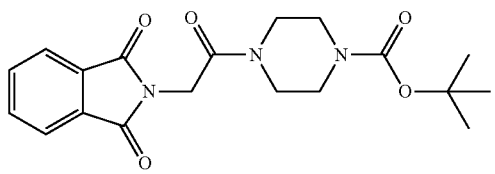

In some embodiments of the present invention, the composition comprises at least one of the following structures:

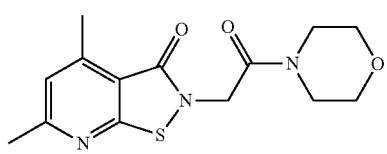

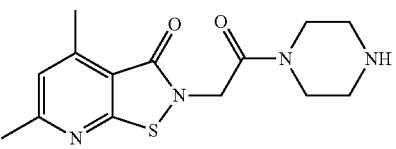

In some embodiments of the present invention, the composition comprises at least one of the following structures:

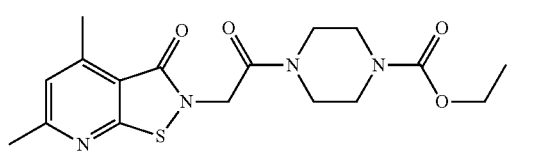

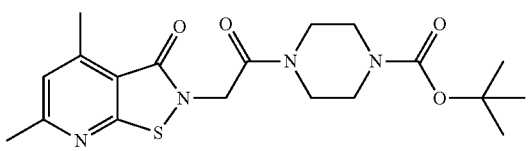

In some embodiments of the present invention, the composition comprises the following structure:

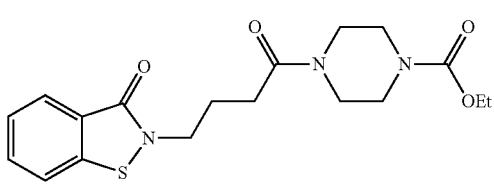

In some embodiments of the present invention, the composition comprises the following structure:

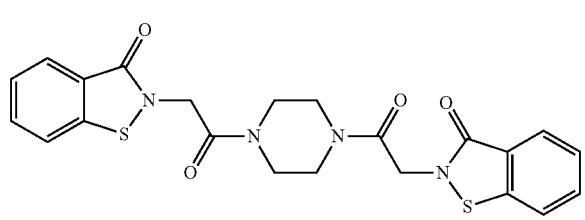

In some embodiments of the present invention, the composition comprises at least one of the following structures:

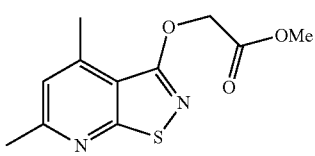

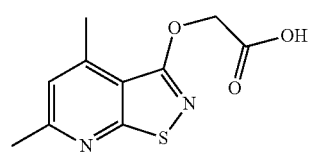

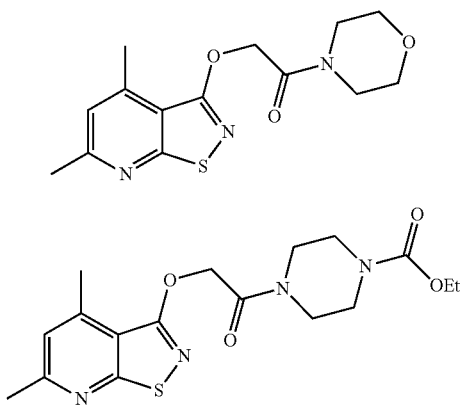

In some embodiments, the compositions of the present invention are capable of inhibiting TMPK activity. In other embodiments, the compositions of the present invention are capable of inhibiting cellular dTTP levels. In some embodiments, the compositions of the present invention are capable of inhibiting tumor growth, DNA damage checkpoint, DNA mismatch repair, nucleotide excision repair, double-strand break repair, DNA helicase function, signaling, cell cycle control or apoptosis.

In some embodiments, the double-strand break repair may be associated with radiation therapy, chemotherapy or immunomodulatory therapy. In some embodiments, the chemotherapy involves treatment with doxorubicin.

In some embodiments, the compositions of the present invention selectively target toxicity to cancer cells with DNA lesions.

In other embodiments, the compositions of the present invention are capable of sensitizing cancer cells to radiation therapy, chemotherapy or immunomodulatory therapy. In some embodiments, the chemotherapy involves treatment with doxorubicin.

In some embodiments, the compositions of the present invention do not result in genotoxic side effects.

In some embodiments, the compositions of the present invention exhibit an $IC_{50}$ value of about 10 μM or less. In some embodiments, they exhibit an $IC_{50}$ value of about 5 μM or less. In some embodiments, the compositions exhibit an $IC_{50}$ value of about 1 μM or less. In some embodiments, the compositions exhibit an $IC_{50}$ value of about 0.5 μM or less. In still other embodiments, the compositions exhibit an $IC_{50}$ value of about 0.25 μM or less. In other embodiments, the compositions exhibit an $IC_{50}$ value of about 0.1 μM or less.

In some embodiments, the compositions of the present invention are administered once daily for 3 consecutive days. In some embodiments, the compositions of the present invention are administered one to two times per day. In some embodiments, the compositions of the present invention are administered at a dose of about 5 mg/kg to about 30 mg/kg.

The present invention further provides a pharmaceutical composition comprising a composition described herein and a pharmaceutically acceptable carrier.

The present invention also provides a method for manufacturing a composition described herein comprising the steps a-u as illustrated in FIG. 1.

The present invention further provides a method of sensitizing cancer cells to radiation therapy, chemotherapy or immunomodulatory therapy comprising exposing the cancer cells to an effective amount of a composition of the present invention.

The present invention also provides a method for sensitizing cancer cells to the therapeutic effects of radiation therapy, chemotherapy or immunomodulatory therapy comprising exposing the cancer cells to an effective amount of an agent that inhibits TMPK activity. In some embodiments, the agent is a composition of the present invention.

The present invention further provides a method of preventing double-strand break repair of cancer cells comprising exposing the cancer cells to an effective amount of a composition of the present invention.

The present invention also provides a method of selectively targeting toxicity to cancer cells with DNA lesions comprising exposing the cancer cells to an effective amount of a composition of the present invention.

In some embodiments, the cancer cell is selected from the group consisting of a breast cancer cell, a hepatoma cell, a colorectal cancer cell, pancreatic carcinoma cell, an esophageal carcinoma cell, a bladder cancer cell, an ovarian cancer cell, a skin cancer cell, a liver carcinoma cell, a gastric cancer cell, a prostate cancer cell, a colon cancer cell, a lung cancer cell, a rectal cancer cell, a renal cancer cell, a thyroid cancer cell, a brain cancer cell, melanoma, sarcoma, leukemia, bone cancer cell and endometrial cancer cell.

In some embodiments, the methods further comprise exposing the cancer cells to at least one additional therapeutic agent selected from the group consisting of anti-cancer agents, antiviral agents, anti-inflammatory agents and immunosuppressive agents.

The present invention also provides a method of treating or preventing cancer in a subject in need thereof, comprising administering to said subject a therapeutically effective amount of a composition of the present invention.

In some embodiments, the composition is administered via inhalation, nasal spray, aerosol spray, orally, intravenously, intraperitoneally, subcutaneously, via a sustained-release delivery system or combinations thereof.

In some embodiments, the method further comprises administering at least one additional anti-cancer therapy selected from the group consisting of radiation therapy, chemotherapy or immunomodulatory therapy.

In some embodiments, the anti-cancer therapy is administered prior to administration of the composition. In some embodiments, the anti-cancer therapy is administered simultaneously with administration of the composition.

In some embodiments, the cancer is selected from the group consisting of breast cancer, hepatoma, colorectal cancer, pancreatic carcinoma, esophageal carcinoma, bladder cancer, ovarian cancer, skin cancer, liver carcinoma, gastric cancer, prostate cancer, colon cancer, lung cancer, rectal cancer, renal cancer, thyroid cancer, brain cancer, melanoma, sarcoma, leukemia, bone cancer and endometrial cancer.

In some embodiments, the subject is a mammal.

These and other features, aspects and advantages of the present invention will become better understood with reference the following description, examples and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. TMPK knockdown causes DSB repair with dUTP incorporation. (A) After silencing of TMPK with siRNA for 24 h, U2OS-DR-GFP cells were transfected with pCBA-I-SceI plasmid. After 48 h, GFP+ frequencies were measured by flow cytometric analysis. Data are presented as mean±s.d., n=3. A proportion of cells were harvested for WB analysis. (B-D) MDA-MB231 cells without and with TMPK shRNA stable expression were exposed to doxorubicin (0.1 µM) for 4 h and recovered by washing with fresh medium for (B) γH2AX foci staining (Scale bar, 20 µm). (C) Rad51 foci staining (Scale bar, 5 µm). (D) XRCC1 foci staining (Scale bar, 5 µm). For each experiment, more than 100 of cells were counted (n=3). The level of TMPK was indicated by Western blot. (E) Cells were infected with lentiviral LacZ or UNG shRNA for 8 hr. After 24 h recovery from doxorubicin exposure, cells were fixed for XRCC1 foci staining (Scale bar, 5 µm). Inset indicates the levels of UNG and TMPK RNA transcript by RT-PCR. For each experiment, more than 100 of cells were counted (n=3). (F) Cells were transfected with pEGFP-C1, wild-type pEGFP-dUTPase (wt) and catalytic-dead pEGFP-dUTPase (KD) as indicated, followed by doxorubicin exposure and recovered for 24 h. Cells were analyzed by XRCC1 foci staining (Scale bar, 10 µm). For each experiment, 70~100 of GFP-positive cells were counted (n=3). Inset indicates the level of TMPK by Western blot.

FIG. 3. Effect of TMPK knockdown on viability in response to DNA damage. (A) Parental MDA-MB231 and stable clone expressing TMPK shRNA were plated in a 96 well plate at 1,000 cell per well for cell growth analysis by MTS assay. (B) Overnight culture these two cells were exposed to doxorubicin (0.1 µM) for 4 h, after which drug was removed by washing with fresh medium. After 48 h, cell viability was determined by MTS assay. Data represent mean±s.d. of 4 experiments.

FIG. 4. Measurement of recombinant human dUTPase activity. (A) Recombinant human GST-dUTPase fusion protein was eluted from glutathione-sepharose with glutathione after affinity chromatography. Proteins were separated on a 10% SDS PAGE and stained with coomassie blue. (B) The enzyme specific activity was calculated by measuring the concentration of PPi in each reaction containing 0.25 µg of dUTPase (data represent mean±s.d., n=3).

FIG. 5. Overexpression of wild-type of dUTPase reduces XRCC1 foci formation and restores sustained DNA damage signal. Parental MDA-MB231 and the clone cells stably expressing TMPK shRNA were transfected with indicated plasmid. After overnight, cells were exposed to doxorubicin (0.1 µM) for 4 h and recovered. At 24 h recovery, cells were analyzed by XRCC1 and γH2AX foci staining. Quantification of the number of GFP-positive cells with XRCC1 foci >5, γH2AX foci >10 is shown in upper panel. Representative images were shown in lower panel. Data are presented as mean±s.d., n=3; ***, P<0.001 based on a two-tailed Student's t-test. For each experiment, 70~100 of GFP cells were counted. Scale bar, 10 µm.

FIG. 6. Functional coordination of TMPK and RNR at DNA damage site for repair. (A) MDA-MB231 cells were transfected with pEGFP-TMPK (WT or D15R) followed by doxorubicin exposure and recovered as described in legend to FIG. 2B. Cells were fixed for γH2AX staining. Scale bar, 20 µm. For each experiment, more than 100 of GFP-positive cells were counted (n=3). (B) MDA-MB231 cells without and with stable TMPK shRNA expression were transfected with pCMV2-YFP-Nuc (vector) or pCMV2-YFP-Nuc-R1C (R1C) plasmid. (C) MDAMB-231 cells were transfected with pEGFP-TMPK (D15R) in combination with pCMV2-YFP-Nuc-R1C (R1C) plasmid as indicated. Following doxorubicin exposure and recovery for 24 h, cells were analyzed by γH2AX foci staining (Scare bar, 5 µm (B) and 10 µm (C)). For each experiment, more than 100 of YFP or GFP positive cells were counted (n=3). (D) HEK293T cells were transfected with pEGFP-C1 or pEGFP-I-Ppol. After 18 h, cells were collected and used for qChIP analysis with the indicated antibody using a primer pair adjacent to the single chromosome 1 I-Ppol cleavage site (280 bp 5' to the I-Ppol cut site). GAPDH serves as a genomic DNA control as it has no I-Ppol site. Data are normalized by IgG control. Data are presented as mean±s.d., n=3. (E) HeLa cells were plated on glasses-like dishes for micro-irradiation. After recovery for 5 min, cells were fixed for γH2AX, TMPK and R2 staining and observed by FluoView 1000 confocal microscope (Olympus). Scale bar, 10 µm.

FIG. 7. Effect of TMPK knockdown on cellular dTTP level and cell growth. (A) HCT-116 $p53^{-/-}$ stably expressing TMPK shRNA were extracted for dTTP level determination. (B) A proportional of cells was plated into 96-well plates. Cell growth at the indicated time was measured by MTS assay and data were expressed relative to day 0 that was set arbitrarily to 1 (mean±s.d., n=3; each assay was in quadruplex). Inset indicated the level of TMPK by WB analysis.

FIG. 8. Purified hTMPK activity assay. TMPK activity assay of GST-TMPK (WT) and GST-TMPK (D15R) mutant proteins using conventional TMPK assay.

FIG. 9. Effect of catalytic dead of GFP-TMPK on cellular dTTP level. After transfection of GFP or GFP-TMPK (D15R) for 72 hr, HeLa cells were harvested for WB analysis (A) and dTTP level determination (B) (data represent mean±s.d., n=3).

FIG. 10. The cellular R2 level is correlated to the requirement of TMPK in DNA repair. (A) MCF-7, H184B5F5/M10 and MCF-10A cells were transfected with TMPK siRNA and exposed to doxorubicin and recovered for γH2AX foci staining (Scare bar, 20 µm) as described in legend to FIG. 2B. For each experiment, more than 100 of cells were counted (n=3). (B-C) MDA-MB231, MCF-7, H184B5F5/M10 and MCF-10A cells were exposed to doxorubicin and recovery as described above. Cells were harvested at the indicated time points for Western blotting (B) and flow cytometric analysis (C). (D) Cells were plated in a 96 well plate at 1,000 per well for cell growth analysis by MTS assay. After TMPK siRNA transfection for 36 h, H184B5F5/M10 cells were treated 500 ng/ml of nocodazole overnight to increase S/G2 cells. A proportion of cells were harvested for Western blotting and FACS analysis (E). Cells were exposed to doxorubicin (0.2 µM) for 2 h and recovered by replenishing with fresh medium. At indicated time points cells were fixed for γH2AX foci staining and FACS analysis (F). For each experiment, more than 200 cells were counted (n=3).

FIG. 11. The contribution of R2 expression level to DNA repair impairment induced by TMPK knockdown. MCF-7 cells were transfected with siRNA of TMPK, R2 or TMPK/R2. 36 h post-transfection a proportion of cells were harvested for (A) Western blotting and (B) FACS analysis. (C) The rest of cells were exposed to doxorubicin (0.1 µM) for 4 h. Cells at indicated time point were analyzed by γH2AX foci staining (Scare bar, 20 µm). (D) For each experiment, more than 150 of cells were counted (n=3). (E) MCF-10A cells stably expressing mCherry or mCherry-R2 by lentiviral infection were transfected with TMPK siRNA followed by doxorubicin exposure and recovery. After recovery for 24 h, cells were fixed for γH2AX foci staining (Scare bar, 20 µm) and harvested for Western blotting and FACS analysis. For each experiment, more than 150 of cells were counted (n=3).

FIG. 12. Identification of a novel hTMPK inhibitor. (A) A screen of TMPK inhibitor by luciferase-coupled assay. (B) The chemical structures of YMU1 (compound 21) and related molecules. (C) Effect of YMU1 and derivative compounds on hTMPK inhibition using purified hTMPK protein (0.5 μg) with 10 min preincubation prior to reaction using luciferase-coupled TMPK analysis. (D) Effect of YMU1 on activity of purified TMPK (0.5 μg) and GST-hTK1 protein (5 μg) with 10 min preincubation prior to reaction. Data represent mean±s.d. (n=4) (E) Molecular models of the TMPK-YMU1 complex. Left panel: TMPK/ATP/Mg+2; right panel: TMPK/YMU1. The TMPK is represented in surface electrostatic potential (upper) and structural ribbon (lower). ATP and YMU1 are shown in green and blue stick, respectively, with colored atom (O, red; S, yellow; P, orange). TMP is shown in white backbone and Mg+2 in purple. Arrow indicates the position of Asp15.

FIG. 13. Effect of YMU1 on cellular dTTP level. HCT-116 p53−/− cells were transfected with or without TMPK siRNA for 2 days and treated with vehicle or YMU1. After 72 h, cells were harvested for Western blot analysis and dNTP level determination (mean±s.d., n=3; **, P<0.01 based on a two-tailed Student's t-test).

FIG. 14. Effect of YMU1 on genomic toxicity and DNA repair. (A) HCT-116 p53−/− cells were infected with lentiviral shRNA of TMPK or TS. In parallel, cells were treated with YMU1 (2 μM) for 2 days, or 5-fluoro-2'deoxyuridine (FdUrd, 2 μM) for 1 day. These cells were fixed for γH2AX foci staining and Western blotting analysis. (B) H184B5F5/M10 cells were seeded onto 100 mm-dish at 5,000 cells/dish. MCF-10A, MCF-7 and HCT-116 p53−/− cells were seeded onto 6 well plate at 600 cells/well. Following overnight culture, cells were treated with various concentration of YMU1 or FdUrd thrice a week. After 14 days colonies were fixed, stained by crystal violet. (C) Cells were pre-treated with vehicle or YMU1 (2 μM) for 72 h prior to doxorubicin (0.1 μM) exposure. After release from doxorubicin treatment, cells were fixed for γH2AX foci staining at the indicated time. For each experiment, more than 100 of cells were counted (n=3). (D) MDA-MB231 cells after vehicle or YMU1 (2 μM) treatment for 48 h were transfected with pEGFP-N1 or pEGFP-TMPK plasmid. After overnight, cells were exposed to doxorubicin and recovered. At 24 h, cells were analyzed by γH2AX foci staining. For each experiment, 70~100 of GFP positive cells were counted (n=3). (E-F) MDA-MB231 cells pre-treated with vehicle or YMU1 (2 μM) for 72 h were exposed to doxorubicin and recovered for (E) Rad51 foci (F) XRCC1 foci staining. For each experiment, more than 100 of cells were counted (n=3). (G) Cells were infected with lentiviral LacZ or UNG shRNA for 8 hr. After exposure to doxorubicin and recovered for 24 h, cells were fixed for XRCC1 foci staining. Inset indicates the levels of UNG RNA transcript by RT-PCR. For each experiment, more than 100 of cells were counted (n=3). (H-I) MDA-MB231 cells pre-treated with YMU1 (2 μM) for 48 h were transfected with indicated plasmid or shRNA. After overnight, cells were exposed to doxorubicin and recovered. After 24 h, cells were analyzed by γH2AX foci staining. For each experiment, 70~100 of GFP or YFP positive cells were counted (n=3).

FIG. 15. Impairment of DNA repair efficiency by YMU1 treatment in MDA-MB-231 cells. DNA repair efficiency was measured by comet assay at indicated time after removal of doxorubicin (0.1 μM) in MDA-MB231 cells. Image of DNA comet was acquired and quantified by using scion image software for tail moment determination. Data were expressed as mean±s.d. by counting at least 70 comets per sample in 3 independent experiments. **, P<0.01 based on a two-tailed Student's t-test.

FIG. 16. In vitro and in vivo effect of YMU1 on doxorubicin sensitization. (A) A panel of cell lines were pre-treated with vehicle, YMU1 (compound 21), D6 (ethyl 4-(2-chloroacetyl)piperazine-1-carboxylate) or D7 (compound 28) for 3 days and were exposed to different concentration of doxorubicin for 4 h. After 48 h recovery from doxorubicin exposure, cells were washed with fresh medium for MTS assay and $IC_{50}$ of doxorubicin was determined. The enhancement (fold) of doxorubicin sensitivity in each cell line was calculated. Data represent mean±s.d., n=3; each experiment was quadruplex. Inset indicates the $IC_{50}$ value of doxorubicin in various cell lines. (B) After treatment with vehicle or YMU1 for 72 h, cells were exposed to 0.1 μM of doxorubicin for 4 h and then seeded onto 100 mm-dish at 5,000 cells/dish. Following overnight culture, cells were refreshed with growth medium. After 14 days of culture, colonies were fixed, stained by crystal violet and counted. (C) HCT-116 p53−/− cells were subcutaneously implanted in the right flank of Balb/c nude mice (each experimental group n=8). Arrow indicated the time of stopping drug treatment. The tumor volume was estimated as described in Methods of the Invention section. (D) After 2 weeks recovered from treatment, mice were sacrificed for tumor weight measurement. Data represent mean±s.e.m; **, P<0.01 by a two-tailed Student's t-test. (E) $K_i$ 67 proliferation marker staining of tumor shown in left panel. Scale bar, 50 μm. (F) Model of doxorubicin sensitization by YMU1 in malignant cancer cells. Both R2/R1 and TMPK are recruited to the site of doxorubicin-induced double-strand breaks, where dATP, dGTP, dCTP, dTTP and dUTP are site-specific synthesized. Inhibition of TMPK decreases dTTP formation at DNA damage sites, causing futile DNA repair due to dUTP incorporation.

FIG. 17. Doxorubicin sensitization by YMU1 is through TMPK inhibition. After transfection with TMPK siRNA for 2 days, MDA-MB231 cells were treated with vehicle or YMU1 (2 μM) for 72 h prior to 0.1 μM of doxorubicin exposure and the cell viability assays were performed after incubating with fresh medium for 48 h (mean±s.d., n=3; each assay was in quadruplex). A proportion of cells were collected for Western blotting analysis.

FIG. 18. Reversal effect of doxorubicin sensitization with YMU1 treatment by overexpression of dUTPase. After 48 h recovery from doxorubicin exposure, MDA-M B231 cells were stained with Annexin V-PE for apoptosis analysis. Percentage of GFP cells positive in Annexin V-PE staining is shown (mean±s.d., n=3; *, P<0.05, two-tailed Student's t-test, >50 of GFP positive cells were counted in each experiment).

FIG. 19. No effect of YMU1 on dUTPase activity. 0.1 μg of purified GST-dUTPase protein was incubated with the indicated concentration of YMU1 for 10 min prior to action using dUTPase activity analysis.

FIG. 20. Verification of antibodies specificity. Cells were infected with lentiviral TMPK shRNA, dUTPase shRNA or transfected with R2 siRNA. After infection or transfection for 72 h, cells were harvested for WB analysis using indicated antibodies.

DETAILED DESCRIPTION OF THE INVENTION

Figure 1A:
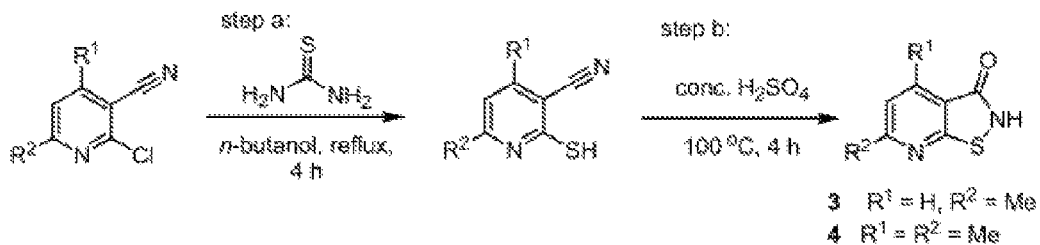
FIGS. 1A-1J. Synthesis of TMPK inhibitor derivative compounds of the present invention.

Unless otherwise defined, all technical terms used herein have the same meaning as commonly understood by one of ordinary skill in the art to which this invention belongs.

To facilitate understanding of the present application and for ease of reference, a number of terms and abbreviations as used herein are defined below.

As used herein, the terms "treating" and "treatment" are used to refer to administration or application of a therapeutic agent to a subject or performance of a procedure or modality on a subject for the purpose of obtaining a therapeutic benefit of a disease or health-related condition.

As used herein, the terms "preventing," "inhibiting," "reducing" or any variation of these terms, includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99% or more, or any range derivable therein, reduction of activity or symptoms, compared to normal.

As used herein, the terms "administered" and "delivered" are used to describe the process by which a composition of the present invention is administered or delivered to a subject, a target cell or are placed in direct juxtaposition with the target cell. The terms "administered" and "delivered" are used interchangeably.

As used herein, the terms "patient," "subject" and "individual" are used interchangeably herein, and mean a mammalian (e.g., human) subject to be treated and/or to obtain a biological sample from.

As used herein, the term "effective" means adequate to accomplish a desired, expected, or intended result. For example, an "effective amount" may be an amount of a compound sufficient to produce a therapeutic benefit.

As used herein, the terms "therapeutically effective" or "therapeutically beneficial" refers to anything that promotes or enhances the well-being of the subject with respect to the medical treatment of a condition. This includes, but is not limited to, a reduction in the onset, frequency, duration, or severity of the signs or symptoms of a disease.

As used herein, the term "therapeutically effective amount" is meant an amount of a composition as described herein effective to yield the desired therapeutic response.

As used herein, the terms "diagnostic," "diagnose" and "diagnosed" mean identifying the presence or nature of a pathologic condition.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used as described herein.

The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, the term "alkyl" (alone or in combination with another term(s)) refers to a saturated aliphatic hydrocarbon radical including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). Alkyl groups containing from 1 to 4 carbon atoms are referred to as lower alkyl groups. When said lower alkyl groups lack substituents, they are referred to as unsubstituted lower alkyl groups. More preferably, an alkyl group is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, or tert-butyl, and the like. The alkyl group may be substituted or unsubstituted. When substituted, the substituent group(s) is preferably one or more, more preferably one to three, even more preferably one or two substituent(s) independently selected from the group consisting of halo, hydroxy, unsubstituted lower alkoxy, aryl optionally substituted with one or more groups, preferably one, two or three groups which are independently of each other halo, hydroxy, unsubstituted lower alkyl or unsubstituted lower alkoxy groups, aryloxy optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 5- or 6-member heterocyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, mercapto, (unsubstituted lower alkyl)thio, arylthio optionally substituted with one or more groups, preferably one, two or three groups which are independently of each other halo, hydroxy, unsubstituted lower alkyl or alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)O—, and NR$_{13}$R$_{14}$, wherein R$_{13}$ and R$_{14}$ are independently selected from the group consisting of hydrogen, unsubstituted lower alkyl, trihalomethyl, cycloalkyl, heterocyclic and aryl optionally substituted with one or more, groups, preferably one, two or three groups which are independently of each other halo, hydroxy, unsubstituted lower alkyl or unsubstituted lower alkoxy groups.

Preferably, the alkyl group is substituted with one or two substituents independently selected from the group consisting of hydroxy, 5- or 6-member heterocyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, or —NR$_{13}$R$_{14}$, wherein R$_{13}$ and R$_{14}$ are independently selected from the group consisting of hydrogen and alkyl. Even more preferably the alkyl group is substituted with one or two substituents which are independently of each other hydroxy, dimethylamino, ethylamino, diethylamino, dipropylamino, pyrrolidino, piperidino, morpholino, piperazino, 4-lower alkylpiperazino, phenyl, imidazolyl, pyridinyl, pyridazinyl, pyrimidinyl, oxazolyl, triazinyl, and the like.

As used herein, the term "aromatic", "ar" or "aryl" (alone or in combination with another term(s)) refer to aromatic cyclic groups (for example 6 membered monocyclic, 10 membered bicyclic or 14 membered tricyclic ring systems) which contain 6 to about 14 carbon atoms. Exemplary aromatic groups include phenyl, naphthyl, biphenyl, indenyl, and anthracene.

As used herein, the term "halogen" (alone or in combination with another term(s)) refers to a fluorine substituent ("fluoro," which may be depicted as —F), chlorine substituent ("chloro," which may be depicted as —Cl), bromine substituent ("bromo," which may be depicted as —Br), or iodine substituent ("iodo," which may be depicted as —I).

As used herein, the term "cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system.

Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. When substituted, the substituent group(s) is preferably one or more, more preferably one or two substituents, independently selected from the group consisting of unsubstituted lower alkyl, trihaloalkyl, halo, hydroxy, unsubstituted lower alkoxy, aryl optionally substituted with one or more, preferably one or two groups independently of each other halo, hydroxy, unsubstituted lower alkyl or unsubstituted lower alkoxy groups, aryloxy optionally substituted with one or more, preferably one or two groups independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more, preferably one or two groups independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and nitrogen atoms of the group being optionally substituted with one or more, preferably one or two groups independently of each other halo, hydroxy, unsubstituted lower alkyl or unsubstituted lower alkoxy groups, 5- or 6-member heterocyclic group having from 1 to 3 heteroatoms selected from the group consisting of nitrogen, oxygen and sulfur, the carbon and nitrogen (if present) atoms in the group being optionally substituted with one or more, preferably one or two groups independently of each other halo, hydroxy, unsubstituted lower alkyl or unsubstituted lower alkoxy groups, mercapto, (unsubstituted lower alkyl)thio, arylthio optionally substituted with one or more, preferably one or two groups independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$ are as defined above.

As used herein, the term "alkenyl" (alone or in combination with another term(s)) refers to a lower alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

As used herein, the term "alkynyl" (alone or in combination with another term(s)) refers to a lower alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic (i.e., rings which share adjacent pairs of carbon atoms) groups of 1 to 12 carbon atoms having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O).sub.2-, —C(O)OR, RC(O)—, and —NR$_{13}$R$_{14}$, with R$_{13}$ and R$_{14}$ as defined above. Preferably, the aryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "heteroaryl" refers to a monocyclic or fused ring (i.e., rings which share an adjacent pair of atoms) group of 5 to 12 ring atoms containing one, two, or three ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more, more preferably one, two, or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O).sub.2-, —C(O)OR, RC(O)—, and —NR$_{13}$R$_{14}$, with R$_{13}$ and R$_{14}$ as defined above. Preferably, the heteroaryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "Heterocyclic" refers to a monocyclic or fused ring group having in the ring(s) of 5 to 9 ring atoms in which one or two ring atoms are heteroatoms selected from N, O, or S(O)n (where n is an integer from 0 to 2), the remaining ring atoms being C. The rings may also have one or more double bonds. However, the rings do not have a completely conjugated pi-electron system. Examples, without limitation, of unsubstituted heterocyclic groups are pyrrolidino, piperidino, piperazino, morpholino, thiomorpholino, homopiperazino, and the like. The heterocyclic ring may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O).sub.2-, —C(O)OR, RC(O)—, and —NR$_{13}$R$_{14}$, with R$_{13}$ and R$_{14}$ as defined above. Preferably, the heterocyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

Preferably, the heterocyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "Hydroxy" refers to an —OH group.

As used herein, the term "Alkoxy" refers to both an —O-(unsubstituted alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

As used herein, the term "Aryloxy" refers to both an —O-aryl and an O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

The terms "heterocycle", "heterocyclic" or "heterocyclo" (alone or in combination with another term(s)) refer to fully saturated (i.e., "heterocycloalkyl"), non-aromatic partially-saturated (i.e., "heterocycloalkenyl"), or heterocylic aromatic (i.e. "heteroaryl") ring structure, typically having 3 to about 20 carbon atoms, more typically having 3 to about 14 carbon atoms. For example, the heterocyclic group may a 4 to about 7 membered monocyclic ring systems, a 7 to about 11 membered bicyclic ring systems, or a 10 to about 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, thienyl (also known as "thiophenyl" and "thiofuranyl"), oxazolyl, isoxazolyl, thiazolyl, isbthiazolyl, thiodiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), pyrrolyl, pyrazolyl, imidazolyl, triazolyl, tetrazolyl, oxathiazolyl, oxatriazolyl (including 1,2,3,4-oxatriazolyl and 1,2,3,5-oxatriazolyl), pyridinyl, diazinyl (including pyridazinyl (also known as "1,2-diazinyl"), pyrimidinyl (also known as "1,3-diazinyl"), and pyrazinyl (also known as "1,4-diazinyl")), triazinyl (including s-triazinyl (also known as "1,3,5-triazinyl"), as-triazinyl (also known 1,2,4-triazinyl), and v-triazinyl (also known as "1,2,3-triazinyl")), oxathiazinyl (including 1,2,5-oxathiazinyl and 1,2,6-oxathiazinyl), oxepinyl, thiepinyl, dihydrofuranyl, tetrahydrofuranyl, dihydrothienyl (also known as "dihydrothiophenyl"), tetrahydrothienyl (also known as "tetrahydrothiophenyl"), isopyrrolyl, pyrrolinyl, pyrrolidinyl, isoimidazolyl, imidazolinyl, imidazolidinyl, pyrazolinyl, pyrazolidinyl, dithiolyl, oxathiolyl, oxathiolanyl, oxazolidinyl, isoxazolidinyl, thiazolinyl, isothiazolinyl, thiazolidinyl, isothiazolidinyl, dioxazolyl (including 1,2,3-dioxazolyl, 1,2,4-dioxazolyl, 1,3,2-dioxazolyl, and 1,3,4-dioxazolyl), pyranyl (including 1,2-pyranyl and 1,4-pyranyl), dihydropyranyl, tetrahydropyranyl, piperidinyl, piperazinyl, oxazinyl (including 1,2,3-oxazinyl, 1,3,2-oxazinyl, 1,3,6-oxazinyl (also known as "pentoxazolyi"), 1,2,6-oxazinyl, and 1,4-oxazinyl), isoxazinyl (including o-isoxazinyl and p-isoxazinyl), oxadiazinyl (including 1,4,2-oxadiazinyl and 1,3,5,2-oxadiazinyl), morpholinyl, azepinyl, and diazepinyl.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

A heterocyclyl alternatively may be from 2 to 5 (more typically from 2 or 3) rings fused together, such as, for example, indolizinyl, pyranopyrrolyl, purinyl, imidazopyrazinyl, imidazolopyridazyl, pyridopyridinyl (including pyrido[3,4-b]-pyridinyl, pyrido[3,2-b]-pyridinyl, pyrido[4,3-b]-pyridinyl, and naphthyridinyl), pteridinyl, pyridazinotetrazinyl, pyrazinotetrazinyl, pyrimidinotetrazinyl, pyrindinyl, pyrazolopyrimidinyl, pyrazolopyrazinyl, pyrazolopyridazyl, or 4H-quinolizinyl. In some embodiments, the multi-ring heterocyclyls are indolizinyl, pyranopyrrolyl, purinyl, pyridopyridinyl, pyrindinyl, and 4H-quinolizinyl.

Exemplary bicyclic heterocyclic groups include indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Other examples of fused-ring heterocyclyls include benzo-fused heterocyclyls, such as, for example, benzofuranyl (also known as "coumaronyl"), isobenzofuranyl, benzoxazolyl, benzoisoxazolyl (also known as "indoxazinyl"), anthranilyl, benzothienyl (also known as "benzothiophenyl," "thionaphthenyl," and "benzothiofuranyl"), isobenzothienyl (also known as "isobenzothiophenyl," "isothionaphthenyl," and "isobenzothiofuranyl"), benzothiazolyl, benzoisothiazolyl, benzothiadiazolyl, benzoxadiazolyl, indolyl, isoindazolyl (also known as "benzpyrazolyl"), benzoimidazolyl, benzotriazolyl, benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzoimidazothiazolyl, carbazolyl, acridinyl, isoindolyl, indoleninyl (also known as "pseudoindolyl"), benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, benzoxazinyl (including 1,3,2-benzoxazinyl, 1,4,2-benzoxazinyl, 2,3,1-benzoxazinyl, and 3,1,4-benzoxazinyl), benzoisoxazinyl (including 1,2-benzisoxazinyl and 1,4-benzisoxazinyl), benzoxadiazinyl, and xanthenyl. In some embodiments, the benzo-fused heterocyclyls are benzofuranyl, isobenzofuranyl, benzoxazolyl, benzoisoxazolyl, anthranilyl, benzothienyl, isobenzothienyl, benzothiazolyl, benzothiadiazolyl, benzoxadiazolyl, indolyl, isoindazolyl, benzoimidazolyl, benzotriazolyl, benzazinyl, phthalazinyl, quinoxalinyl, benzodiazinyl, carbazolyl, acridinyl, isoindolyl, indoleninyl, benzodioxolyl, chromanyl, isochromanyl, thiochromanyl, benzodioxanyl, tetrahydroisoquinolinyl, benzoxazinyl, benzoisoxazinyl, and xanthenyl.

As used herein, the term "heteroaryl" (alone or in combination with another term(s)) refers to an aromatic heterocyclyl typically containing from 5 to 14 ring atoms. A heteroaryl may be a single ring or multiple (typically 2 or 3) fused rings. Such moieties include, for example, 5-membered rings such as furanyl, thienyl, oxazolyl, isoxazolyl, thiazolyl, isothiazolyl, thiodiazolyl, oxadiazolyl, pyrrolyl, pyrazolyl, imidazolyl, triazolyl, tetrazolyl, oxathiazolyl, and oxatriazolyl; 6-membered rings such as pyridinyl, pyrazinyl, pyrimidinyl, pyridazinyl, triazinyl, and oxathiazinyl; 7-membered rings such as oxepinyl and thiepinyl; 6/5-membered fused-ring systems such as benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, and imidazolopyridazyl; and 6/6-membered fused-ring systems such as quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, benzoimidazothiazolyl, carbazolyl, and acridinyl. In some embodiments, the 5-membered rings include furanyl, thienyl, oxazolyl, isoxazolyl, thiazolyl, isothiazolyl, oxadiazolyl, pyrazolyl, and imidazolyl; the 6-membered rings include pyridinyl, pyrazinyl, pyrimidinyl, pyridazinyl, and triazinyl; the 6/5-membered fused-ring systems include benzoxazolyl, benzoisoxazolyl, anthranilyl, benzothienyl, isobenzothienyl, and purinyl; and the 6/6-membered fused-ring systems include quinolinyl, isoquinolinyl, and benzodiazinyl.

Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, pyridazinyl, triazolyl, triazinyl, and the like.

As used herein, the term "hydrogen" (alone or in combination with another term(s)) refers to a hydrogen substituent and may be depicted as —H.

As used herein, the term "hydroxy" (alone or in combination with another term(s)) refers —OH.

As used herein, the term "nitro" (alone or in combination with another term(s)) refers to —NO$_2$.

As used herein, the term "substitution" refers to a compound having a substituent comprising at least one carbon, nitrogen, oxygen, or sulfur atom that is bonded to one or more hydrogen atoms. If a substituent is described as being "substituted," a non-hydrogen substituent is in the place of a hydrogen on a carbon, nitrogen, oxygen, or sulfur of the substituent. Thus, for example, a substituted alkyl substituent is an alkyl substituent wherein at least one non-hydrogen substituent is in the place of a hydrogen on the alkyl substituent. To illustrate, monofluoroalkyl is alkyl substituted with a fluoro, and difluoroalkyl is alkyl substituted with two fluoros.

It should be recognized that if there are more than one substitutions on a substituent, each non-hydrogen substituent may be identical or different (unless otherwise stated).

As used herein, the terms "contacted" and "exposed" when applied to a cell, are used to describe the process by which a compound of the present invention is administered or delivered to a target cell or are placed in direct juxtaposition with the target cell. The terms "administered" and "delivered" are used interchangeably with "contacted" and "exposed".

If a substituent is described as being "optionally substituted," the substituent is either (1) substituted, or (2) not substituted. When the members of a group of substituents are described generally as being optionally substituted, any atom capable of substitution in each member of such group may be (1) substituted, or (2) not substituted. Such a characterization contemplates that some members of the group are not substitutable. Atoms capable of substitution include, for example, carbon bonded to at least one hydrogen, oxygen bonded to at least one hydrogen, sulfur bonded to at least one hydrogen, or nitrogen bonded to at least one hydrogen. On the other hand, hydrogen alone, halogen, oxo, and cyano do not fall within the definition of being capable of substitution.

Although methods and compositions similar or equivalent to those described herein can be used in the practice or testing of the present invention, suitable methods and compositions are described below.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The particular embodiments discussed below are illustrative only and not intended to be limiting.

TMPK and TMPK Inhibitors

The present invention is directed to novel compositions and therapeutics comprising TMPK inhibitors and methods of use in treating or preventing cancers. Specifically, the present invention provides that thymidylate kinase (TMPK) is important for dTDP formation, while dADP, dGDP, dCDP and dUDP can be directly produced in reactions catalyzed by ribonucleotide reductase (RNR). The present invention reports TMPK and RNR binding at DNA damage-site and that intervention of the function of TMPK affects repair of DNA double-strand breaks by causing dUTP incorporation in tumor cells. These dUTP-mediated lesions can be prevented by disrupting RNR damage-site recruitment or decreasing the expression level of R2 subunit of RNR in tumor cells, suggesting the contribution of elevated function of RNR at DNA damage-site to dUTP incorporation.

Using RNA interference, the present invention provides that TMPK knockdown significantly increases the sensitivity of HCT-116 colon cancer cells to doxorubicin, a topoisomerase II inhibitor that induces DNA (DSBs), regardless of p53 status (Hu and Chang, 2008). In comparison, TS knockdown has a rather limiting effect in sensitizing p53-deficient cells to doxorubicin because of the complementation of TK-mediated dTMP formation. Importantly, the present invention provides that TMPK knockdown does not, on its own, activate DNA damage responses. It thus functions in a way that is quite distinct from that of anti-metabolites used in conventional anti-cancer therapies, which directly induce genotoxicity (Garg et al., 2010).

Unlike blocking RNR which results in replication stress with DNA damage response (Helleday et al., 2008), TMPK knockdown cells are still capable of proliferating and are viable (Hu and Chang, 2008). Given the essential function of TMPK in dTDP formation, this may be because human tumor cells might contain TMPK isoform. However, it is hard to understand why TMPK knockdown, like blocking RNR, profoundly affects DNA repair in tumor cells. A recent report demonstrates RNR recruitment to DNA damage sites as a result of an interaction with Tip60 via the C-terminal region of the R1 subunit (Niida et al., 2010a). Disruption of RNR recruitment to DNA damage site affects DSBs repair in G1 but not S phase cells, which is attributed to the low levels of dNTP pools in G0/G1 phase, making site-specific production of dNTPs by RNR critical for DNA repair in these cells (Hakansson et al., 2006). The present invention illustrates DNA damage-site association of TMPK, and that high expression level of R2 of RNR at DNA damage-site without TMPK functional coupling can lead to toxic repair due to dUTP incorporation in proliferating tumor cells. Thus, the present invention provides that the context of R2 elevation makes TMPK as the Achilles heel in tumor for doxorubicin sensitization.

The present invention provides the identification of novel inhibitors of TMPK, which sensitizes tumor cells to doxorubicin in vitro and in vivo and did not produce genotoxic effects in cells or mice. Thus, the novel inhibitors described in the present invention provide a new opportunity in developing mild anti-cancer therapies that can prime tumor cells to sublethal doses of doxorubicin treatment to achieve lethality while having minimal side effects in normal cycling cells.

Accordingly, the present invention provides novel TMPK inhibitors that are useful in the treatment or prevention of cancer.

In one embodiment of the present invention, a composition for inhibiting thymidylate kinase (TMPK) comprising a therapeutically effective amount of formula (I) is provided:

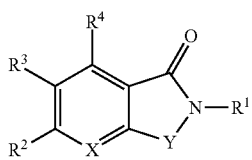

(I)

wherein
X=CH or N;
Y=S, SO$_2$, O, C=O, or NR$^5$, wherein R$^5$ is a substituent selected from the group consisting of hydrogen, a straight, branched or cyclic alkyl group, aralkyl, heteroaralkyl, heteroarakenyl, aryl, heteroaryl, optionally substituted with one or more substituents such as halogen, alkyl, hydroxyl, alkoxy, amino, nitro, cyano and carbonyl;
R$^1$=(CH$_2$)$_n$COR$^6$, wherein n is 0, 1, 2, or 3; and
R$^2$, R$^3$, R$^4$ and R$^6$ are substituents independently selected from the group consisting of hydrogen, a straight, branched or cyclic alkyl group, a straight, branched or cyclic alkenyl group, a straight, branched or cyclic alkoxyl group, fluoroalkyl, perfluoroalkyl, aralkyl, arakenyl, arakynyl, heteroaralkyl, heteroarakenyl, heteroarakynyl, aryl, heteroaryl, optionally substituted with one or more substituents such as halogen, alkyl, hydroxyl, alkoxy, amino, nitro, cyano and carbonyl;
or a pharmaceutically acceptable salt, hydrate or solvate thereof.

In some embodiments of the present invention, the composition comprises at least one of the following structures:

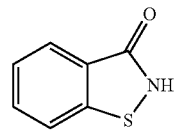

1

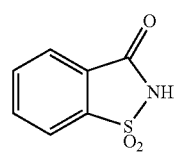

2

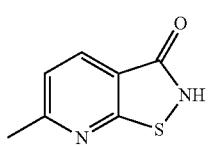

3

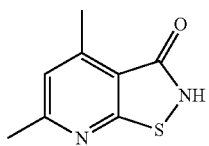

4

In some embodiments of the present invention, the composition comprises the following structure:

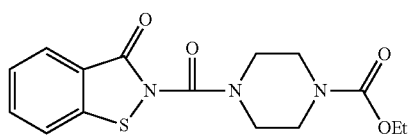

5

In some embodiments of the present invention, the composition comprises at least one of the following structures:

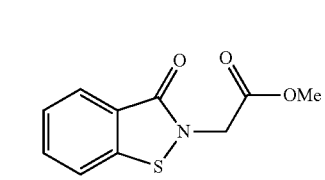

6

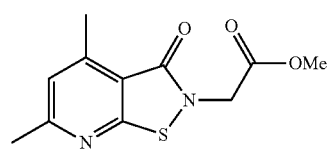

7

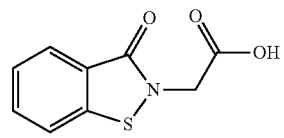

8

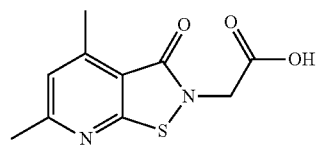
9

In some embodiments of the present invention, the composition comprises at least one of the following structures:

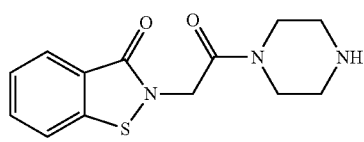
10

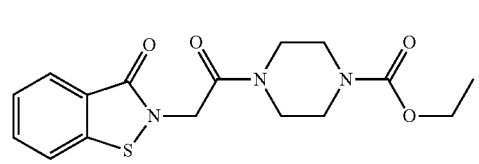
11

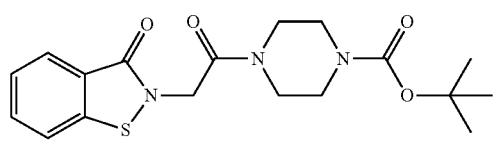
12

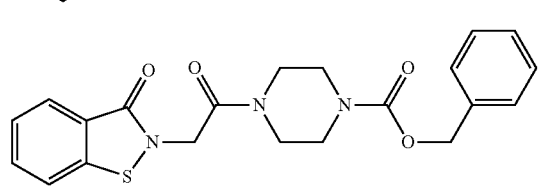
13

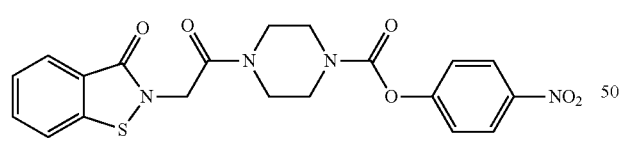
14

In some embodiments of the present invention, the composition comprises the following structure:

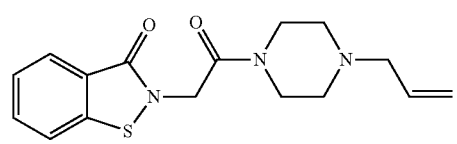
15

In some embodiments of the present invention, the composition comprises at least one of the following structures:

16

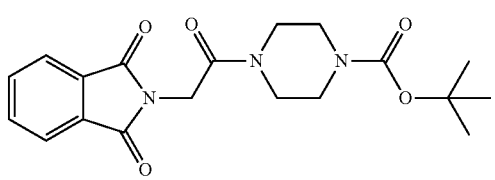
17

In some embodiments of the present invention, the composition comprises the following structure:

18

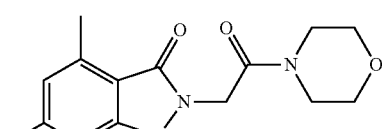

In some embodiments of the present invention, the composition comprises at least one of the following structures:

19

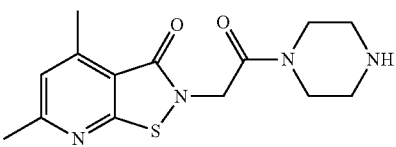
20

In some embodiments of the present invention, the composition comprises at least one of the following structures:

21 (YMU1)

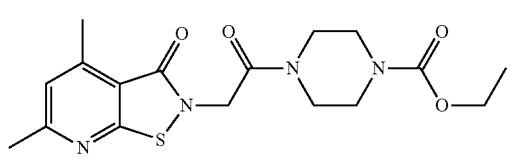

In some embodiments of the present invention, the composition comprises the following structure:

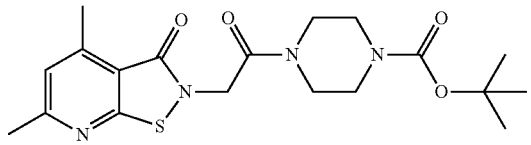
22

In some embodiments of the present invention, the composition comprises the following structure:

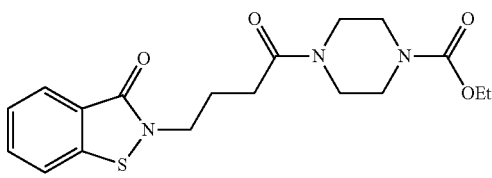
23

In some embodiments of the present invention, the composition comprises the following structure:

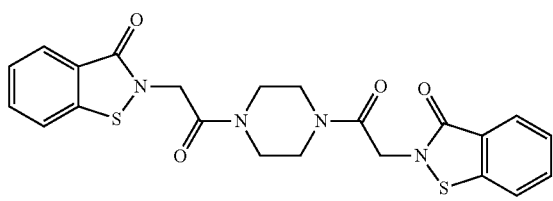
24

In some embodiments of the present invention, the composition comprises at least one of the following structures:

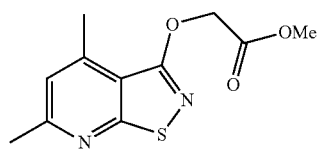
25

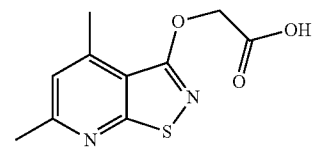
26

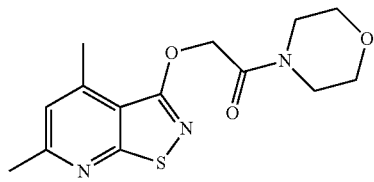
27

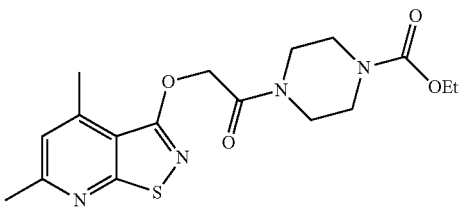
28

In some embodiments, the compositions of the present invention are capable of inhibiting TMPK activity. In other embodiments, the compositions of the present invention are capable of inhibiting cellular dTTP levels. In some embodiments, the compositions of the present invention are capable of inhibiting tumor growth, DNA damage checkpoint, DNA mismatch repair, nucleotide excision repair, double-strand break repair, DNA helicase function, signaling, cell cycle control or apoptosis.

In particular, the double-strand break repair may be associated with radiation therapy, chemotherapy or immunomodulatory therapy. In some cases, the chemotherapy involves treatment with doxorubicin.

In some embodiments, the compositions of the present invention selectively target toxicity to cancer cells with DNA lesions.

In other embodiments, the compositions of the present invention are capable of sensitizing cancer cells to radiation therapy, chemotherapy or immunomodulatory therapy. In some embodiments, the chemotherapy involves treatment with doxorubicin.

In some embodiments, the compositions of the present invention do not result in genotoxic side effects.

In some embodiments, the compositions of the present invention exhibit an $IC_{50}$ value of about 10 μM or less. In some embodiments, they exhibit an $IC_{50}$ value of about 5 μM or less. In some embodiments, the compositions exhibit an $IC_{50}$ value of about 1 μM or less. In some embodiments, the compounds exhibit an $IC_{50}$ value of about 0.5 μM or less. In still other embodiments, the compositions exhibit an $IC_{50}$ value of about 0.25 μM or less. In other embodiments, the compositions exhibit an $IC_{50}$ value of about 0.1 μM or less.

Figure 1B:
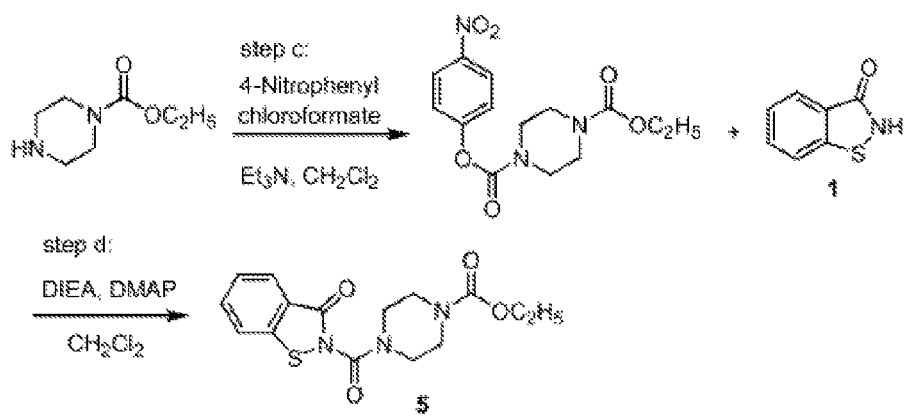
Figure 1C:
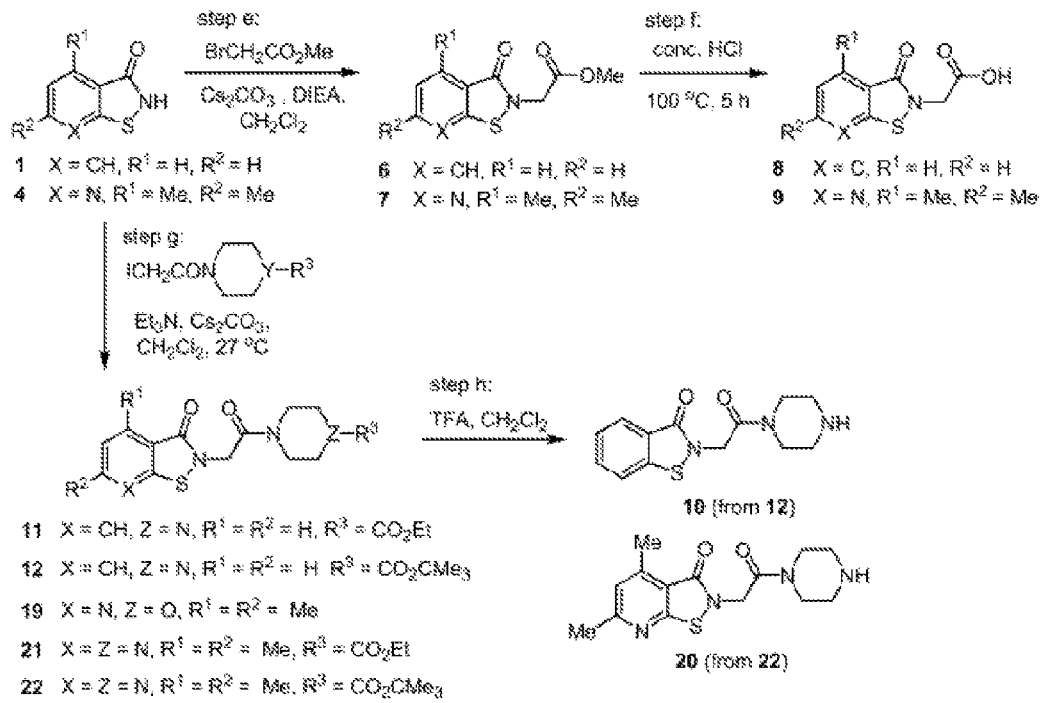
Figure 1D:
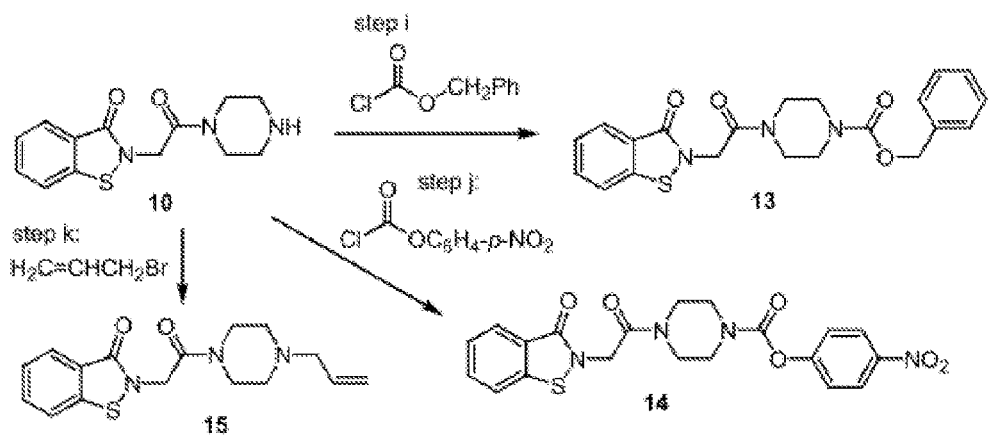
Figure 1E:
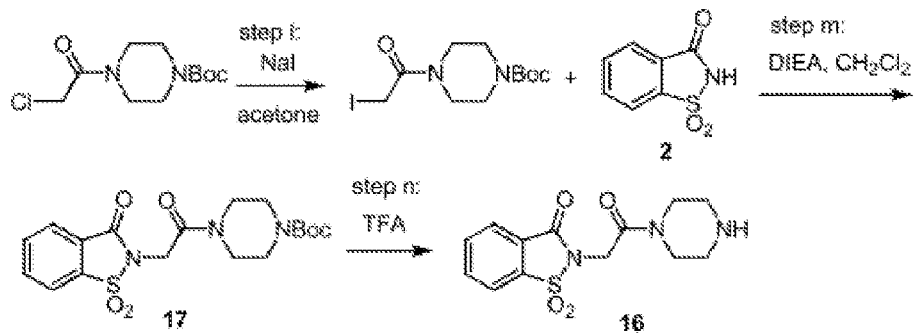
Figure 1F:
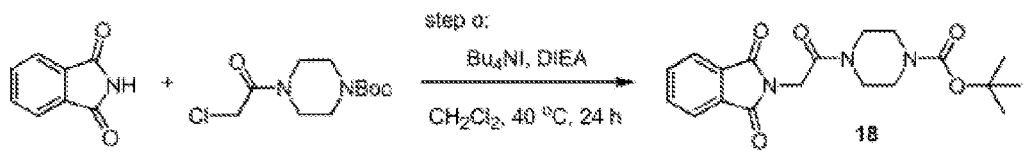
Figure 1G:
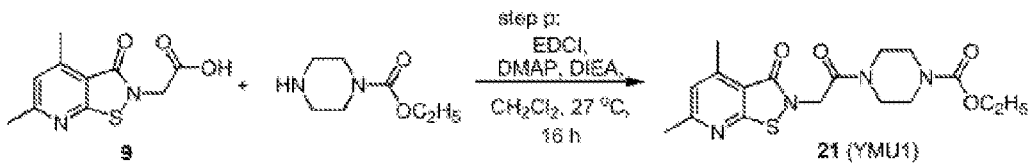
Figure 1H:
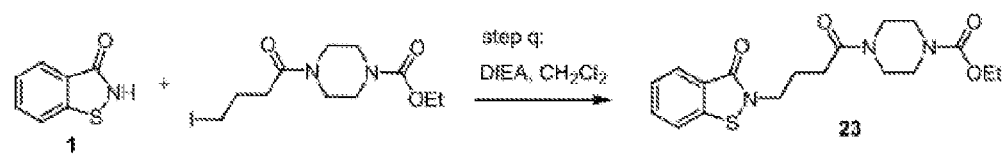
Figure 1I:
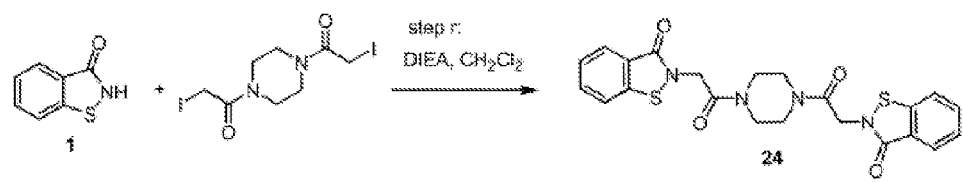
Figure 1J:
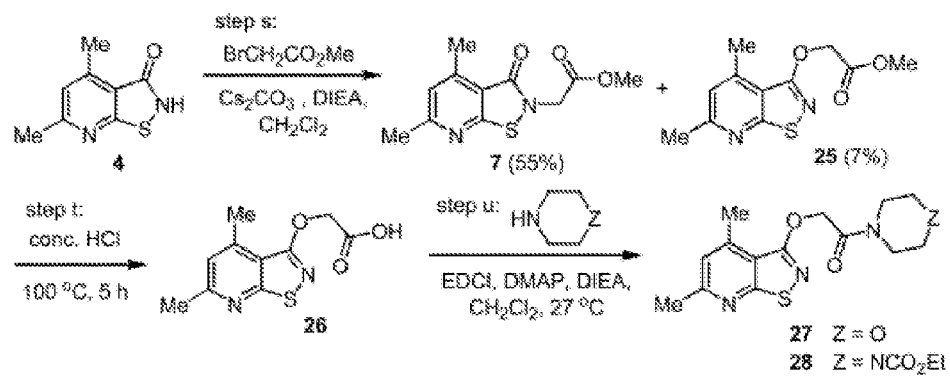

The present invention also provides the methods for manufacturing the compositions, in particular the novel TMPK inhibitor derivative compounds as illustrated in FIGS. 1A-1J, comprising the steps of:

(a) treating 2-chloro-6-methylnicotinonitrile (or 2-chloro-4,6-dimethylnicotinonitrile) with thiourea to give intermediate compound of 2-mercapto-6-methylnicotinonitrile (or 2-mercapto-4,6-dimethylnicotinonitrile);

(b) treating 2-mercapto-6-methylnicotinonitrile and 2-mercapto-4,6-dimethylnicotinonitrile in concentrated $H_2SO_4$ at 100° C. to give pyridinoisothiazolone compounds 3 ($R^1$=H, $R^2$=Me) and 4 ($R^1$=$R^2$=Me), respectively;

(c) treating ethyl piperazine-1-carboxylate with 4-nitrophenyl chloroformate and triethylamine ($Et_3N$) to give an intermediate compound of activated carbamate;

(d) treating the activated carbamate with benzothiazolone (compound 1) in 4-dimethylaminopyridine (DMAP) and diisopropylethylamine (DIEA) to give compound 5;

(e) treating benzothiazolone 1 (or pyridinothiazolone 4) with methyl 2-bromoacetate in the presence of DIEA and cesium carbonate ($Cs_2CO_3$) to give compounds 6 and 7, respectively;

(f) treating compounds 6 and 7 in concentrated hydrochloric acid at 100° C. to give compounds 8 and 9, respectively;

(g) treating benzothiazolone 1 (or pyridinothiazolone 4) with appropriate halides in the presence of $Et_3N$ and $Cs_2CO_3$ to give compounds 11, 12, 19, 21 and 22;

(h) treating tert-butyl carbamate 12 and 22 with trifluoroacetic acid (TFA) to give compounds 10 and 20, respectively;

(i) treating compound 10 with benzyl chloroformate in the presence of DIEA to give compound 13;

(j) treating compound 10 with 4-nitrophenyl chloroformate in the presence of DMAP to give compound 14;

(k) treating compound 10 with allyl bromide in the presence of DIEA to give compound 15;

(l) treating tert-butyl 4-(2-chloroacetyl)piperazine-1-carboxylate with sodium iodide in acetone to give the corresponding iodo compound, tert-butyl 4-(2-iodoacetyl)piperazine-1-carboxylate;

(m) treating saccharin (compound 2) with the above-prepared iodo compound in the presence of DIEA to give compound 17;

(n) treating tert-butyl carbamate 17 with TFA to give compound 16;

(o) treating phthalimide with tert-butyl 4-(2-chloroacetyl)piperazine-1-carboxylate in the presence of tetrabutylammonium iodide (TBAI) and DIEA to give compound 18;

(p) treating compound 9 with ethyl piperazine-1-carboxylate in the presence of 1-ethyl-3-(3-dimethylaminopropyl)carbodiimide (EDCI), DMAP and DIEA to give compound 21 (YMU1);

(q) treating benzothiazolone 1 with ethyl 4-(4-iodobutanoyl)piperazine-1-carboxylate in the presence of DIEA to give compound 23;

(r) treating benzothiazolone 1 with 1,1'-(piperazine-1,4-diyl)-bis(2-iodoethanone) in the presence of DIEA to give compound 24;

(s) treating pyridinothiazolone 4 with methyl 2-bromoacetate in the presence of DIEA and $Cs_2CO_3$ to give N-alkylation compound 7 and O-alkylation compound 25;

(t) treating compound 25 in concentrated hydrochloric acid at 100° C. to give compound 26;

(u) treating compound 26 with morpholine (or ethyl piperazine-1-carboxylate) in the presence of EDCI, DMAP and DIEA to give compounds 27 and 28, respectively.

As illustrated in the Examples section, the present application provides new insights into the functional requirement of TMPK for DNA repair in tumor cells. This requirement specifically involves elevation of R2 expression and RNR recruitment to DNA damage-site. The data presented herein suggests that RNR at DNA damage-site may give rise to site-specific dUTP production. Theoretically, the action of dUTPase to dUMP formation and TS-mediated reaction that converts dUMP to dTMP would limit the amount of cellular dUTP. However, blocking TMPK function causes dUTP incorporation in DNA repair dependent on RNR damage-site recruitment in tumor cells, revealing the physiological complication of site-specific production of dUTP from RNR.

Accordingly, the present application provides that blocking TMPK reduces the rate of dTTP formation at the DNA damage-site, which in turn increases the probability of dUTP incorporation in the repair process, leading to persistent lesions. This is because more than 10,000 dNTPs incorporate in repairing each DSB and that the elevated function of RNR in tumor cells let dUTP prevail at the DNA damage site, making toxic repair. Since tumor cells contain elevated function of RNR, blocking of TMPK function specifically sensitize tumor cells to doxorubicin.

Interestingly, the expression levels of R2 and dUTPase are elevated concurrently in MDA-MB231 and MCF-7 cells. Presumably, this cellular context protects DNA repair from dUTP incorporation. Therefore, these tumor cells are capable of repairing lesions induced by low-dose of doxorubicin exposure. In this cellular context, it is until TMPK knockdown that dUTP incorporation takes place in DNA repair. Expression of R2 subunit of RNR and dUTPase is cell-cycle regulated, peaking in the S and G2/M phases (Ladner and Caradonna, 1997; Nordlund and Reichard, 2006). It is well established that malignant cells have cell cycle checkpoint defects (Kastan and Bartek, 2004). Therefore, these tumor cells during recovery from DNA damage had more population distribution in S and G2/M phase. In contrast, the S phase population was decreased in normal cycling H184B5F5/M10 cells during recovery from DNA damage probably due to the presence of intact checkpoint. As a result, these normal cycling cells expressed even less amount R2, which might further limit dUDP formation. However, it should be mentioned that normal cycling cells contain appreciated level of p53R2 subunit, which is still capable of forming functional RNR at DNA damage site. So, why DNA repair is unaffected by TMPK knockdown in normal cycling cells? One plausible explanation is that R2 has a 4.7-fold higher binding affinity for R1 than p53R2 (Shao et al., 2004). It is possible that the low affinity of p53R2 for R1 subunit makes RNR function less efficient and minimizes the site-specific production of dUTP in normal cycling cells, thereby dispensing the functional requirement of TMPK at DNA damage site for repair. Indeed, enforced elevation of R2 by overexpression renders normal cycling cells sensitive to TMPK knockdown in having persistent DNA damage after low dose of doxorubicin exposure, supporting our notion in dUTP production by elevation of RNR function. Expression of R2 and p53R2 has been found up-regulated in many types of cancer cells in patients (Jensen et al., 1994; Okumura et al., 2005; Yanamoto et al., 2003; Zhang et al., 2009). Transgenic mice overexpressing R2 or p53R2 in the lungs generate tumors (Xu et al., 2008). Whether side-effect of dUTP formation of RNR at DNA damage site is related to their oncogenic potential remains investigated. Nevertheless, it is noteworthy that p53R2 prognoses better survival of colorectal cancer while the R2 level correlates with poor outcome (Liu et al., 2011). Expression of RNR mutant defective in dATP feedback inhibition in yeast causes elevation of dNTP, accompanied by inhibition of cell cycle progression and the DNA damage checkpoint (Chabes and Stillman, 2007). Whether this phenomenon involves dUTP formation is also worthy of investigation.

The present findings rationalize that the context of R2 elevation makes TMPK as Achilles heel in tumor for doxorubicin sensitization. To achieve this, a new TMPK inhibitor, YMU1, was identified. The present application provides that YMU1 did not produce genotoxic effects in cells or mice. 5-FU and 5-FdUrd, the most commonly used chemotherapeutic agents, inhibit TS, which converts dUMP to dTMP in the de novo synthesis pathway, and further impair cell function through erroneous nucleotide misincorporation into RNA and DNA (Longley et al., 2003). Although TS inhibitors and other nucleotide metabolite blockers have also been used as chemosensitizers (Garg et al., 2010), it should be emphasized that these anti-cancer agents are toxic to genomic DNA in normal cycling cells. Their therapeutic effect stems solely from their ability to cause extensive DNA damage, so they produce non-specific toxicity. We propose that the therapeutic advantage of TMPK inhibitors of the present invention over these conventional compounds is their specific toxicity to malignant cells with DNA lesions.

Therapeutic Uses

The present invention provides a method of sensitizing cancer cells to radiation therapy, chemotherapy or immunomodulatory therapy comprising exposing the cancer cells to an effective amount of a TMPK inhibitor composition of the present invention. In some embodiments, the TMPK inhibitor composition of the present invention selectively target toxicity to cancer cells with DNA lesions. In some embodiments, the TMPK inhibitor composition of the present invention does not result in genotoxic side effects.

The present invention also provides a method for sensitizing cancer cells to the therapeutic effects of radiation therapy, chemotherapy or immunomodulatory therapy comprising exposing the cancer cells to an effective amount of an agent that inhibits TMPK activity. In some embodiments, the agent is a TMPK inhibitor composition of the present invention.

The present invention also provides a method of preventing double-strand break repair of cancer cells comprising exposing the cancer cells to an effective amount of a TMPK inhibitor composition of the present invention.

The present invention also provides a method of selectively targeting toxicity to cancer cells with DNA lesions comprising exposing the cancer cells to an effective amount of a TMPK inhibitor composition of the present invention.

In some embodiments, the cancer cell is selected from the group consisting of a breast cancer cell, a hepatoma cell, a colorectal cancer cell, pancreatic carcinoma cell, an esophageal carcinoma cell, a bladder cancer cell, an ovarian cancer cell, a skin cancer cell, a liver carcinoma cell, a gastric cancer cell, a prostate cancer cell, a colon cancer cell, a lung cancer cell, a rectal cancer cell, a renal cancer cell, a thyroid cancer cell, a brain cancer cell, melanoma, sarcoma, leukemia, a bone cancer cell and endometrial cancer cell.

In some embodiments, the present invention provides that the cancer cells are further exposed to at least one additional therapeutic agent selected from the group consisting of anti-cancer agents, antiviral agents, anti-inflammatory agents and immunosuppressive agents.

Anti-cancer agents contemplated within the present invention include, but are not limited to, microtubule interference agents, topoisomerase inhibitors, alkylating agents, thymidylate synthase inhibitors, anti-metabolites, pyrimidine antagonists, purine antagonists, ribonucleotide reductase inhibitors, and kinase inhibitors. In some embodiments, microtubule interference agents are those agents which induce disorganized microtubule formation, disrupting mitosis and DNA synthesis and include the taxanes, for example, paclitaxel and docetaxel; vinca alkyloids such as vinblastine, vincristine and vindesine. In some embodiments, topoisomerase inhibitors which act by breaking DNA, include two types, topoisomerase I and topoisomerase II inhibitors. Topoisomerase I inhibitors include but are not limited to irinotecan (CPT-11). Topoisomerase II inhibitors include, e.g., doxorubicin and epirubicin. Other toposiomerase inhibitors useful in the present invention include but are not limited to etoposide, teniposide, idarubicin and daunorubicin. In some embodiments, alkylating agents which act by damaging DNA, such as chlorambucil, melphalan, cyclophosphamide, ifosfamide, temozolomide, thiotepa, mitomycin C, busulfan, carmustine (BCNU) and lomustine (CCNU) have been shown to be useful chemotherapy agents. The alkylating agents also include the platins such as carboplatin and cisplatin which have been shown to be useful chemotherapy agents, even though they are not alkylators, but rather act by covalently bonding DNA. In some embodiments, thymidylate synthase inhibitors, which interfere with transcription by metabolizing to false bases of DNA and RNA, include, e.g., 5-fluorouracil and capecitabine. In some embodiments, anti-metabolites such as folate antagonists, methotrexate and trimetrexate have been found to be useful as chemotherapeutic agents. In some embodiments, pyrimidine antagonists such as fluorouracil, fluorodeoxyuridine and azacytidine have been found to be useful as chemotherapeutic agents. In some embodiments, purine antagonists have been found to be useful as chemotherapeutic agents and include agents such as mercaptopurine, thioguanine and pentostatin. Sugar modified analogs also useful as chemotherapeutic agents include cytarabine and fludarabine. In some embodiments, ribonucleotide reductase inhibitors have been found to be useful as chemotherapeutic agents and include agents such as hydroxyurea.

The present invention also provides a method of treating or preventing cancer in a subject in need thereof, comprising administering to said subject a therapeutically effective amount of a TMPK inhibitor derivative compound of the present invention. In some embodiments, the TMPK inhibitor derivative compounds of the present invention selectively target toxicity to cancer cells with DNA lesions. In some embodiments, the TMPK inhibitor derivative compounds of the present invention do not result in genotoxic side effects.

In some embodiments, the cancer is selected from the group consisting of breast cancer, hepatoma, colorectal cancer, pancreatic carcinoma, esophageal carcinoma, bladder cancer, ovarian cancer, skin cancer, liver carcinoma, gastric cancer, prostate cancer, colon cancer, lung cancer, rectal cancer, renal cancer, thyroid cancer, brain cancer, melanoma, sarcoma, leukemia, bone cancer and endometrial cancer.

Administration and Pharmaceutical Compositions

The claimed methods involve administration of a TMPK inhibitor composition of the present invention to a subject, either alone or in combination with an additional therapy such as radiation therapy, chemotherapy or immunomodulatory therapy.

Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compositions of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compositions can be formulated by combining the active compounds with pharmaceutically acceptable carriers well known in the art. Such carriers enable the compositions of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

For administration by inhalation, the compositions for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the composition and a suitable powder base such as lactose or starch.

The compositions may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

In addition to the formulations described previously, the compositions may also be formulated as depot preparations. Such long acting formulations may be administered by implantation (for example, subcutaneously or intramuscularly) or by intramuscular injection. A compositions of this invention may be formulated for this route of administration with suitable polymeric or hydrophobic materials (for instance, in an emulsion with a pharamcologically acceptable oil), with ion exchange resins, or as a sparingly soluble derivative such as, without limitation, a sparingly soluble salt.

Alternatively, other delivery systems for hydrophobic pharmaceutical compositions may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compositions may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an amount sufficient to achieve the intended purpose, e.g., treatment of cancer patients.

More specifically, a "therapeutically effective amount" means an amount of compound effective to prevent, alleviate or ameliorate symptoms of cancer or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of TMPK). Such information can then be used to more accurately determine useful doses in humans.

Toxicity and therapeutic efficacy of the compositions described herein can be determined by standard pharmaceutical procedures in cell cultures or experimental animals, e.g., by determining the $IC_{50}$ and the $LD_{50}$, wherein the $LD_{50}$ is the concentration of test compound which achieves a half-maximal inhibition of lethality, for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition.

Dosage amount and interval may be adjusted individually to provide plasma levels of the active species which are sufficient to maintain the intended modulating effect. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

The amount of a composition administered will, of course, be dependent on the subject being treated, the severity of the affliction, the manner of administration, the judgment of the prescribing physician, etc.

Accordingly, the present invention provides that the TMPK inhibitor compositions may be administered once daily for 3 consecutive days. In some embodiments, the present invention provides that the TMPK inhibitor compositions may be administered one to two times per day. In other embodiments, the present invention provides that the TMPK inhibitor compositions may be administered at a dose of about 5 mg/kg to about 30 mg/kg.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

The present invention is further illustrated by the following specific examples. The examples are provided for illustration only and should not be construed as limiting the scope of the invention in any way.

EXAMPLES

Example 1

TMPK is Important in Repair of Double-Stand Breaks by Preventing dUTP Incorporation To assess the role of TMPK in DSBs repair, we depleted TMPK expression by siRNA interference and performed HR analysis in U2OS cells harboring DR-GFP reporter (Pierce et al., 1999). With I-SceI endonuclease expression, HR repair takes place to generate intact GFP, giving fluorescence readout. By flow cytometry analysis, TMPK knockdown significantly reduced the HR repair efficiency, monitored by GFP positive fraction (FIG. 2A). We also tested the effect of TMPK knockdown on repairing doxorubicin-induced DNA lesions in MDA-MB231 breast cancer cells. The control and TMPK knockdown cells were treated with low-dose (0.1 μM) of doxorubicin exposure for 4 h and then washed thoroughly with growth medium for refreshment. Initially, the extent of DNA lesions, as indicated by γH2AX foci staining (Mah et al., 2010), was similar in these cells (FIG. 2B). After recovery for 24 h, doxorubicin-induced DNA lesions diminished in control cells, indicating cells capable of repairing the level of DNA damage induced by low-dose of doxorubicin exposure. In contrast, γH2AX foci persisted in TMPK knockdown cells. As a consequence, TMPK knockdown markedly reduced cell growth with doxorubicin exposure (FIG. 3). Thus, TMPK is essential for DNA repair in response to low-dose of doxorubicin exposure.

Doxorubicin exposure induces DNA double-strand breaks which are repaired by the HR process (Nitiss, 2009). It is known that HR process involves Rad 51 foci where the strand invasion can take place for repair (Holthausen et al., 2010). We tested the effect of TMPK knockdown on formation and resolution of Rad 51 foci in cells after doxorubicin exposure. The results showed that TMPK knockdown did not affect Rad51 foci formation initially. After 24 h, Rad 51 foci number was significantly decreased in control cells, while remained in TMPK knockdown cells (FIG. 2C). This indicates that TMPK knockdown sustains the recombinogenic lesions. We also examined XRCC1 foci which known as a single-strand break repair (SSBR) mark (Caldecott, 2008). As expected, very few XRCC1 foci were detected upon doxorubicin exposure in control and TMPK knockdown cells, demonstrating that TMPK deficiency initially does not induce DNA single-strand breaks (SSBs) upon doxorubicin exposure. At 24-48 h recovery, TMPK knockdown markedly increased the numbers of XRCC1 foci (FIG. 2D), implying that blocking TMPK promotes SSBs during HR process.

It is well established that SSBs are produced by removal of erroneous base via DNA glycosylases and apurinic/apyrimidinic endonuclease (APE)-mediated cleavage at abasic site (Caldecott, 2008; Nazarkina et al., 2007). Uracil DNA glycosylases such as uracil N-glycosylase (UNG) remove uracil from DNA (Krokan et al., 2002; Nilsen et al., 1997). To test whether SSBs revealed by XRCC1 foci result from uracil mis-incorporation, TMPK knockdown cells were infected with lentiviral shRNA of UNG. After recovery from doxorubicin exposure, we observed XRCC1 foci number markedly reduced by UNG knockdown (FIG. 2E). Thus, blocking TMPK promotes the amount of uracil in genome during repairing doxorubicin-induced DSBs.

We, next, tested whether the increase of uracil in genome as a result of dUTP incorporation. Cellular levels of dUTP are controlled primarily by dUTPase, an enzyme responsible for hydrolyzing dUTP to dUMP and pyrophosphate (McIntosh et al., 1992). Wild-type GFP-dUTPase and catalytically dead mutant form of GFP-dUTPase (FIG. 4) were then expressed in MDA-MB231 cells depleted of TMPK. After recovery from doxorubicin exposure, expression of wild-type dUTPase significantly reduced the number of XRCC1 foci in TMPK knockdown cells, while cells expressing catalytically dead dUTPase retained XRCC1 foci (FIG. 2F). Consistently, γH2AX foci were abolished by overexpression of wild-type but not catalytic-dead dUTPase (FIG. 5). In conclusion, TMPK is essential for preventing dUTP incorporation during repairing DSBs.

Example 2

RNR at DNA Damage-Site Requires Functional Coordination of TMPK for Repair

It has been estimated that dUTP/dTTP ratio in cells is in the range 0.3-3% (Traut, 1994). TMPK knockdown cells still retained more than 60% of dTTP pool and these cells proliferate (FIG. 7). Likely, cells contain other functional analogues of TMPK to compensate for this specific depletion. Presumably, the cellular level of dTTP is still much higher than dUTP in these cells. This invoked the question why knockdown of this specific TMPK causes dUTP incorporation in DNA repair.

To assess the functional requirement of TMPK in DNA repair, MDA-MB231 breast cancer cells were transfected with pEGFP-TMPK (D15R), a catalytic-dead mutant (FIG. 8). Of note, overexpression of TMPK (D15R) in HeLa cells with high transfection efficiency did not affect the total dTTP pool (FIG. 9). After doxorubicin exposure and recovery, we found that γH2AX foci diminished in non-transfected cells or cells overexpressing wild-type of GFP-TMPK as a contrast to persistent γH2AX foci in GFP-TMPK (D15R)-positive cells (FIG. 6A). Given that endogenous function of TMPK is not affected by TMPK(D15R) expression, the inhibitory effect of TMPK (D15R) expression on DNA repair is unlikely related to the size of dTTP pool.

RNR-mediated reaction can produce dUDP which is converted to dUTP by NDP kinase (Mathews, 2006). Since TMPK knockdown causes dUTP incorporation in DNA repair, we examined the effect of disrupting RNR recruitment to DNA damage sites on repair in MDA-MB231 cells with TMPK knockdown. To this end, we overexpressed an YFP-fused to 90-amino-acid C-terminal fragment of the R1 subunit (R1C-NLS-YFP) that interferes the interaction between endogenous RNR with Tip60 required for damage-site recruitment (Niida et al., 2010a). Remarkably, overexpression of this R1C-NLS-YFP fusion abolished the effect of TMPK knockdown on increasing the number of γH2AX foci during recovery from doxorubicin exposure (FIG. 6B). The effect of TMPK(D15R) overexpression was also reversed by coexpression of R1C-NLS-YFP (FIG. 6C). Thus, RNR at DNA damage site requires TMPK functional coupling to prevent dUTP-mediated persistent lesion.

To learn whether TMPK and RNR are recruited to DNA-damage site, we transfected cells with expression vector encoding I-Ppol, which introduces a specific DSB on chromosome 1 (Flick et al., 1998). This system allows analysis of the recruitment of repair proteins, such as ATM, to a specific DNA damage site during HR repair to be monitored (Berkovich et al., 2007). Chromatin immunoprecipitation (ChIP) analysis showed TMPK occupancy at the I-Ppol cleavage site on chromosome 1, but not GAPDH gene site, with I-Ppol expression, so as were ATM and R2 subunit of RNR (FIG. 6D). We further analyzed TMPK and R2 on the DNA damage site in cells. Using laser microirradiation to damage DNA, we detected colocalization of TMPK and R2 with γH2AX along with microirradiated line (FIG. 6E). In conclusion, there is functional coupling of TMPK with RNR at DNA damage-site for repair.

Example 3

High Level of R2 Expression as a Determinant in Tumor Cells that Demand TMPK for DNA Repair We further tested the requirement of TMPK for DNA repair in another breast cancer cell line, MCF-7, and non-tumorigenic cycling mammary cell line H184B5F5/M10 and MCF10A. Similar to MDA-MB231 cells, TMPK knockdown caused doxorubicin-induced γH2AX foci persistent in MCF-7 cells. In contrast, DNA repair was unaffected by TMPK knockdown in H184B5F5/M10 and MCF-10A (FIG. 10A). We compared expression levels of R2, p53R2, TMPK and dUTPase during recovery from DNA damage in MDA-MB231, MCF-7, H184B5F5/M10, and MCF10A cells (FIG. 10B). Expression level of R2 subunit of RNR and dUTPase in MDA-MB231 and MCF-7 was much higher than those in H184B5F5/M10 and MCF-10A cells. In MDA-MB231 cells, the R2 and dUTPase level was increased concomitantly between recovery 12 and 48 h post-doxorubicin exposure. Expression level of p53R2 is very low in MDA-MB231 because of functional deficiency of p53. In MCF-7, H184B5F5/M10, and MCF10A cells, the expression of p53R2 was increased between 24-48 h during recovery from doxorubicin exposure. The flow cytometry analysis demonstrated that the population of G0/G1 phase cells in H184B5F5/M10 and MCF-10A cells was 2-3-fold higher than those in MDA-MB231 and MCF-7 cells during recovery from DNA damage. More S and G2/M populations of MDA-MB231 and MCF-7 cells in recovery indicate less stringency in checkpoint control in response to genome insult (FIG. 10C). We also compared cell growth rate of these four cell lines (FIG. 10D). Under our experimental condition, H184B5F5/M10 or MCF-10A cells, indeed, proliferated faster than MDA-MB231 and MCF-7 cells (FIG. 10D). Considering the HR repair takes place in the S and G2 phase, we further treated H184B5F5/M10 cells with nocodazole overnight to block mitotic progression and thereby increasing S/G2 cells as revealed by flow cytometry analysis (FIG. 10E). We exposed these cells to doxorubicin and performed γH2AX staining after recovery. Similar to the asynchronous cultures, H184B5F5/M10 cells with 20% increase in S/G2 population after nocodazole treatment were still insensitive to TMPK knockdown in DNA repair (FIG. 10F). Therefore, it is unlikely that the differential response to TMPK knockdown in DNA repair is determined by the difference in the cell cycle distribution. These data indicated that the sensitivity differences to TMPK knockdown in DNA repair efficiency are not correlated with the proliferation rate of these cell lines. It has been previously reported that enzymatic activity of R2/R1 complex is 5-fold higher than that of p53R2/R1 (Qiu et al., 2006; Shao et al., 2004). DNA repair in H184B5F5/M10 cells with low expression level of R2 was not affected by TMPK knockdown.

Considering that RNR at DNA damage site contributes to dUTP incorporation in MDA-MB231 cells with TMPK knockdown, we then tested whether elevation of R2 in tumor cells is a major factor determining the requirement of TMPK for DNA repair. MCF-7 cells express high level of R2 with p53R2 expression at the level similar to that seen in H184B5F5/M10 cells. We then decreased R2 level in MCF-7 cells by siRNA transfection to test the contribution of R2 (FIG. 11A). The flow cytometric analysis showed that either decreasing R2 by siRNA transfection or in combination with TMPK knockdown did not increase G0/G1 population (FIG. 11B). At 24 h after recovery, γH2AX foci were detected in cells transfected with either R2 siRNA alone or R2/TMPK siRNA. However, at 36 h after recovery, it turned out that decreasing R2 expression rescued DNA repair in MCF-7 cells with TMPK knockdown (FIG. 11C, D). Therefore, it is unlikely that the distribution of cell cycle phase determines the response of DNA repair to TMPK knockdown. Rather, the amount of R2 is a key factor.

We further elevated the level of R2 in MCF-10A cells by lentiviral infection and examined DNA repair response to TMPK knockdown. The results showed that enforced expression of R2 caused persistent γH2AX staining in TMPK knockdown cells with little effect on cell cycle distribution (FIG. 11E). Thus, elevation of R2 expression turns MCF10A sensitive to TMPK knockdown in DNA repair. Altogether, our data demonstrated that an increase in R2 level and the recruitment of RNR to the DNA damage site are two key factors that make TMPK critical for DNA repair in tumor cells. In other words, the elevation of RNR function at DNA damage-sites in tumor cells particularly requires TMPK functional coordination to prevent dUTP incorporation.

Example 4

Screening and Characterization of YMU1 as a Human TMPK Inhibitor

Based on the functional requirement of TMPK in DNA repair specifically in tumor cells with elevated level of R2 expression, we searched for inhibitors of hTMPK that might be useful in selectively sensitizing tumor cells to doxorubicin. By using a luciferase-coupled TMPK assay (Hu and Chang, 2010) in which inhibition of TMPK leaves more ATP available for the generation of luminescence by luciferase (FIG. 12A), we screened a library of 21,120 small molecules and identified one highly potent compound YMU1, of which structure is shown in FIG. 12B. The synthetic procedure and structural elucidation of YMU1 (compound 21) are described in the Methods of the Invention section of the application.

An enzymatic assay confirmed YMU1 to be a hTMPK inhibitor with an $IC_{50}$ of 0.61±0.02 µM (FIG. 12C) and without inhibitory effect on activity of purified thymidine kinase 1 (TK1) (FIG. 12D). To investigate the structure and activity relationship, two fragmented compounds (D3 (compound 4) and D6 (ethyl 4-(2-iodoacetyl)piperazine-1-carboxylate)), one O-alkylation isomer D7 (compound 28) and a benzeneisothiazolone derivative D8 (compound 10) were synthesized (FIG. 12B). Neither D6 (as the piperazine fragment of YMU1) nor D7 (as the O-alkylation isomer of YMU1)

showed any inhibition against hTMPK, whereas D3 (as the pyridinoisothiazolone fragment of YMU1) exhibited a weak inhibitory activity. Interestingly, the benzeneisothiazolone derivative D8 also displayed a considerable inhibitory function.

The inhibitory mode of YMU1 was determined by pre-incubating different concentrations of YMU1 with purified hTMPK protein and measuring initial velocity using the conventional TMPK assay. The values of $K_m$ and $V_{max}$ were determined using a non-linear regression analysis and were summarized in Table 1.

TABLE 1

Effect of YMU1 on kinetic parameters of purified human thymidylate kinase

| YMU1 compound (µM) | $K_m$ for TMP (µM) | $V_{max}$ (nmol/min/mg) | $K_i$ (µM) |
|---|---|---|---|
| 0 | 28.7 ± 2.4 | 376.6 ± 14.5 | 0.22 ± 0.03 |
| 0.125 | 26.5 ± 2.8 | 258.9 ± 12.4 | |
| 0.25 | 27.5 ± 4.0 | 180.6 ± 11.8 | |
| 0.5 | 28.0 ± 4.3 | 91.8 ± 6.4 | |

| YMU1 compound (µM) | $K_m$ for ATP (µM) | $V_{max}$ (nmol/min/mg) | $K_i$ (µM) |
|---|---|---|---|
| 0 | 25.7 ± 2.4 | 367.2 ± 9.4 | 0.18 ± 0.06 |
| 0.25 | 29.5 ± 5.6 | 212.0 ± 10.3 | |
| 0.5 | 41.2 ± 7.4 | 94.8 ± 6.9 | |
| 1 | 43.8 ± 3.3 | 55.7 ± 1.3 | |

For $K_i$ value determination, YMU1 at the indicated concentration was pre-incubated with 0.5 µg of purified hTMPK protein for 10 min, and the initial velocity of the TMPK reaction was measured in the presence of ATP (1 mM) and different concentrations of TMP (2~200 µM) or in the presence of TMP (200 µM) and different concentrations of ATP (5~1000 µM) using NADH-coupled TMPK assay as described in described in the Methods of the Invention section. Data represent mean ± s.d., n = 4. Data obtained from the non-linear regression analysis were calculated for $K_m$ and $V_{max}$ determination. The $K_i$ value of YMU1 compound for hTMPK was calculated from an equation of $K_i = [I]/(V_{max}/V_{max'} - 1)$, where [I] and $V_{max'}$ are YMU1 compound concentration and maximal velocity in the presence of YMU1, respectively. $K_i$ value represents average derived from three different YMU1 concentrations.

Pre-incubation with YMU1 decreased the Vmax of hTMPK in a concentration-dependent manner and increased Km for ATP without significantly affecting $K_m$ for TMP. The inhibition constant ($K_i$) was determined to be 0.22±0.03 µM by kinetic analysis (Table 1).

Molecular docking studies were performed to analyze the mechanism of TMPK inhibition by YMU1. The kinetic studies suggested that YMU1 probably affects the ATP binding pocket of TMPK. Using the cocrystal structure of TMPK with ATP and $Mg^{+2}$, YMU1 was docked into the ATP pocket. In this docking situation, YMU1 prevented one $Mg^{+2}$ ion from interacting with the Asp15 residue in the catalytic domain (FIG. 12E). Since the mutation of Asp15 to Arg caused the loss of TMPK catalytic function, it is possible that preincubation of TMPK with YMU1 hinders $Mg^{+2}$ pointing toward the catalytic function of Asp15 in the ATP pocket, thereby decreasing catalytic efficiency. D3 (compound 4), D6 (ethyl 4-(2-iodoacetyl)piperazine-1-carboxylate) and D7 (compound 28) docking into these sites were unable to block Asp15 interacting with $Mg^{+2}$, therefore, they do not inhibit TMPK.

The investigators performed additional experiments to determine the effect of YMU1 treatment on cellular dTTP levels. YMU1 treatment in cells reduced dTTP pool about 30-40% after treatment with YMU1 for 3 days (FIG. 13). Transfection of these cells with siRNA to knock-down TMPK expression reduced the dTTP pool size in a similar magnitude. YMU1 treatment did not cause a further reduction in these TMPK knockdown cells (FIG. 13), indicating that the ability of YMU1 to reduce dTTP levels was dependent on TMPK present in the cells.

Example 5

YMU1 is not Genome Toxic and Impairs DSBs Repair Like TMPK Silencing

TMPK and TS are key enzymes in dTTP synthesis and TS has been a major chemotherapy target (Garg et al., 2010). Inhibition of TS by FdUrd causes genome toxicity (Longley et al., 2003). Given the shared role of TMPK and TS in dTTP synthesis, we next compared the effects of blocking TMPK and TS by either shRNA interference or inhibitor treatment on the induction of DNA damage. As indicated by the results of γH2AX staining (Mah et al., 2010), silencing of TS or FdUrd treatment induced severe DNA damage, while silencing of TMPK and YMU1 treatment did not (FIG. 14A).

We also compared the effect of YMU1 and FdUrd on cell viability of non-tumorigenic mammary cycling cells, H184B5F5/M10 and MCF-10A and tumor lines, MCF-7 and HCT-116 p53$^{-/-}$ cells. The colony and assay indicated that FdUrd caused death of these cells while YMU1 did not (FIG. 14B). Therefore, unlike blocking TS, targeting TMPK does not, on its own, cause genome toxicity or cytotoxicity to normal cycling cells. We next examined the effect of YMU1 on repairing doxorubicin-induced DNA lesions in MDA-MB231 and H184B5F5/M10 cells after recovery from low-dose doxorubicin treatment.

Of note, YMU1 treatment did not affect numbers of DNA lesions formation, as determined by γH2AX focus staining. Like TMPK knockdown, pretreatment with YMU1 caused over 70% of the MDA-MB231 cells still γH2AX-positive after recovery for 48 h post-doxorubicin exposure (FIG. 14C) and did not affect cell cycle progression during recovery (data not shown).

A comet assay analysis further confirmed that YMU1 treatment resulted in an impairment of DNA repair in cells with doxorubicin exposure (FIG. 15). Overexpression of GFP-TMPK rendered MDA-MB231 cells resistant to YMU1 in sustaining DNA lesions, supporting that the effect of YMU1 is via targeting TMPK (FIG. 14D). Similar to siRNA knockdown, YMU1 also led to persistent Rad51 foci with an increase in XRCC1 foci formation which was abolished by UNG depletion (FIGS. 14E-G). The effect of YMU1 on impairing DNA repair was reversed by overexpression of either dUTPase or C-terminal 90 amino-acid of R1 subunit (FIGS. 14H-I), confirming that YMU1 does not affect the repair process.

Example 6

YMU1 Sensitizes Malignant Tumor Cells to Doxorubicin In Vitro and In Vivo

Next, various human cancer cell lines were treated with YMU1, D6 or D7 for 72 h to test the potential of TMPK inhibitor in doxorubicin sensitization. After exposure to different concentration of doxorubicin for 4 h, cells were refreshed for viability analysis after 2 days and the $IC_{50}$ value for doxorubicin in each of the cell lines was determined (FIG. 16A and Table 2).

TABLE 2

IC$_{50}$ of doxorubicin treatment (μM)

| Cell Line | Treatment | | Enhancement fold |
|---|---|---|---|
| | Vehicle | YMU1 | |
| HCT-116p53+/+ | 2.66 ± 0.49 | 0.42 ± 0.05 | 6.3 |
| HCT-116p53−/− | 4.10 ± 0.01 | 0.60 ± 0.03 | 6.8 |
| HT-29 | 12.09 ± 1.64 | 3.59 ± 0.53 | 3.4 |
| MDA-MB231 | 2.17 ± 0.30 | 0.07 ± 0.03 | 31.0 |
| MDA-MB468 | 0.25 ± 0.08 | 0.009 ± 0.001 | 27.8 |
| H1299 | 7.19 ± 0.77 | 0.59 ± 0.02 | 12.2 |
| CL-1-0 | 4.90 ± 0.20 | 0.82 ± 0.04 | 6.0 |
| SaoS2 | 7.83 ± 0.02 | 0.22 ± 0.01 | 35.1 |
| U2OS | 4.58 ± 0.14 | 1.14 ± 0.05 | 4.0 |
| H184B5F5/M10 | 4.15 ± 0.06 | 2.43 ± 0.01 | 1.7 |
| MCF-10A | 5.22 ± 0.39 | 4.35 ± 0.01 | 1.2 |
| HMEC | 23.56 ± 1.23 | 23.20 ± 1.00 | 1.0 |
| HREC | 22.10 ± 1.18 | 22.00 ± 0.89 | 1.0 |
| Capan1 | 1.13 ± 0.02 | 1.09 ± 0.05 | 1.0 |
| HCC1037 | 5.52 ± 0.39 | 6.9 ± 0.50 | 0.8 |
| IMR-90 | 14.15 ± 3.21 | 13.74 ± 2.94 | 1.0 |

YMU1 treatment increased doxorubicin sensitivity ranging from 3- to 35-fold in HT-29, U2OS, CL-1-0, HCT-116 p53+/+, HCT-116 p53−/−, H1299, MDA-MB468, MDA-MB231, and SaoS2 malignant tumor cells. The ability of YMU1 to sensitize non-tumorigenic mammary cycling H184B5F5/M10, MCF10A, primary human mammary epithelial (HMEC) and primary renal epithelial (HREC) cells and IMR-90 embryonic lung fibroblasts to doxorubicin was much weaker. Two BRCA 1/2 deficient tumor cells that are defective in homologous recombination repair were not responsive to YMU1 in doxorubicin sensitization. Inactive D6 (ethyl 4-(2-chloroacetyl)piperazine-1-carboxylate) and D7 (compound 28) had no doxorubicin sensitization effect in all these cell lines.

The colony assay further showed that YMU1 markedly enhanced the lethal effects of doxorubicin (0.1 μM) in various cancer cell lines (FIG. 16B). TMPK knockdown was unable to further sensitize YMU-treated MDA-MB231 cells to doxorubicin (FIG. 17), suggesting the specificity of YMU1 on doxorubicin sensitization by targeting TMPK. Overexpression of wild-type dUTPase was able to prevent YMU1/doxorubicin-induced apoptosis, as revealed by reducing Annexin V staining (FIG. 18). Moreover, YMU1 was unable to inhibit dUTPase (FIG. 19).

We also used an in vivo xenograft model to examine the effect of YMU1 as an adjuvant on sensitization to low-dose doxorubicin treatment. HCT-116 p53−/− cells were inoculated into nude mice. Four days later, the mice began to receive thrice- and twice weekly i.p. injections of YMU1 and doxorubicin, respectively. Treatment with YMU1 and doxorubicin was continued for 4 weeks. Tumor growth rates in mice treated with either doxorubicin or YMU1 alone were similar to those in control animals. In contrast, the growth of tumors was much slower in YMU1-/doxorubicin-double-treated mice (FIG. 16C). Two weeks after the last injections were administered, mice were sacrificed and tumor weights measured. We observed excellent tumor suppression in YMU1-/doxorubicin-double-treated mice, in which the average tumor size was 25% of that in control mice (FIG. 16D). Under these experimental conditions, tumor sizes were similar in mice treated with doxorubicin or YMU1 alone. In agreement with the data in tumor growth, the tumor proliferation index, indicated by measuring K$_i$ 67 immunostaining, was clearly reduced in nude mice with combinatory treatment of YMU1 and doxorubicin (FIG. 16E).

To assess in vivo toxicity of YMU1, we treated Balb/c mice with YMU1 for 4 weeks, using a 2-fold higher dose regimen in the tumor xenograft study. YMU1 treatment did not alter mouse body weight over the course of 4 weeks. Additionally, weights of the different organs (heart, liver, spleen, lung, and kidney) and results of hematological analyses were similar in control and YMU1-treated mice (Table 3). Taken together, YMU1, on its own, produces no toxic effect in normal mice. In conjunction with low-dose of doxorubicin, YMU1 suppresses tumor growth in mice.

TABLE 3

Effect of YMU1 on animal toxicity

| | | Animal Groups | |
|---|---|---|---|
| | Tests | Control (n = 5) Mean ± SEM | Treatment (n = 4) Mean ± SEM |
| 1 | Clinical observations | Nil | Nil |
| 2 | Body weight (g) | | |
| a) | Pre-treat | 20.96 ± 1.06 | 19.93 ± 1.63 |
| b) | Week-1 | 21.14 ± 0.69 | 20.48 ± 1.43 |
| c) | Week -2 | 21.58 ± 0.48 | 20.88 ± 1.07 |
| d) | Week-3 | 21.52 ± 0.4 | 21.25 ± 1.13 |
| e) | Week-4 | 21.58 ± 0.74 | 21.30 ± 0.96 |
| 3 | Organ weight (g/100 g of body weight) | | |
| a) | Heart | 0.007 ± 0.002 | 0.007 ± 0.000 |
| b) | Liver | 0.054 ± 0.007 | 0.054 ± 0.002 |
| c) | Spleen | 0.008 ± 0.001 | 0.008 ± 0.001 |
| d) | Lung | 0.007 ± 0.001 | 0.006 ± 0.000 |
| e) | Kidney | 0.016 ± 0.001 | 0.016 ± 0.001 |
| 4 | Blood Chemistry | | |
| a) | Aspartate Aminotransferase (U/L) | 68.2 ± 12.76 | 62.50 ± 5.26 |
| b) | Alanine Aminotransferase (U/L) | 32.80 ± 3.83 | 32.00 ± 2.45 |
| c) | Alkaline Phosphatase (U/L) | 353.00 ± 58.51 | 389.25 ± 20.79 |
| d) | Glucose (mg/dl) | 157.6 ± 9.74 | 136.25 ± 14.31* |
| e) | Blood Urea Nitrogen (mg/dl) | 22.42 ± 2.394 | 19.08 ± 3.25 |
| f) | Creatinine (mg/dl) | 0.16 ± 0.09 | 0.10 ± 0.00 |
| g) | Total protein (g/dl) | 5.44 ± 0.35 | 5.48 ± 0.25 |
| 5 | Hematology | | |
| a) | Hb (g/dl) | 16.56 ± 0.63 | 16.25 ± 0.41 |
| b) | PCV (%) | 55.50 ± 2.74 | 53.48 ± 2.50 |
| c) | Total RBC Counts (per cmm) | 10.80 ± 0.63 | 10.39 ± 0.48 |
| d) | Total WBC Counts (per cmm) | 8.41 ± 1.79 | 8.54 ± 2.95 |

*P < 0.05

Example 7

In Vitro and In Vivo Activity of TMPK Inhibitor Derivatives

Chemical structures of the different TMPK inhibitor derivatives tested for in vitro TMPK inhibitory activity and in vivo doxorubicin sensitization activity (in MDA-MB231 cells) are depicted below.

1

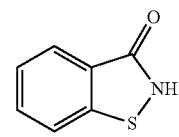

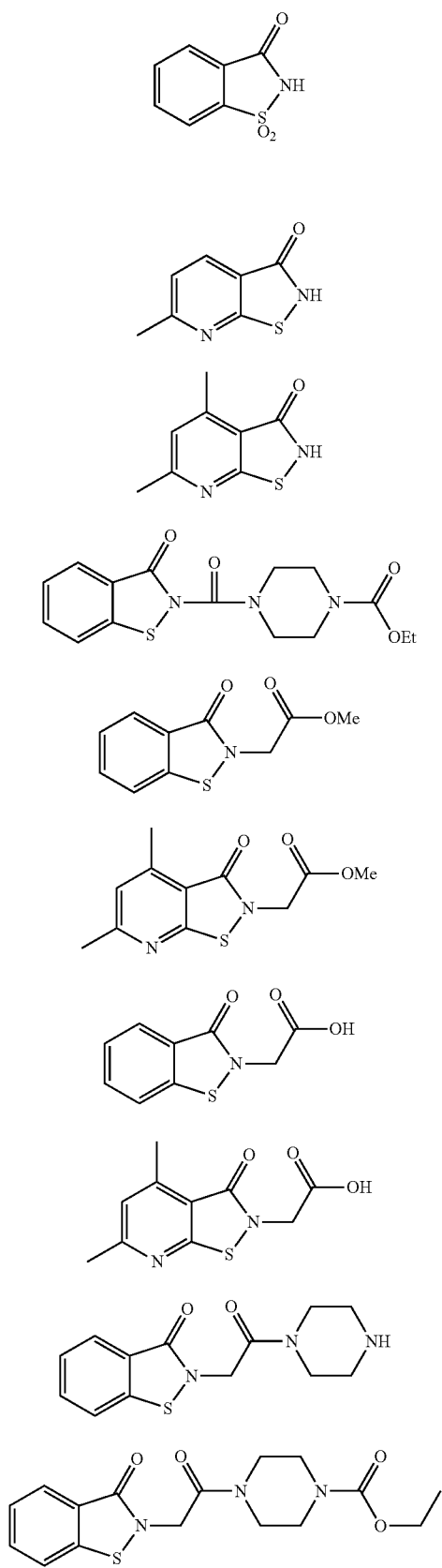
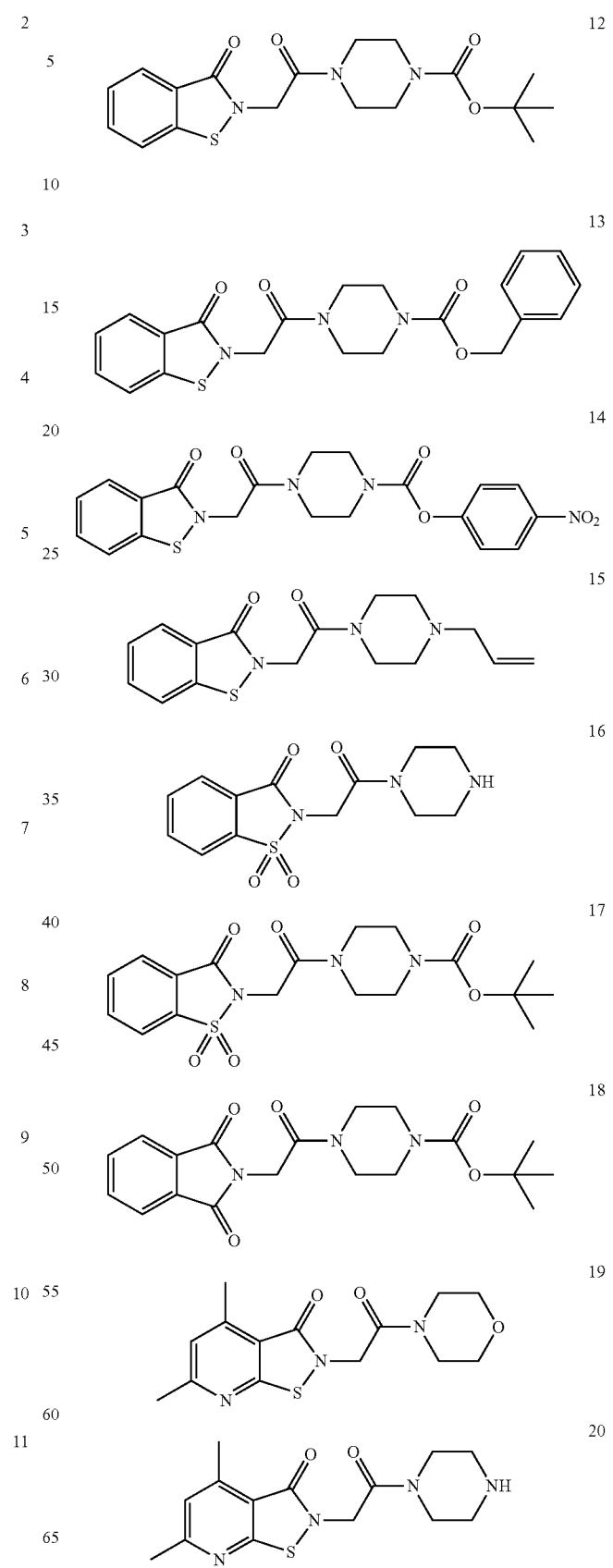

21

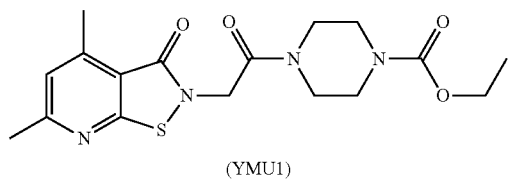

(YMU1)

22

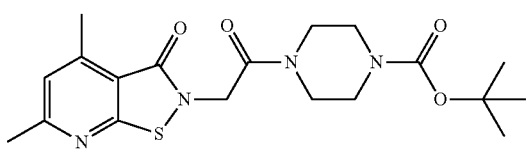

23

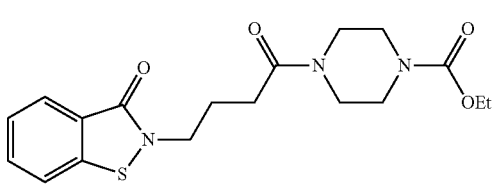

24

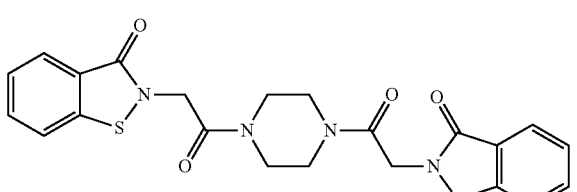

25

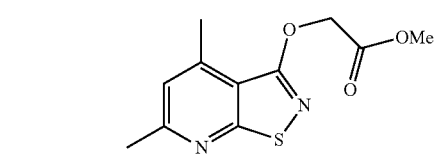

26

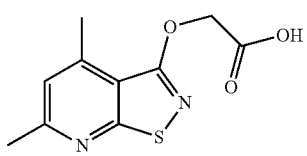

27

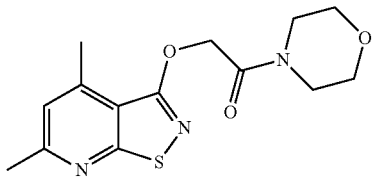

28

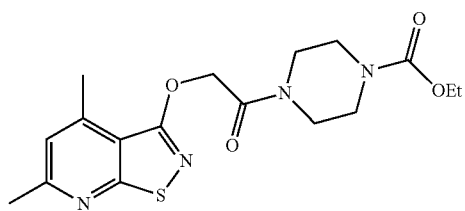

In one embodiment, compound 21 (YMU1) is designated as the standard to have 100% inhibition yield at a concentration of 2 µM. The inhibition yields of other TMPK inhibitor derivative compounds are normalized (n=3 or 6) accordingly: Compound 1 (74.0%), compound 2 (7.0%), compound 3 (76.5%), compound 4 (28.0%), compound 5 (92.9%), compound 6 (96.0%), compound 7 (98.3%), compound 8 (29.1%), compound 9 (47.0%), compound 10 (96.8%), compound 11 (100.4%), compound 12 (124.5%), compound 13 (127.2%), compound 14 (129.4%), compound 15 (102.3%), compound 16 (11.8%), compound 17 (10.1%), compound 18 (51.4%), compound 19 (100.5%), compound 20 (99.5%), compound 21 (YMU1, 100%), compound 22 (111.6%), compound 23 (0%), compound 24 (117.7%), compound 25 (7.8%), compound 26 (16.4%), compound 27 (16.0%), and compound 28 (14.7%). In MDA-MB231 cell treatment, compound 10 and 19 at 2 µM had no effect on doxorubicin sensitization, while compound 12 and 21 at 2 µM had 30-fold enhancement on doxorubicin sensitization.

Based on these results, it appears that the bicyclic core structure is important for the activity of TMPK inhibitors. As illustrated for the YMU1 (compound 21) and the related TMPK inhibitors, the N-alkylated structure at the thiazolone ring appears to be required for the observed activity while the C-terminal moiety at the piperazine ring is required for in vivo doxorubicin sensitization.

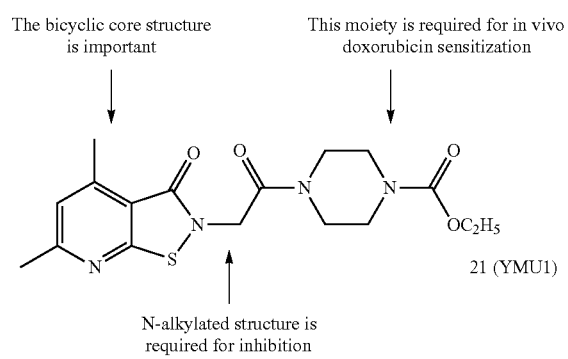 [SMILES: CCOC(=O)N1CCN(C(=O)Cn2sc3nc(C)cc(C)c3c2=O)CC1]

Methods of the Invention

Antibodies

Anti-hTMPK and anti-hTK1 polyclonal antibodies were prepared as described previously (Chang et al., 1994; Ke et al., 2005). Anti-R2 (sc-10844), anti-p53 R2 and anti-ATM (sc-23921) antibodies were from Santa Cruz. Antiserum against hdUTPase was produced by immunizing rabbits with purified GST-hdUTPase (nuclear form) protein and collected, after which polyclonal antibody was affinity-purified. Specificity of hTMPK, R2 and hdUTPase antibodies were verified by RNAi experiments (FIG. 20). Anti-GFP antibody (632375) was from BD Biosciences. Anti-hTS antibody (clone 4H$_4$B1) was purchased from Zymed Laboratories inc., Anti-Rad-51 antibody (PC130) was from Calbiochem. Anti-H2AX (Ser139) and anti-XRCC1 (clone 33-2-5) antibodies were purchased from Upstate and Thermo Fisher Scientific Inc., respectively. Anti-β-tubulin, anti-β-actin, anti-rabbit IgG-FITC, anti-mouse IgG-FITC and anti-mouse IgG-TRITC antibodies were from Sigma.

Reagents

G418 and nanofectin were obtained from Invitrogen and PAA laboratories Inc., respectively. ATP, TMP, NADH, phosphoenol pyruvate, 5,5'-dithio-bis(2-nitrobezoic acid) (DTNB), D-Luciferin, Photinus pyralis (firefly) Luciferase, human thrombin, bovine serum albumin (BSA), doxorubicin and H33342 were purchased from Sigma. Lactate dehydrogenase and pyruvate kinase were obtained from Roche. Glutathione 4B beads were from Amersham Pharmacia, and Annexin V-IDE apoptosis kit (CBA-060) and MTS reagent were purchased from Calbiochem and Promega, respectively. hTMPK siRNA was obtained from Dharmacon siGenome SMART pools (MQ-006720), synthesis of R2 siRNA and Lipofectamin 2000 from Invitrogen. Dialyzed serum was purchased from GIBCO™. pLKO-UNG shRNA and pLKO-dUTPase shRNA were purchased from national RNAi core facility in Taiwan.

Cell Culture and Establishment of Stable Cell Lines

HCT-116 p53+/+ and p53-/- cells were kindly provided by Bert Vogelstein at the Johns Hopkins University Medical Institution (Bunz et al., 1998). U205-DR-GFP cells were provided by Sheau-Yen Shieh, Academia Sinica. The growth medium supplemented with 10% FBS were: McCoy's 5A for HCT-116 and U205, RPMI for HT-29, DMEM for MDA-MB231, MDA-MB468, HeLa and HEK-293T, MEM-α for H184B5F5/M10 cells from Bioresource Collection and Research Center (Hsinchu, Taiwan) (Yang et al., 1996). For establishment of MDA-MB231 cells stably expressing TMPK shRNA and HCT-116 p53-/- cells stably expressing TMPK shRNA, cells were infected with lentiviral TMPK shRNA, after which cells were selected with 2 µg/ml blasticidine.

General Material for Chemical Synthesis of Compounds.

All reagents and solvents were reagent grade and used without further purification unless otherwise specified. All solvents were anhydrous grade unless indicated otherwise. Dichloromethane ($CH_2Cl_2$) was distilled from $CaH_2$. All air or moisture sensitive experiments were performed under nitrogen. Reactions were monitored by thin-layer chromatography (TLC) on 0.25 mm E. Merck silica gel 60 $F_{254}$ glass plates. Compounds were visualized by UV, or using p-anisaldehyde, ninhydrine and phosphomolybdic acid (PMA) as visualizing agent. E. Merck silica gel 60 (0.040-0.063 mm particle sizes) were used for flash chromatography.

Instrumentation.

Melting points were recorded on a Yanaco micro apparatus. Absorbance spectra were measured on PerkinElmer Lamda 35 UV-Vis spectrometer. Nuclear magnetic resonance (NMR) spectra were obtained on Varian Unity Plus-400 (400 MHz) and chemical shifts (δ) were recorded in parts per million (ppm) relative to $δ_H$ 7.24/$δ_C$ 77.0 (central line of t) for $CHCl_3/CDCl_3$, $δ_H$ 3.31/$δ_C$ 49.0 for $CH_3OH/CD_3OD$, and $δ_H$ 2.50 (m)/$δ_C$ 39.5 (m) for $(CH_3)_2SO/(CD_3)_2SO$. The splitting patterns are reported as s (singlet), d (doublet), t (triplet), q (quartet), m (multiplet) and br (broad). Coupling constants (J) are given in Hz. The ESI-MS experiments were conducted on a Bruker Daltonics BioTOF III high-resolution mass spectrometer. High-performance liquid chromatography (HPLC) was performed on Agilent 1100 Series instrument equipped with a degasser, Quat pump, and UV detector.

Determination of the Purity of Compounds.

The purity of compounds were determined by HPLC on a HC-C18 column (Agilent, 4.6×250 mm, 5 µM) at a flow rate of 1 mL/min with gradient elution of 20-90%, 30-90% or 40-90% aqueous $CH_3CN$ for 15 min or 20 min.

6-Methylisothiazolo[5,4-b]pyridin-3(2H)-one (compound 3)

A mixture of 2-chloro-6-methylnicotinonitrile (220 mg, 1.45 mmol) and thiourea (348 mg, 4.57 mmol) was heated at reflux (118° C.) in n-butanol for 4 h. After cooling to room temperature, the yellow solution turned to a suspension containing light yellow solids. The solids were collected by filtration, rinsed with n-butanol, and dried in vacuo to give 2-mercapto-6-methylnicotinonitrile (218 mg, 100% yield). $C_7H_6N_2S$; yellow powder; $^1H$ NMR (400 MHz, $CDCl_3$) δ 7.97 (1H, dt, J=8, 0.8 Hz), 7.79 (1H, dt, J=8, 0.8 Hz), 7.70 (1H, td, J=8, 1.2 Hz), 7.46 (1H, td, J=8, 1.2 Hz), 4.64 (2H, s); $^{13}C$ NMR (100 MHz, $CDCl_3$) δ 177.39, 154.77, 144.83, 117.1, 113.3, 112.7, 19.2; ESI-HRMS (negative mode) calcd for $C_7H_5N_2S$: 149.0173. found: m/z 149.0172 [M–H]$^-$.

The above-prepared compound (120 mg, 0.80 mmol) was added to conc. $H_2SO_4$ (1 mL). The mixture was immersed in a preheated oil bath at 100° C. for 4 h. The mixture was then cooled and modulated to pH 5-6 by addition of saturated $NaHCO_3$, producing insoluble substance in suspension. The solids were collected by filtration, and dried in vacuo to give the title compound (86 mg, 65% yield). $C_7H_6N_2OS$; yellow powder; mp 187-190° C.; $^1H$ NMR (400 MHz, $CDCl_3$) δ 8.16 (1H, d, J=7.8 Hz), 7.21 (1H, d, J=7.8 Hz), 2.70 (3H, s); $^{13}C$ NMR (100 MHz, $CDCl_3$) δ 167.0, 165.5, 164.1, 134.1, 120.2, 116.1, 24.1; ESI-HRMS (negative mode) calcd for $C_7H_5N_2OS$: 150.9966. found: m/z 150.9965 [M–]$^-$.

4,6-Dimethylisothiazolo[5,4-b]pyridin-3(2H)-one (4)

A mixture of 2-chloro-4,6-dimethylnicotinonitrile (800 mg, 4.83 mmol) and thiourea (1.2 kg, 15.76 mmol) was heated at reflux (118° C.) in n-butanol for 4 h. After cooling to room temperature, the yellow solution turned to a suspension containing light yellow solids. The solids were collected by filtration, rinsed with n-butanol, and dried in vacuo to give 2-mercapto-4,6-dimethylnicotinonitrile (778 mg, 98% yield). $C_8H_8N_2S$; light yellow powder; mp 219-221° C.; $^1H$ NMR (400 MHz, $CDCl_3$) δ 6.40 (1H, s), 2.45 (3H, s), 2.43 (3H, s); ESI-HRMS (negative mode) calcd for $C_8H_7N_2S$: 163.0330. found: m/z 163.0332 [M–H]$^-$.

The above-prepared compound (750 mg, 4.57 mmol) was added to conc. $H_2SO_4$ (5 mL). The mixture was immersed in a preheated oil bath at 100° C. for 4 h. The mixture was then cooled and adjusted to pH 5-6 by addition of saturated $NaHCO_3$, producing insoluble substance in suspension. The solids were collected by filtration, and dried in vacuo to give the title compound (743 mg, 84% yield). $C_8H_8N_2OS$; light pink powder; mp 190-193° C.; $^1H$ NMR (400 MHz, $CDCl_3$) δ 6.93 (1H, s), 2.74 (3H, s), 2.60 (3H, s); $^{13}C$ NMR (100 MHz, $CDCl_3$) δ 167.5, 165.8, 162.6, 149.2, 122.0, 114.5, 25.0, 18.2; ESI-HRMS (negative mode) calcd for $C_8H_7N_2OS$: 179.0279. found: m/z 179.0281 [M–H]$^-$.

Ethyl 4-(1-oxoisoindoline-2-carbonyl)piperazine-1-carboxylate (5)

A mixture of ethyl piperazine-1-carboxylate (300 mg, 1.90 mmol), 4-nitrophenyl carbonochloridate (460 mg, 2.28 mmol) and $Et_3N$ (576 mg, 5.69 mmol) in anhydrous $CH_2Cl_2$ (7 mL) was stirred at room temperature for 24 h, and then the reaction mixture turned to a yellow solution. Extraction with $NaHCO_{3(aq.)}$ until the organic layer turns to transparent solution. And then the organic layer was dried over $MgSO_4$, filtered, concentrated, and purified by flash chromatography on a silica gel column with elution of EtOAc/hexane (1:1.5) to give 1-ethyl 4-(4-nitrophenyl) piperazine-1,4-dicarboxylate (172 mg, 45% yield). $C_{14}H_{17}N_3O_6$; pale yellow solid; mp 125-128° C.; IR $v_{max}$ (neat) 3512, 3082, 2983, 2930, 2867, 1730, 1701, 1594, 1523, 1459, 1425, 1348, 1288, 1209, 1163, 1085, 1055, 996, 957 cm$^{-1}$; $^1H$ NMR (400 MHz, $CDCl_3$) δ 8.23 (1H, d, J=8.8 Hz), 7.28 (1H, t, J=8.8 Hz), 4.17 (2H, q, J=6.8 Hz), 3.66 (2H, br s), 3.56 (6H, br s), 1.28 (3H, t, J=7.2 Hz); $^{13}C$ NMR (100 MHz, $CDCl_3$) δ 155.7, 155.1, 151.9, 144.7, 124.9 (2×), 122.1 (2×), 61.8, 44.5, 43.8, 43.4 (2×), 14.8.

A mixture of the above-prepared p-nitrophenyl carbamate (100 mg, 0.31 mmol), benzothiazolone (compound 1, 56 mg, 0.37 mmol), 4-dimethylaminopyridine (DMAP, 113 mg, 0.92 mmol) and diisopropylethylamine (DIEA, 120 mg, 0.93 mmol) in $CH_2Cl_2$ (3 mL) was stirred at room temperature. The mixture was stirred for 48 h, and washed successively with 1 M $HCl_{(aq)}$ and saturated $NaHCO_{3(aq.)}$. The organic phase was dried over $MgSO_4$, filtered, concentrated, and purified on a thin-layer silica-gel plate (20 cm×20 cm×2 mm) using $CH_2Cl_2$/MeOH (9:1) as the developing solution to give the title compound. $C_{15}H_{17}N_3O_4S$; white oil; IR $v_{max}$ (neat) 2923, 2853, 1689, 1423, 1259, 1229, 995, 749 $cm^{-1}$; $^1H$ NMR (400 MHz, $CDCl_3$) δ 7.96 (1H, d, J=8.0 Hz), 7.66 (1H, d, J=8.0 Hz), 7.52 (1H, d, J=8.0 Hz), 7.40 (1H, d, J=8.0 Hz), 4.16 (2H, q, J=8.0 Hz), 3.63 (8H, m), 1.28 (3H, t, J=6.8 Hz); ESI-HRMS calcd for $C_{15}H_{17}N_3O_4NaS$: 358.0837. found: m/z 358.0827 [M+Na]+.

Methyl 2-(3-oxobenzo[d]isothiazol-2(3H)-yl)acetate (6)

Benzothiazolone 1 (500 mg, 3.31 mmol) was suspended in $CH_2Cl_2$ (25 mL) containing DIEA (1.28 kg, 9.93 mmol) and $Cs_2CO_3$ (1.75 kg, 3.30 mmol). Methyl 2-bromoacetate (800 mg, 5.26 mmol) was then added at room temperature. The mixture was stirred for 5 h, concentrated under reduced pressure, and purified by chromatography on a silica gel column with elution of EtOAc/hexane (1:2) to give the title compound (495 mg, 67% yield). $C_{10}H_9NO_3S$; white solid; mp 89-91° C.; $^1H$ NMR (400 MHz, $CDCl_3$) δ 8.15 (1H, dt, J=8, 0.8 Hz), 7.59 (1H, td, J=7.2, 1.2 Hz) 7.52 (1H, dt, J=8, 0.8 Hz) 7.37 (1H, td, J=7.2, 1.2 Hz), 4.59 (2H, s), 3.76 (3H, s); $^{13}C$ NMR (100 MHz, $CDCl_3$) δ 167.8, 165.4, 140.6, 132.0, 126.7, 125.4, 123.2, 120.2, 52.6, 44.5; ESI-HRMS calcd for $C_{10}H_9NO_3S$: 224.0381. found: m/z 224.0390 [M+H]+.

Methyl 2-(4,6-dimethyl-3-oxoisothiazolo[5,4-b]pyridin-2(3H)-yl)acetate (7)

To enhance the selectivity of N-alkylation over O-alkylation, pyridinothiazolone 4 (500 mg, 2.77 mmol) was suspended in $CH_2Cl_2$ (20 mL) containing of diisopropylethylamine (DIEA, 1.5 mL, 8.61 mmol) and $Cs_2CO_3$ (700 mg, 3.07 mmol). Methyl 2-bromoacetate (900 mg, 5.88 mmol) was then added at room temperature. The mixture was stirred for 5 h, concentrated under reduced pressure, and purified by chromatography on a silica gel column with elution of EtOAc/hexane (1:4) to give the title compound 7 (360 mg, 55% yield) accompanied by an O-alkylation side product (7%). Compound 7: $C_{11}H_{12}N_2O_3S$; white solid; mp 89-91° C.; IR $v_{max}$ (neat) 2928, 1766, 1728, 1664, 1561, 1523, 1435, 1375, 1324, 1210 $cm^{-1}$; $^1H$ NMR (400 MHz, $CDCl_3$) δ 6.92 (1H, s), 4.54 (2H, s), 3.76 (3H, s), 2.70 (3H, s), 2.57 (3H, s); $^{13}C$ NMR (100 MHz, $CDCl_3$) δ 167.4, 164.3, 162.6, 162.3, 149.6, 122.4, 113.8, 52.8, 44.2, 24.9, 17.8; ESI-HRMS calcd for $C_{11}H_{13}N_2O_3S$: 253.0647. found: m/z 253.0657 [M+H]+.

2-(3-oxobenzo[d]isothiazol-2(3H)-yl)acetic acid (8)

Ester 6 (500 mg, 2.24 mmol) was suspended in conc. HCl (8 mL) and heated with stirring at 100° C. for 6 h until hydrolysis completed.[4] The mixture was cooled to room temperature, diluted with water (500 mL), and the precipitate was collected to give the title compound (460 mg, 98% yield). $C_9H_7NO_3S$; white solid; mp 241-243° C.; $^1H$ NMR (400 MHz, $CDCl_3$) δ 7.97 (1H, dt, J=8, 0.8 Hz), 7.79 (1H, dt, J=8, 0.8 Hz), 7.70 (1H, td, J=8, 1.2 Hz), 7.46 (1H, td, J=8, 1.2 Hz), 4.64 (2H, s); $^{13}C$ NMR (100 MHz, $CDCl_3$) δ 169.4, 166.4, 141.8, 132.3, 125.8, 125.5, 123.4, 121.0, 44.4; ESI-HRMS (negative mode) calcd for $C_9H_7NO_3S$: 208.0068. found: m/z 208.0064 [M−H]−.

2-(4,6-Dimethyl-3-oxoisothiazolo[5,4-b]pyridin-2(3H)-yl)acetic acid (9)

Ester 7 (160 mg, 0.63 mmol) was suspended in conc. HCl (4 mL) and heated with stirring at 100° C. for 5 h until hydrolysis completed. The mixture was cooled to room temperature, diluted with water (500 mL), and the precipitate was collected to give the title compound (151 mg, 100% yield). $C_{10}H_{10}N_2O_3S$; white solid; mp 355° C. (decomposed); $^1H$ NMR (400 MHz, $CD_3OD$) δ 7.13 (1H, s), 4.60 (2H, s), 2.71 (3H, s), 2.59 (3H, s); $^{13}C$ NMR (100 MHz, $CD_3OD$) δ 170.2, 165.7, 164.2, 163.3, 151.3, 123.3, 115.1, 45.2, 24.7, 17.9; ESI-HRMS (negative mode) calcd for $C_{10}H_9N_2O_3S$: 237.0334. found: m/z 237.0329 [M−H]−.

2-(2-Oxo-2-(piperazin-1-yl)ethyl)benzo[d]isothiazol-3(2H)-one (10)

Tert-butyl carbamate 12 (50 mg, 0.13 mmol) and trifluoroacetic acid (TFA, 2 mL, 26.1 mmol) was dissolved in anhydrous $CH_2Cl_2$ (15 mL), and then stirred for 2 h at 27° C. TFA was removed under reduced pressure; the residue was extracted with ammonia solution (35%) and $CH_2Cl_2$. The organic layer was dried over $MgSO_4$, filtered, and concentrated to give the title compound (32 mg, 87% yield). The purity of product was 98.4% as shown by HPLC on an HC-C18 column (Agilent, 4.6×250 mm, 5 μM), $t_R$=7.52 min (gradients of 20-90% aqueous $CH_3CN$ in 15 min). $C_{13}H_{15}N_3O_2S$; foam; IR $v_{max}$ (neat) 3449, 2924, 2852, 1639, 1448, 1356, 1243, 1202, 1134, 1031, 929, 744 $cm^{-1}$; $^1H$ NMR (400 MHz, $CD_3OD$) δ 7.97 (1H, dt, J=8.0, 0.8 Hz), 7.79 (1H, dt, J=8.0, 0.8 Hz), 7.70 (1H, m), 7.38 (1H, m), 4.82 (2H, s), 3.58 (4H, m), 2.90 (2H, t, J=5.2 Hz), 2.84 (2H, t, J=5.2 Hz); $^{13}C$ NMR (100 MHz, $CDCl_3$) δ 165.5, 164.7, 141.3, 131.9, 126.6, 125.3, 123.3, 120.2, 46.5, 46.2, 45.7, 44.8, 43.3; ESI-HRMS calcd for $C_{13}H_{16}N_3O_2S$: 278.0963. found: m/z 278.0962 [M+H]+.

Ethyl 4-(2-(3-oxobenzo[d]isothiazol-2(3H)-yl)acetyl)piperazine-1-carboxylate (11)

Ethyl 4-(2-iodoacetyl)piperazine-1-carboxylate (200 mg, 0.61 mmol) was added to a suspension of benzothiazolone 1 (102 mg, 0.67 mmol), $Et_3N$ (233 mg, 1.83 mmol) and $Cs_2CO_3$ (198 mg, 0.61 mmol) in anhydrous $CH_2Cl_2$ (8 mL) at room temperature. The mixture was stirred for 26 h, and washed with 1 M $HCl_{(aq)}$. The organic phase was dried over $MgSO_4$, filtered, concentrated, and purified by flash chromatography on a silica gel column with elution of EtOAc/hexane (1:2) to give the title compound (134 mg, 63% yield). The purity of product was 99.3% as shown by HPLC on an HC-C18 column (Agilent, 4.6×250 mm, 5 μM), $t_R$=11.87 min (gradients of 20-90% aqueous $CH_3CN$ in 20 min). $C_{16}H_{19}N_3O_4S$; white solid; mp 158-160° C.; $^1H$ NMR (400 MHz, $CDCl_3$) δ 8.09 (1H, dd, J=7.2 Hz, 0.8 Hz), 7.59 (1H, m), 7.53 (1H, dd, J=7.2, 0.8 Hz), 7.38 (1H, m), 4.69 (2H, s), 4.13 (2H, q, J=7.2 Hz), 3.60 (2H, m), 3.55 (2H, m), 3.48 (4H, m), 1.25 (3H, t, J=7.2 Hz); $^{13}C$ NMR (100 MHz, $CDCl_3$) δ 164.6, 154.6, 140.8, 131.8, 130.0, 126.4, 125.1, 122.9, 120.0, 61.9, 45.3, 45.0, 43.5 (2×), 42.2, 15.0; ESI-HRMS calcd for $C_{16}H_{19}N_3O_4S$: 372.0994. found: m/z 372.0992 [M+H]+.

Tert-butyl 4-(2-(3-oxobenzo[d]isothiazol-2(3H)-yl)acetyl)piperazine-1-carboxylate (12)

A mixture of piperazine (1.10 g, 12.8 mmol) and DIEA (1.65 g, 12.8 mmol) in anhydrous $CH_2Cl_2$ (60 mL) was stirred at 27° C., and a solution of di-tert-butyl dicarbonate (1.39 g, 6.39 mmol) in anhydrous $CH_2Cl_2$ (80 mL) was added slowly via a separatory funnel over a period of 20 h. The mixture was partitioned with $H_2O$; the organic phase was separated, dried over $MgSO_4$, filtered and concentrated to give tert-butyl piperazine-1-carboxylate (2.01 g, 85% yield). $C_9H_{18}N_2O_2$; white solid; mp 45-46° C.; $^1H$ NMR (400 MHz, $CDCl_3$) δ 3.38 (4H, t, J=4.8 Hz), 2.80 (4H, t, J=4.8 Hz), 1.73 (1H, s), 1.45 (9H, s); $^{13}C$ NMR (100 MHz, $CDCl_3$) δ 154.1, 79.5, 45.9 (2×), 44.8 (2×), 28.7 (3×); ESI-HRMS calcd for $C_9H_{19}N_2O_2$: 187.1447. found: m/z 187.1451 [M+H]$^+$.

The above-prepared tert-butyl piperazine-1-carboxylate (500 mg, 2.68 mmol) was treated with chloroacetyl chloride (360 mg, 2.95 mmol) in the presence of DIEA (1.04 g, 8.05 mmol) to give tert-butyl 4-(2-chloroacetyl)piperazine-1-carboxylate (571 mg, 81% yield) after purification by flash chromatography on a silica gel column (hexane/EtOAc=1:2). $C_{11}H_{19}ClN_2O_3$; white solid; mp 68-70° C.; $^1H$ NMR (400 MHz, $CDCl_3$) δ 4.06 (2H, s), 3.58 (2H, m), 3.49 (4H, s), 3.44 (2H, m) 1.47 (9H, s); $^{13}C$ NMR (100 MHz, $CDCl_3$) δ 164.5, 153.7, 80.2, 46.2, 43.3 (2×), 42.1, 40.9, 28.5; ESI-HRMS calcd for $C_{11}H_{20}ClN_2O_3$: 285.0982. found: m/z 285.0985 [M+H]$^+$.

The above-prepared chloro compound (52 mg, 0.34 mmol) was added to a suspension of benzothiazolone 1 (90 mg, 0.34 mmol), $Et_3N$ (175 mg, 1.73 mmol) and $Cs_2CO_3$ (167 mg, 0.51 mmol) in anhydrous $CH_2Cl_2$ (20 mL) at room temperature. The mixture was stirred for 22 h, and concentrated under reduced pressure. The residue was extracted with $CH_2Cl_2$ and $H_2O$. The organic phase was dried over $MgSO_4$, filtered, concentrated, and purified by flash chromatography on a silica gel column with elution of EtOAc/hexane (3:1) to give the title compound (87 mg, 67% yield). The purity of product was 96.9% as shown by HPLC on an HC-C18 column (Agilent, 4.6×250 mm, 5 μM), $t_R$=16.6 min (gradients of 20-90% aqueous $CH_3CN$ in 20 min). $C_{18}H_{23}N_3O_4S$; white solid; mp 120-122° C.; IR $v_{max}$ (neat) 2974, 2925, 1655, 1460, 1418, 1364, 1339, 1285, 1171, 1128, 1068, 1028 740 cm$^{-1}$; $^1H$ NMR (400 MHz, $CDCl_3$) δ 8.00 (1H, d, J=8.0 Hz), 7.58 (1H, td, J=8.0, 0.8 Hz), 7.52 (1H, d, J=8.0 Hz), 7.38 (1H, td, J=8.0, 0.8 Hz), 4.68 (2H, s), 3.59 (2H, m), 3.53 (2H, m), 3.41 (4H, m), 1.44 (9H, s); $^{13}C$ NMR (100 MHz, $CDCl_3$) δ 165.0, 164.6, 153.8, 140.8, 131.8, 126.4, 125.1, 122.9, 120.0, 80.4, 45.3, 45.0, 43.4 (2×), 42.2, 28.7 (3×); ESI-HRMS calcd for $C_{18}H_{24}N_3O_4S$: 400.1307. found: m/z 400.1301 [M+H]$^+$.

Benzyl 4-(2-(3-oxobenzo[d]isothiazol-2(3H)-yl)acetyl)piperazine-1-carboxylate (13)

Compound 10 (100 mg, 0.36 mmol) was treated with benzyl chloroformate (75 mg, 0.44 mmol) and DIEA (140 mg, 1.10 mmol) in anhydrous $CH_2Cl_2$ (5 mL) and DMF (1 mL) at room temperature for 4 h. $CH_2Cl_2$ and DMF were removed in reduced pressure. The mixture was washed successively with 1 M $HCl_{(aq)}$ and saturated $NaHCO_{3(aq.)}$. The organic phase was dried over $MgSO_4$, filtered, concentrated, and the title compound was obtained after purification on a thin-layer silica-gel plate (20 cm×20 cm×2 mm) using $CH_2Cl_2$/MeOH (9:1) as the developing solution. $C_{21}H_{21}N_3O_4S$; white solid; mp 138-142° C.; IR $v_{max}$ (neat) 2923, 2854, 1700, 1655, 1428, 1354, 1286, 1227, 1125, 1075, 1027, 984, 861, 741 cm$^{-1}$; $^1H$ NMR (400 MHz, $CDCl_3$) δ 8.01 (1H, d, J=8.0 Hz), 7.60 (1H, t, J=7.2 Hz), 7.53 (1H, d, J=8.0 Hz), 7.36 (6H, m), 5.12 (2H, s), 4.69 (2H, s), 3.62 (8H, m); $^{13}C$ NMR (100 MHz, $CDCl_3$) δ 165.1, 154.8, 141.1, 136.1, 132.1, 128.5, 128.1, 127.9, 126.7 (2×), 126.3 (2×), 125.4, 123.2, 120.2, 67.6, 45.2, 44.9, 43.6 (2×), 42.0; ESI-HRMS calcd for $C_{21}H_{21}N_3O_4NaS$: 434.1150. found: m/z 434.1149 [M+H]$^+$.

4-Nitrophenyl 4-(2-(3-oxobenzo[d]isothiazol-2(3H)-yl)acetyl)piperazine-1-carboxylate (14)

Compound 10 (81.5 mg, 0.29 mmol) was treated with 4-nitrophenyl chloroformate carbonochloridate (213 mg, 1.06 mmol) and DMAP (108 mg, 0.88 mmol) in anhydrous $CH_2Cl_2$ (4 mL) at room temperature for 16 h. The mixture was washed successively with saturated $NaHCO_{3(aq.)}$ and 1 M $HCl_{(aq)}$ until the solution became transparent. The organic phase was dried over $MgSO_4$, filtered, concentrated, and purified by flash chromatography on a silica gel column with elution of $CH_2Cl_2$/MeOH (100:0.5 to 9:1) to give the title compound (70 mg, 56% yield). $C_{20}H_{18}N_4O_6S$; pale yellow solid; mp 114-118° C.; IR $v_{max}$ (neat) 2923, 2854, 1725, 1655, 1520, 1346, 1259, 1163, 1111, 1056, 1024, 862, 748 cm$^{-1}$; $^1H$ NMR (400 MHz, $CDCl_3$) δ 8.22 (2H, d, J=10.2 Hz), 8.02 (1H, d, J=8.0 Hz), 7.62 (2H, t, J=8.0 Hz), 7.55 (1H, d, J=8.0 Hz), 7.40 (1H, t, J=8.0 Hz), 7.27 (1H, d, J=10.2 Hz), 4.73 (2H, s), 3.70 (6H, br s), 3.62 (2H, br s); $^{13}C$ NMR (100 MHz, $CDCl_3$) δ 165.4, 165.1, 155.5, 151.7, 144.7, 141.0, 132.1, 126.5, 125.4, 124.9 (2×), 123.0, 122.0 (2×), 120.2, 44.7, 44.5, 44.2, 43.8, 43.6; ESI-HRMS calcd for $C_{20}H_{19}N_4O_6S$: 443.1025. found: m/z 443.1042 [M+H]$^+$.

2-(2-(4-Allylpiperazin-1-yl)-2-oxoethyl)benzo[d]isothiazol-3(2H)-one (15)

Compound 10 (30 mg, 0.11 mmol) was treated with allyl bromide (16 mg, 0.13 mmol) and DIEA (40 mg, 0.31 mmol) in anhydrous $CH_2Cl_2$ (2 mL) at room temperature for 6 h. Allyl bromide then was removed by reduced pressure and the residue was washed by $H_2O$ to give the title compound after purification on a thin-layer silica-gel plate (20 cm×20 cm×2 mm) using $CH_2Cl_2$/MeOH (9:1) as the developing solution. $C_{16}H_{19}N_3O_2S$; white solid; mp 119-120° C.; IR $v_{max}$ (neat) 3072, 2920, 2857, 2801, 1717, 1653, 1448, 1339, 1262, 1234, 1136, 1038, 1000, 924, 748 cm$^{-1}$; $^1H$ NMR (400 MHz, $CDCl_3$) δ 8.02 (1H, d, J=8.0 Hz), 7.58 (1H, t, J=7.6 Hz), 7.53 (1H, d, J=8.0 Hz), 7.37 (1H, t, J=7.6 Hz), 5.80 (1H, m), 5.16 (2H, m), 4.69 (2H, s), 3.65 (2H, t, J=5.2 Hz), 3.57 (2H, t, J=5.2 Hz), 2.99 (2H, d, J=6.8 Hz), 2.45 (4H, m); $^{13}C$ NMR (100 MHz, $CDCl_3$) δ 165.5, 164.7, 134.1, 132.0, 126.7, 125.3, 120.2, 118.5, 61.5, 52.9, 52.5, 45.3, 44.8 (2×), 42.2, 29.8; ESI-HRMS calcd for $C_{16}H_{20}N_3O_2S$: 318.1274. found: m/z 318.1274 [M+H]$^+$.

2-(2-Oxo-2-(piperazin-1-yl)ethyl)benzo[d]isothiazol-3(2H)-one 1,1-dioxide (16)

Compound 17 (39 mg, 0.10 mmol) and trifluoroacetic acid (TFA, 1 mL, 13.2 mmol) was dissolved in anhydrous $CH_2Cl_2$ (2 mL), and then stirred for 2 h at 27° C. TFA was removed under reduced pressure, and the residue was washed with ethyl ether to give product 37 (45.3 mg, 100% yield). $C_{13}H_{15}N_3O_4S$; white oil; $^1H$ NMR (400 MHz, $CDCl_3$) δ 8.10 (2H, m), 8.01 (1H, td, J=7.6, 1.2 Hz), 7.96 (1H, td, J=7.6, 1.2 Hz), 4.78 (2H, s), 3.91 (2H, br s), 3.84 (2H, br s), 3.36 (2H, br s), 3.27 (2H, br s); $^{13}C$ NMR (100 MHz, $CD_3OD$) δ 165.7, 160.6, 139.2, 136.6, 136.0, 128.2, 126.2, 122.3, 67.0, 44.4, 43.2 (2×), 40.5; ESI-HRMS calcd for $C_{13}H_{16}N_3O_4S$: 310.0862. found: m/z 310.0865 $[M+H]^+$.

Tert-butyl 4-(2-(3-oxobenzo[d]isothiazol-2(3H)-yl) acetyl)piperazine-1-carboxylate 1,1-dioxide (17)

Saccharin (compound 2, 200 mg, 1.09 mmol) was added to a suspension of tert-butyl 4-(2-iodoacetyl)piperazine-1-carboxylate (343 mg, 0.97 mmol), DIEA (382 mg, 2.98 mmol) in anhydrous $CH_2Cl_2$ (5 mL) at room temperature. The mixture was stirred for 23 h, and washed successively with 1 M $HCl_{(aq)}$ and saturated $NaHCO_{3(aq.)}$. The organic phase was dried over $MgSO_4$, filtered, concentrated, and purified by flash chromatography on a silica gel column with elution of EtOAc/hexane (1:1.5) to give the title compound (159 mg, 40% yield). $C_{18}H_{23}N_3O_6S$; white solid; mp 178-181° C.; TLC (EtOAc/hexane=1:1.5) $R_f$=0.2; IR $v_{max}$ (neat) 3193, 2974, 2929, 2851, 1743, 1689, 1663, 1459, 1428, 1330, 1238, 1181, 1126, 1057, 999, 973, 877 $cm^{-1}$; $^1H$ NMR (400 MHz, $CDCl_3$) δ 8.05 (1H, d, J=7.6 Hz), 7.91 (1H, d, J=8.0 Hz), 7.83 (2H, m), 4.51 (2H, s), 3.58 (2H, m), 3.51 (2H, s), 3.49 (2H, s) 3.44 (2H, m), 2.24 (2H, m), 1.54 (9H, s); $^{13}C$ NMR (100 MHz, $CDCl_3$) δ 162.5, 159.0, 154.2, 137.6, 134.8, 134.2, 127.1, 125.3, 121.0, 80.4, 44.8 (2×), 42.2 (2×), 39.8, 28.4 (3×); ESI-HRMS calcd for $C_{18}H_{24}N_3O_6S$: 410.1386. found: m/z 410.1396 $[M+H]^+$.

Tert-Butyl 4-[2-(1,3-dioxo-1,3-dihydro-isoindol-2-yl)-acetyl]-piperazine-1-carboxylate (18)

Phthalimide (33 mg, 0.23 mmol) was treated with tert-butyl 4-(2-chloroacetyl)piperazine-1-carboxylate (80.5 mg, 0.32 mmol), tetrabutylammonium iodide (TBAI, 84 mg, 2.3 mmol), diisopropylethylamine (DIEA, 0.20 mg, 1.14 mmol) in anhydrous $CH_2Cl_2$ (10 mL) for 24 h at 40° C. The mixture was partitioned between $CH_2Cl_2$ and water. The organic phase was separated, dried over $MgSO_4$, filtered, concentrated, and purified by flash chromatography on a silica gel column with elution of EtOAc/hexane (1:1) to give the title compound (57.1 mg, 67% yield). $C_{19}H_{23}N_3O_5$; white solid; TLC (EtOAc/hexane=1:1) $R_f$=0.2; $^1H$ NMR (400 MHz, $CDCl_3$) δ 7.85-7.87 (2H, m), 7.70-7.72 (2H, m), 4.49 (2H, s), 3.51-3.57 (6H, m), 3.44 (2H, d, J=5.2 Hz), 1.46 (9H, d, J=4.8 Hz).

4,6-Dimethyl-2-(2-morpholino-2-oxoethyl)isothiazolo[5,4-b]pyridin-3(2H)-one (19)

Chloroacetyl chloride (840 mg, 6.89 mmol) was added to a solution of morpholine (500 mg, 5.74 mmol) in anhydrous $CH_2Cl_2$ (25 mL) containing $Et_3N$ (1.74 g, 17.22 mmol) at 0° C. The mixture was stirred and warmed to 27° C. for 2 h. The mixture was washed with 1 M $HCl_{(aq)}$. The organic phase was dried over $MgSO_4$, and concentrated under reduced pressure to give 2-chloro-1-morpholinoethanone (1.13 g, 100% yield). $C_6H_{11}ClNO_2$; brown oil; $^1H$ NMR (400 MHz, $CDCl_3$) δ 4.05 (2H, s), 3.69 (4H, m), 3.62 (2H, m), 3.52 (4H, m); $^{13}C$ NMR (100 MHz, $CDCl_3$) δ 164.4, 66.5, 66.4, 46.8, 42.5, 40.8; ESI-HRMS calcd for $C_6H_{12}ClNO_2$: 164.0478. found: m/z 164.0478 $[M+H]^+$.

The above-prepared chloro compound (225 mg, 1.25 mmol) was added to a suspension of pyridinothiazolone 4 (200 mg, 1.22 mmol), $Et_3N$ (370 mg, 3.66 mmol) in anhydrous $CH_2Cl_2$ (25 mL) to reflux (40° C.). The mixture was stirred for 24 h, and washed with 1 M $HCl_{(aq)}$. The organic phase was dried over $MgSO_4$, filtered, concentrated, and purified by flash chromatography on a silica gel column with elution of EtOAc/hexane (1:1) to give the title compound (211 mg, 55% yield) accompanied by an O-alkylation side product (9%). The purity of product 19 was 97.3% as shown by HPLC on an HC-C18 column (Agilent, 4.6×250 mm, 5 μM), $t_R$=11.9 min (gradients of 20-90% aqueous $CH_3CN$ in 20 min). $C_{14}H_{17}N_3O_3S$; white solid; mp 200-203° C.; IR $v_{max}$ (neat) 3490, 2921, 2851, 1704, 1651, 1467, 1275, 1111, 1036, 750 $cm^{-1}$; $^1H$ NMR (400 MHz, $CDCl_3$) δ 6.91 (1H, s), 4.62 (2H, s), 3.67 (4H, m), 3.62 (2H, m), 3.54 (2H, m), 2.70 (3H, s), 2.58 (3H, s); $^{13}C$ NMR (100 MHz, $CDCl_3$) δ 164.8, 164.8, 163.2, 162.9, 149.8, 122.5, 114.0, 66.7, 66.4, 45.5, 44.1, 42.5, 25.0, 17.6; ESI-HRMS calcd for $C_{14}H_{18}N_3O_3S$: 308.1069. found: m/z 308.1071 $[M+H]^+$.

4,6-Dimethyl-2-(2-oxo-2-(piperazin-1-yl)ethyl) isothiazolo[5,4-b]pyridin-3(2H)-one (20)

Compound 22 (20 mg, 0.05 mmol) and TFA (4 mL, 52.6 mmol) was dissolved in anhydrous $CH_2Cl_2$ (15 mL), and then stirred for 0.5 h at 27° C. TFA was removed under reduced pressure, and the residue was extracted with ammonia solution (35%) and $CH_2Cl_2$. The organic layer was dried over $MgSO_4$, filtered, and concentrated to give the title compound (16 mg, 100% yield). The purity of product was 95.2% as shown by HPLC on an HC-C18 column (Agilent, 4.6×250 mm, 5 μM), $t_R$=16.6 min (gradients of 20-90% aqueous $CH_3CN$ in 20 min). $C_{14}H_{18}N_4O_2S$; white solid; mp 175-177° C.; IR $v_{max}$ (neat) 3475, 3310, 2925, 1652, 1565, 1443, 1337, 1275, 1033, 750 $cm^{-1}$; $^1H$ NMR (400 MHz, $CDCl_3$) δ 6.92 (1H, S), 4.64 (2H, s), 3.62 (2H, m), 3.53 (2H, m), 2.88 (4H, m), 2.72 (3H, s), 2.59 (3H, s), 2.04 (1H, s); $^{13}C$ NMR (100 MHz, $CDCl_3$) δ 164.4, 164.1, 162.9, 162.4, 149.4, 122.6, 113.9, 46.5, 46.3, 45.9, 44.4, 43.5, 24.9, 17.9; ESI-HRMS calcd for $C_{14}H_{19}N_4O_2S$: 307.1229. found: m/z 307.1227 $[M+H]^+$.

Ethyl 4-(2-(4,6-dimethyl-3-oxoisothiazolo[5,4-b] pyridin-2(3H)-yl)acetyl) piperazine-1-carboxylate (21, YMU1)

A mixture of acid 9 (420 mg, 1.76 mmol) and piperazine-1-carboxylic acid ethyl ester (279 mg, 1.76 mmol) was treated with 1-ethyl-3-(3-dimethylaminopropyl) carbodiimide (EDCI, 370 mg, 1.1 mmol), 4-dimethylaminopyridine (DMAP, catalytic amount), diisopropylethylamine (DIEA, 186 mg, 5.28 mmol) in anhydrous $CH_2Cl_2$ (50 mL). The mixture was stirred under an atmosphere of nitrogen for 16 h at 27° C. The mixture was partitioned with $H_2O$ and 1 M $HCl_{(aq)}$. The organic phase was dried over $MgSO_4$, filtered and concentrated under reduced pressure. Flash chromatography (eluent: EtOAc/hexane=1.5:1) of the residue gave 430 mg (65% yield) of the title compound (YMU1), which was recrystallized from EtOAc. The purity of product was 95.7% as shown by HPLC on an HC-C18 column (Agilent, 4.6×250 mm, 5 μM), $t_R$=9.35 min (gradients of 30-90% aqueous $CH_3CN$ in 40 min).

Alternatively, pyridinothiazolone 4 (300 mg, 1.66 mmol) was treated with ethyl 4-(2-iodoacetyl)piperazine-1-carboxylate (541 mg, 1.66 mmol), $Et_3N$ (840 mg, 8.30 mmol) and $Cs_2CO_3$ (500 mg, 1.54 mmol) in anhydrous $CH_2Cl_2$ (25 mL) at room temperature for 24 h, and then washed with $H_2O$. The organic layer was dried over $MgSO_4$, filtered, concentrated, and purified by flash chromatography on a silica gel column (EtOAc/hexane (1:1)) to give the title compound (60% yield) in addition to the O-alkylation product 28 (11%).

Compound 21: $C_{17}H_{22}N_4O_4S$; white powder; mp 238-240° C.; TLC (EtOAc/hexane=3:1) $R_f$=0.45; $^1H$ NMR (400

MHz, CD$_3$OD) δ 6.93 (1H, s), 4.65 (2H, s), 4.15 (2H, q, J=6.8 Hz), 3.61 (2H, m), 3.52 (4H, s), 3.49 (2H, m), 2.72 (3H, s), 2.59 (3H, s), 1.26 (3H, t, J=7.6 Hz); $^{13}$C NMR (100 MHz, CD$_3$OD) δ 164.41, 164.31, 162.73, 162.49, 154.61, 149.43, 122.23, 113.74, 61.85, 45.13, 44.45, 43.56 (2×), 42.15, 24.90, 17.85, 14.90; ESI-HRMS calcd for C$_{17}$H$_{23}$N$_4$O$_4$S: 279.1440. found: m/z 279.1446 [M+H]$^+$.

Tert-butyl 4-(2-(4,6-dimethyl-3-oxoisothiazolo[5,4-b]pyridin-2(3H)-yl)acetyl) piperazine-1-carboxylate (22)

A mixture of tert-butyl 4-(2-chloroacetyl)piperazine-1-carboxylate (150 mg, 0.57 mmol) and sodium iodide (260 mg, 1.73 mmol) in acetone (6 mL) was stirred at room temperature for 21 h, and then the reaction mixture turned to a suspension containing white solid. The solids were eliminated by filtration, and the filtrate was dried to vacuo and washed with CH$_2$Cl$_2$ and H$_2$O. The organic layer then dried over MgSO$_4$, filtered and concentrated to give tert-butyl 4-(2-iodoacetyl)piperazine-1-carboxylate (164.4 mg, 84.4% yield). C$_{11}$H$_{19}$I$_1$N$_2$O$_3$; brown solid; mp 69-71° C.; IR ν$_{max}$ (neat) 2976, 2926, 2861, 1696, 1650, 1459, 1419, 1366, 1258, 1168, 1028, 996, 750 cm$^{-1}$; $^1$H NMR (400 MHz, CDCl$_3$) δ 3.76 (2H, s), 3.57 (2H, m), 3.51 (2H, m), 3.41 (4H, m) 1.47 (9H, s); $^{13}$C NMR (100 MHz, CDCl$_3$) δ 166.5, 154.2, 80.4, 47.0, 43.0 (2×), 41.9 (2×), 28.4 (3×).

Pyridinothiazolone 4 (300 mg, 1.66 mmol) was added to a suspension of the above-prepared iodo compound (578 mg, 1.66 mmol), Et$_3$N (840 mg, 8.30 mmol) and Cs$_2$CO$_3$ (500 mg, 1.54 mmol) in anhydrous CH$_2$Cl$_2$ (25 mL) at room temperature. The mixture was stirred for 24 h, and concentrated under reduced pressure. The residue was extracted with CH$_2$Cl$_2$ and H$_2$O. The organic phase was dried over MgSO$_4$, filtered, concentrated, and purified by flash chromatography on a silica gel column with elution of EtOAc/hexane (1:1) to give the title compound (400 mg, 59% yield). The purity of product was 98.4% as shown by HPLC on an HC-C18 column (Agilent, 4.6×250 mm, 5 μM), t$_R$=8.1 min (gradients of 40-90% aqueous CH$_3$CN in 15 min). C$_{19}$H$_{26}$N$_4$O$_4$S; white solid; mp 204-207° C.; IR ν$_{max}$ (neat) 3473, 2974, 2924, 1655, 1588, 1564, 1460, 1419, 1365, 1286, 1238, 1169, 1127, 1033, 997, 765 cm$^{-1}$; $^1$H NMR (400 MHz, CDCl$_3$) δ 6.89 (1H, s), 4.62 (2H, s), 3.56 (2H, m), 3.47 (2H, m), 3.41 (4H, m), 2.67 (3H, s), 2.55 (3H, s), 1.42 (9H, s); $^{13}$C NMR (100 MHz, CDCl$_3$) δ 164.8, 164.7, 163.1, 162.9, 154.1, 149.7, 122.4, 113.9, 80.35, 45.0, 44.3, 43.1 (2×), 42.0, 28.4 (3×), 24.6, 17.5; ESI-HRMS calcd for C$_{19}$H$_{26}$N$_4$O$_4$S: 407.1753. found: m/z 407.1756 [M+H]$^+$.

Ethyl 4-(4-(3-oxobenzo[d]isothiazol-2(3H)-yl)butanoyl)piperazine-1-carboxylate (23)

Ethyl piperazine-1-carboxylate (800 mg, 5.06 mmol) was treated with 4-chlorobutanoyl chloride (856 mg, 6.07 mmol) in anhydrous CH$_2$Cl$_2$ (25 mL) containing Et$_3$N (1.54 kg, 15.17 mmol) at 20° C. for 2 h, and then washed with 1 M HCl$_{(aq)}$. The organic phase was dried over MgSO$_4$, and concentrated under reduced pressure to give ethyl 4-(4-chlorobutanoyl)piperazine-1-carboxylate (1.315 kg, 99% yield). C$_{11}$H$_{19}$ClN$_2$O$_3$; pale yellow oil; $^1$H NMR (400 MHz, CDCl$_3$) δ 4.13 (2H, q, J=7.2 Hz), 3.62 (2H, t, J=5.6 Hz), 3.58 (2H, m), 3.46 (6H, m) 2.49 (2H, t, J=6.8 Hz), 2.11 (2H, m), 1.25 (3H, t, J=7.2 Hz); $^{13}$C NMR (100 MHz, CDCl$_3$) δ 170.1, 155.1, 61.7, 45.2, 44.8, 43.7 (2×), 41.4, 29.8, 27.8, 14.7; ESI-HRMS calcd for C$_{11}$H$_{20}$ClN$_2$O$_3$: 263.1162. found: m/z 263.1175 [M+H]$^+$.

The above-prepared chloro compound (664 mg, 2.53 mmol) was treated with sodium iodide (1.14 kg, 7.59 mmol) in acetone (8 mL). The mixture was stirred at room temperature for 21 h to give a suspension containing white solid. The solids were removed by filtration, and the filtrate was dried in vacuo. The residue was partitioned between CH$_2$Cl$_2$ and H$_2$O. The organic layer was dried over MgSO$_4$, filtered and concentrated to give ethyl 4-(4-iodobutanoyl)piperazine-1-carboxylate (654.5 mg, 73% yield). C$_{11}$H$_{19}$I$_1$N$_2$O$_3$; yellow oil; $^1$H NMR (400 MHz, CDCl$_3$) δ 4.14 (2H, q, J=7.2 Hz), 3.61 (2H, t, J=5.2 Hz), 3.59 (2H, m), 3.45 (6H, m) 2.51 (2H, t, J=7.0 Hz), 2.11 (2H, m), 1.26 (3H, t, J=6.8 Hz); $^{13}$C NMR (100 MHz, CDCl$_3$) δ 170.1, 155.1, 61.7, 45.2, 44.8, 43.6 (2×), 41.4, 29.8, 27.8, 14.7.

Benzothiazolone 1 (291 mg, 1.92 mmol) was treated with the above-prepared iodo compound (650 mg, 1.83 mmol) and DIEA (712 mg, 5.51 mmol) in anhydrous CH$_2$Cl$_2$ (10 mL) at room temperature. The mixture was stirred for 17 h, and washed successively with 1 M HCl$_{(aq)}$ and saturated NaHCO$_{3(aq)}$. The organic phase was dried over MgSO$_4$, filtered, concentrated, and purified by flash chromatography on a silica gel column with elution of EtOAc/hexane (1:1) to give the title compound (350 mg, 50% yield). C$_{18}$H$_{23}$N$_3$O$_4$S; oil; TLC (EtOAc/hexane=2:1) R$_f$=0.6; IR ν$_{max}$ (neat) 2987, 2923, 1698, 1645, 1509, 1464, 1428, 1346, 1260, 1233, 1021, 750 cm$^{-1}$; $^1$H NMR (400 MHz, CDCl$_3$) δ 7.85 (2H, d, J=8.0 Hz), 7.73 (2H, d, J=8.0 Hz), 7.48 (2H, t, J=7.2 Hz), 7.35 (2H, t, J=7.2 Hz), 4.58 (2H, d, J=5.6 Hz), 4.13 (2H, q, J=3.6 Hz), 3.61 (2H, m), 3.44 (6H, m) 2.54 (2H, t, J=7.6 Hz), 2.24 (2H, m), 1.50 (3H, t, J=6.4 Hz); $^{13}$C NMR (100 MHz, CDCl$_3$) δ 170.5, 162.7, 155.1, 151.4, 128.5, 125.1, 124.2, 122.7, 120.0, 67.9, 61.7, 45.2, 43.6 (2×), 41.4, 29.7, 24.8, 14.7; ESI-HRMS calcd for C$_{18}$H$_{24}$N$_3$O$_4$S: 378.1488. found: m/z 378.1493 [M+H]$^+$.

2,2'-(2,2'-(piperazine-1,4-diyl)bis(2-oxoethane-2,1-diyl))dibenzo[d]isothiazol-3(2H)-one (24)

Chloroacetyl chloride (892 mg, 7.31 mmol) was added to a solution of piperazine (300 mg, 3.48 mmol) in anhydrous CH$_2$Cl$_2$ (12 mL) containing Et$_3$N (1.41 kg, 13.93 mmol) at 0° C. The mixture was stirred and warmed to 27° C. for 1 h. The mixture was washed with 1 M HCl$_{(aq)}$. The organic phase was dried over MgSO$_4$, and concentrated under reduced pressure to give 1,1'-(piperazine-1,4-diyl)-bis(2-chloroethanone) (750 mg, 90% yield). C$_8$H$_{12}$Cl$_2$N$_2$O$_2$; white solid; mp 104-107° C.; $^1$H NMR (400 MHz, CDCl$_3$) δ 4.08 (4H, s), 3.69 (2H, m), 3.62 (4H, d, J=8.0 Hz), 3.55 (2H, m); $^{13}$C NMR (100 MHz, CDCl$_3$) δ 165.2 (2×), 46.2, 45.8, 42.1, 41.7, 40.7 (2×).

A mixture of the above-prepared 1,1'-(piperazine-1,4-diyl)-bis(2-chloroethanone) (750 mg, 3.14 mmol) and sodium iodide (1.88 kg, 12.54 mmol) in acetone (10 mL) was stirred at room temperature for 16 h to give a suspension containing white solids. The solids were removed by filtration, and the filtrate was dried in vacuo. The residue was partitioned between CH$_2$Cl$_2$ and H$_2$O. The organic layer was dried over MgSO$_4$, filtered and concentrated to give 1,1'-(piperazine-1,4-diyl)-bis(2-iodoethanone) (210 mg, 16% yield). C$_8$H$_{12}$I$_2$N$_2$O$_2$; dark brown solid; mp 105-109° C.; IR ν$_{max}$ (neat) 3003, 2922, 2853, 1708, 1637, 1439, 1258, 1225, 1161, 1092, 1023, 983, 737 cm$^{-1}$; $^1$H NMR (400 MHz, CDCl$_3$) δ 3.76 (4H, s), 3.73 (2H, m), 3.62 (2H, s), 3.57 (2H, s), 3.46 (2H, m); $^{13}$C NMR (100 MHz, CDCl$_3$) δ 166.6, 166.4, 46.5, 46.3, 41.5, 41.4, 29.7 (2×).

Benzothiazolone 1 (160 mg, 1.06 mmol) was treated with the above-prepared diiodo compound (200 mg, 0.47 mmol) and DIEA (368 mg, 2.85 mmol) in anhydrous CH$_2$Cl$_2$ (5 mL)

at room temperature. The mixture was stirred for 26 h, and washed successively with 1 M HCl$_{(aq)}$ and saturated NaHCO$_{3(aq.)}$. The organic phase was dried over MgSO$_4$, filtered, concentrated, and purified by flash chromatography on a silica gel column with elution of CH$_2$Cl$_2$/MeOH (100:2.5) to give the title compound (225 mg, 48% yield). C$_{22}$H$_{20}$N$_4$O$_4$S$_2$; white solid; mp 269-271° C. (decomposed); $^1$H NMR (400 MHz, CDCl$_3$) δ 7.95 (2H, d, J=8.0 Hz), 7.87 (2H, d, J=8.0 Hz), 7.69 (2H, t, J=8.0 Hz), 7.43 (2H, t, J=8.0 Hz), 4.81 (2H, s), 4.79 (2H, s), 3.62 (2H, br s), 3.55 (4H, br s); $^{13}$C NMR (100 MHz, CDCl$_3$) δ 165.2 (2×), 165.1 (2×), 141.5 (2×), 132.1 (2×), 125.7 (2×), 125.5 (2×), 123.5 (2×), 121.8 (2×), 44.5 (2×), 43.8 (2×), 41.2 (2×); ESI-HRMS calcd for C$_{22}$H$_{21}$N$_2$O$_4$S$_2$: 469.1004. found: m/z 469.1004 [M+H]$^+$.

Methyl 2-(4,6-dimethylisothiazolo[5,4-b]pyridin-3-yloxy)acetate (25)

A mixture of pyridinothiazolone 4 (500 mg, 2.77 mmol), methyl 2-bromoacetate (900 mg, 5.88 mmol), Cs$_2$CO$_3$ (700 mg, 3.07 mmol) and DIEA (1.5 mL, 8.61 mmol) in anhydrous CH$_2$Cl$_2$ (20 mL) was stirred at room temperature for 5 h, and then concentrated under reduced pressure. In addition to the main N-alkylation product 7 (55%), the title compound (50 mg, 7% yield) was obtained after purification by flash chromatography on a silica gel column (EtOAc/hexane (1:4)). C$_{11}$H$_{12}$N$_2$O$_3$S; white solid; mp 89-91° C.; IR v$_{max}$ (neat) 3053, 2958, 2929, 2851, 1767, 1592, 1562, 1504, 1445, 1398, 1334, 1228, 1128, 1039, 961 cm$^{-1}$; $^1$H NMR (400 MHz, CDCl$_3$) δ 6.91 (1H, s), 5.05 (2H, s), 3.78 (3H, s), 2.89 (3H, s), 2.61 (3H, s); $^{13}$C NMR (100 MHz, CDCl$_3$) δ 172.3, 168.4, 160.7, 160.2, 145.6, 121.4, 115.7, 64.2, 52.3, 24.6, 19.1; ESI-HRMS calcd for C$_{11}$H$_{13}$N$_2$O$_3$S: 253.0647. found: m/z 253.0647 [M+H]$^+$.

2-(4,6-Dimethylisothiazolo[5,4-b]pyridin-3-yloxy) acetic acid (26)

Ester 25 (150 mg, 0.59 mmol) was suspended in conc. HCl (3 mL) and heated with stirring at 100° C. for 5 h until hydrolysis completed. The mixture was cooled to room temperature, diluted with water (350 mL), and the precipitate was collected to give the title compound (138 mg, 98% yield). C$_{10}$H$_{10}$N$_2$O$_3$S; white solid; mp 270° C. (decomposed); IR v$_{max}$ (neat) 3423, 2928, 1716, 1591, 1504, 1440, 1392, 1363, 1308, 1204, 1125, 1038, 985, 862 cm$^{-1}$; $^1$H NMR (400 MHz, DMSO-d$_6$) δ 7.20 (1H, s), 5.03 (2H, s), 2.66 (3H, s), 2.58 (3H, s); $^{13}$C NMR (100 MHz, DMSO-d$_6$) δ 171.0, 169.0, 160.9, 160.6, 145.3, 121.7, 115.1, 64.4, 24.1, 14.4; ESI-HRMS (negative mode) calcd for C$_{10}$H$_6$N$_2$O$_3$S: 237.0334. found: m/z 237.0332 [M–H]$^-$.

2-(4,6-Dimethylisothiazolo[5,4-b]pyridin-3-yloxy)-1-morpholinoethanone (27)

Pyridinothiazolone 4 (200 mg, 1.22 mmol), was treated with 2-chloro-1-morpholinoethanone (225 mg, 1.25 mmol) and Et$_3$N (370 mg, 3.66 mmol) in anhydrous CH$_2$Cl$_2$ (25 mL) at reflux (40° C.) for 24 h, and then washed with 1 M HCl$_{(aq)}$. The organic phase was dried over MgSO$_4$, filtered, concentrated, and purified by flash chromatography on a silica gel column with elution of EtOAc/hexane (1:1) to give the title compound (35 mg, 9% yield) in addition to the main N-alkylation product 19 (55%).

Alternatively, the coupling reaction of acid 26 with morpholine in the presence of EDCI, DMAP and DIEA, by a procedure similar to that for compound 21 (YMU1), gave compound 27 in 82% yield.

Compound 27: C$_{14}$H$_{17}$N$_3$O$_3$S; white solid; mp 153-155° C.; IR v$_{max}$ (neat) 3488, 2923, 2853, 1665, 1591, 1498, 1443, 1378, 1333, 1273, 1239, 1115, 1018 cm$^{-1}$; $^1$H NMR (400 MHz, CDCl$_3$) δ 6.93 (1H, S), 5.16 (2H, s), 3.90 (6H, m), 3.51 (2H, 3), 2.71 (3H, s), 2.61 (3H, s); $^{13}$C NMR (100 MHz, CDCl$_3$) δ 172.3, 165.4, 160.7, 160.5, 145.7, 121.5, 115.8, 66.8, 66.4, 64.9, 45.3, 42.2, 24.6, 19.1; ESI-HRMS calcd for C$_{14}$H$_{18}$N$_3$O$_3$S: 308.1069. found: m/z 308.1070 [M+H]$^+$.

Ethyl 4-(2-(4,6-dimethylisothiazolo[5,4-b]pyridin-3-yloxy)acetyl)piperazine-1-carboxylate (28)

piperazine-1-carboxylic acid ethyl ester (200 mg, 1.26 mmol) was treated with chloroacetyl chloride (186 mg, 1.65 mmol) in anhydrous CH$_2$Cl$_2$ (10 mL) containing DIEA (490 mg, 3.80 mmol) at 0° C. The mixture was stirred and warmed to 27° C. for 4 h. The mixture was washed with 1 M HCl$_{(aq)}$. The organic phase was dried over MgSO$_4$, and concentrated under reduced pressure to give ethyl 4-(2-chloroacetyl)piperazine-1-carboxylate (275 mg, 93% yield). C$_9$H$_{15}$ClN$_2$O$_3$; transparent oil; $^1$H NMR (400 MHz, CDCl$_3$) δ 4.15 (2H, q, J=7.2 Hz) 4.06 (2H, s), 3.60 (2H, m), 3.54 (2H, m), 3.49 (4H, m), 1.27 (3H, t, J=7.2 Hz); $^{13}$C NMR (100 MHz, CDCl$_3$) δ 164.3, 154.3, 61.4, 45.8, 43.5, 43.1, 41.8, 40.8, 14.7; ESI-HRMS calcd for C$_9$H$_{16}$ClN$_2$O$_3$: 235.0849. found: m/z 235.0852 [M+H]$^+$.

A mixture of ethyl 4-(2-chloroacetyl)piperazine-1-carboxylate (2.36 g, 10.06 mmol) and sodium iodide (3 g, 20.11 mmol) in acetone (45 mL) was stirred at room temperature for 24 h to give a suspension containing white solids. The solids were removed by filtration, and the filtrate was concentrated under reduced pressure. The residue was extracted with CH$_2$Cl$_2$ and H$_2$O. The organic layer then dried over MgSO$_4$, filtered and concentrated to give ethyl 4-(2-iodoacetyl)piperazine-1-carboxylate (2.47 g, 75% yield). C$_9$H$_{15}$IN$_2$O$_3$; brown oil; IR v$_{max}$ (neat) 2981, 2927, 2864, 1697, 1642, 1464, 1434, 1385, 1286, 1232, 1133, 1073, 1030, 989, 767 cm$^{-1}$; $^1$H NMR (400 MHz, CDCl$_3$) δ 4.14 (2H, q, J=7.0 Hz), 3.75 (2H, s), 3.58 (4H, m), 3.43 (4H, m), 1.26 (3H, t, J=7.0 Hz); $^{13}$C NMR (100 MHz, CDCl$_3$) δ 166.6, 155.1, 61.8, 47.0, 43.1 (2×), 42.0 (2×), 14.7; ESI-HRMS calcd for C$_9$H$_{16}$IN$_2$O$_3$: 327.0206. found: m/z 327.0215 [M+H]$^+$.

Pyridinothiazolone 4 (300 mg, 1.66 mmol) was treated with ethyl 4-(2-iodoacetyl)piperazine-1-carboxylate (541 mg, 1.66 mmol), Et$_3$N (840 mg, 8.30 mmol) and Cs$_2$CO$_3$ (500 mg, 1.54 mmol) in anhydrous CH$_2$Cl$_2$ (25 mL) at room temperature for 24 h, and then washed with H$_2$O. The organic layer was dried over MgSO$_4$, filtered, concentrated, and purified by flash chromatography on a silica gel column (EtOAc/hexane (1:1)) to give the title compound (68 mg, 11% yield) in addition to the main N-alkylation product 21 (YMU1, 60%). The purity of product 28 was 99.5% as shown by HPLC on an HC-C18 column (Agilent, 4.6×250 mm, 5 μM), t$_R$=4.9 min (gradients of 40-90% aqueous CH$_3$CN in 15 min).

Pyridinothiazolone 4 (300 mg, 1.66 mmol) was treated with ethyl 4-(2-iodoacetyl)piperazine-1-carboxylate (541 mg, 1.66 mmol), Et3N (840 mg, 8.30 mmol) and Cs2CO3 (500 mg, 1.54 mmol) in anhydrous CH2Cl2 (25 mL) at room temperature for 24 h, and then washed with H2O. The organic layer was dried over MgSO4, filtered, concentrated, and purified by flash chromatography on a silica gel column (EtOAc/hexane (1:1)) to give the title compound (68 mg, 11% yield) in addition to the main N-alkylation product 21 (YMU1, 60%). The purity of product 28 was 99.5% as shown by HPLC on an HC-C18 column (Agilent, 4.6×250 mm, 5 μM), t R=4.9 min (gradients of 40-90% aqueous CH3CN in 15 min).

Compound 28: $C_{19}H_{26}N_4O_4S$; white solid; mp 88-90° C.; IR $v_{max}$ (neat) 2981, 2926, 2868, 1674, 1591, 1566, 1498, 1466, 1431, 1381, 1286, 1231, 1200, 1174, 1127, 1007 cm$^{-1}$; $^1$H NMR (400 MHz, CDCl$_3$) δ 6.93 (1H, s), 5.18 (2H, s) 4.15 (2H, q, J=7.2 Hz), 3.62 (2H, m), 3.51 (4H, m), 2.71 (3H, s), 2.62 (3H, s), 1.26 (3H, t, J=7.2 Hz); $^{13}$C NMR (100 MHz, CDCl$_3$) δ 171.84, 165.01, 160.36, 160.23, 154.70, 145.33, 121.27, 115.56, 65.06, 61.92, 44.91, 43.67 (2×), 41.98, 24.88, 19.46, 15.06; ESI-HRMS calcd for $C_{17}H_{22}N_4O_4S$: 401.1259. found: m/z 401.1260 [M+H]$^+$.

Construction of Lentiviral Vector

Using BLOCK-iT™ Lentiviral RNAi Expression System (Invitrogen) constructs lentiviral-based small hairpin RNA (shRNA). Nucleotides 509 to 527 of hTMPK open reading frame and nucleotides 1017 to 1036 in the 3'UTR of hTS gene were chosen as the target sequence. We synthesized one strand of oligonucleotide containing the target sequence followed by a 7-nucleotide short loop and sequence that was the reverse complement of the initial target sequence. The oligonucleotides in pairs were annealed and inserted into pEN-TRTM/U6 RNAi cassette to generate an entry construct. The LacZ double-stranded control oligo supplied in the kit was also cloned as a non-silencing (negative) control siRNA. The lentiviral constructs were then individually cloned by recombination of the U6 RNAi cassette into the pLenti6/BLOCK-iT™-DEST vector.

Lentiviral shRNA Production for Infection

293 FT producer cells (6×10$^6$ cells) were co-transfected with 9 μg of the ViraPower™ packaging Mix (containing a mixture of the pLP1, pLP2, and pLP/VSVG plasmid) and 3 μg of pLenti6 LacZ$^{shRNA}$, TMPK$^{shRNA}$, Ts$^{shRNA}$, pLKO-UNG$^{shRNA}$ or pLKO-dUTPase$^{shRNA}$ plasmid by lipofectamine 2000 (Invitrogene). At 72 h after transfection, 10 ml of supernatants containing lentivirus were collected and concentrated with Millipore concentration column to a final volume of 5 ml. The lentiviral LacZ$^{shRNA}$, TmpK$^{shRNA}$, TS$^{shRNA}$, UNG$^{shRNA}$ and dUTPase$^{shRNA}$ stocks in 1 ml of medium containing 8 μg/ml polybrene were used to infect 2.5×10$^6$ cells overnight, after which the supernatant were replaced with complete medium for the subsequent assays.

Luciferase-Coupled TMPK Assay

The TMPK reaction was started by adding purified hTMPK in 50 μl of TMPK assay buffer (100 mM Tris-HCl, pH 7.5, 100 mM KCl, 10 mM MgCl2, 50 μM ATP and 100 μM dTMP) in 96 wells plate at 25° C. for 10 min and terminated by adding 200 μl of DTNB (100 μM), followed by transferring 10 μl of reaction solution to a white 96-wellplate containing 90 μl of luciferase assay buffer (50 mM Glycine, 0.5 mM EDTA and 5 mM EDTA, pH 7.0, 0.1 μg of luciferase, 50 μM luciferin and 0.1% BSA). The luminescence was measured with a luminescence counter (Packard).

Luciferase-Coupled TK Assay

The TK reaction was started by adding purified hTMPK in 50 μl of TK assay buffer (50 mM Tris-HCl, pH 7.5, 1 mM CHAPS, 3 mg/ml BSA, 2.5 mM MgCl2, 50 μM ATP and 100 μM thymidine) in 96 wells plate at 25° C. for 10 min and terminated by adding 200 μl of thymidine (1.25 mM), followed by transferring 10 μl of reaction solution to a white 96-wellplate containing 90 μl of luciferase assay buffer (50 mM Glycine, 0.5 mM EDTA and 5 mM EDTA, pH 7.0, 0.1 μg of luciferase, 50 μM luciferin and 0.1% BSA). The luminescence was measured with a luminescence counter (Packard).

NADH-Coupled TMPK Assay

All reactions were performed in 96-well plates in an assay volume of 100 μl. The activity of hTMPK was measured at 25° C. using a modified NADH coupled colorimetric assay as described (Agarwal et al., 1978; Miyata et al., 2003; Ostermann et al., 2003), in which purified hTMPK was added to the buffer containing 100 mM Tris-HCl, pH 7.5, 100 mM KCl, 10 mM MgCl2, 0.5 mM phosphoenol pyruvate, 0.25 mM NADH, 5 units of lactate dehydrogenase, 4 units of pyruvate kinase, 1 mM ATP, and 200 μM dTMP. The change of NADH was measured by reading the absorbance at 340 nm. One unit of TMPK activity is defined as the conversion of 1 μmole of TMP to TDP per minute.

Expression and Purification of Enzymes pGEX-2T-hTMPK(Ke et al., 2005), pGEX-2T-hTMPK D15R, pGEX-2T-dUTPase (WT), pGEX-2T-dUTPase (KD-mutant), or pGEX-3X-hTK1 (Chang et al., 1998) was transformed in E. coli JM109 strain to produce GST-hTMPK and GST-dUTPase fusion protein by inducing with 0.1 mM isopropyl-13-D-thiogalactopyranoside (IPTG) at 37° C. for 4 hr. Bacteria were lysed by sonication, and cleared lysates were incubated with glutathione 4B beads (Amersham Pharmacia). After extensive washing with phosphate-buffered saline (PBS), hTMPK protein was cleaved from GST-fusion protein bound to glutathione beads by thrombin (Sigma) digestion at 4° C. overnight. Purified GST-dUTPase (WT) and GST-dUTPase (KD-mutant) fusion protein were eluted from glutathione-sepharose with glutathione after affinity chromatography.

dUTPase Activity Assay

For detecting dUTPase activity, the EnzChek Pyrophosphate Assay kit (Invitrogen) was used for measuring the dUTPase activity following the manufacturer's instruction. In brief, 0.25 μg of GST-dUTPase (WT) or GST-dUTPase (KD-mutant) protein were added to 200 μl of the reaction buffer [34 mM Tris-HCl pH 8.3, 10 mM MgCl2, 0.5 mM EDTA, 0.25 mg/ml bovine serum albumin (BSA, Sigma)] containing 0.3 mM dUTP. Reaction mixtures were incubated at 37° C. for 3 minutes. Samples (15 μl each) were added to the reaction mixtures [715 μl dH2O, 50 μl 20× reaction buffer, 200 μl MESG substrate, 1 U purine nucleoside phosphorylase, 0.03 U inorganic pyrophosphatase] and incubated at 22° C. for 45 minutes. The absorbance at 360 nm was measured using an ELISA plate reader.

Comet Assay

Alkaline comet assays were performed using a Trevigen's Comet Assay kit (4250-050-k) according to the manufacturer's instruction. DNA was stained with SYBR Green, and slides were photographed digitally (Olympus BX51 microscope and Olympus camera). Tail moments were analyzed using Scoin Image software.

Whole-Cell dTTP Extraction and Quantification

10$^6$ cells were extracted with 1 ml of ice-cold 60% methanol at −20° C. overnight, followed by centrifugation for 30 min at 16,000×g. The supernatant was immersed at 100° C. in dry bath for 3 min and dried under vacuum. The dry residue was dissolved in 80 μl of nuclease free water and used for cellular dNTP measurement according to the method described by Ferraro et al. (Ferraro et al., 2010).

Protein Extraction and Western Blotting Analysis

Cell extracts were prepared as described previously (Chang et al., 1998). Equal amounts of protein were resolved on SDS-PAGE (11% (w/v) gel) followed by electrophoretic transfer to PVDF membranes (Millipore). After blocking with 5% (w/v) powdered non-fat milk, the membrane was incubated with different antibodies for overnight at 4° C. and treated for 1 h with horseradish peroxidase-conjugated goat anti-rabbit IgG, goat anti-mouse, and donkey anti-goat antibodies (Santa Cruz). ECL detection for the horseradish peroxidase reaction was performed according to the manufacturer's instructions (PerkinElmer Life Sciences). Protein signal was determined by UVP BioSpectrum 500 Imaging System. Protein expression level was determined by GEL-PRO software.

RNA Isolation and RT-PCR

Total RNA was isolated from cells at the indicated times by using TRIzol reagent (Invitrogen). cDNA was synthesized using ImProm-II reverse transcriptase (Promega). The mRNA levels of UNG, TMPK, and GAPDH were evaluated by RT-PCR. The GAPDH gene was used as internal control gene. Primers were designed based on the nucleotide sequence of human UNG, hTMPK, and GAPDH as described in Table 4. The PCR mixture contained 1 µl of cDNA sample (50 ng), 1 µM forward and reverse primers, and 12.5 µl of GoTaq Green Master Mix, 2× (Promega), in a final volume of 25 µl. The PCR were performed with mod at 95° C. for 5 min and 25 cycles of amplification for 30 s at 95° C., 30 s at 55° C., and 30 s at 72° C., followed by 72° C. for 5 min and 4° C. for 10 min. PCR products were analyzed on 2% agarose gel and visualized by ethidium bromide staining.

was generated by introducing D102N mutation (Harris et al., 1999). pCMV2-YFP-Nuc-R1C was constructed by inserting cDNA covering C-terminal 701-792 amino acids of R1 subunit of RNR into the BamHI site of plasmid pCMV2-YFP-Nuc. Lentiviral expression vector of mCherry and mCherry R2 were generated by inserting cDNA of mCherry or mCherry-R2 into the NheI site of pLKO AS3w plasmid.

Homologous Recombination Assay

U2OS DR-GFP cells with the integrated homologous recombination reporter DR-GFP (Pierce et al., 1999) were transfected with TMPK siRNA followed by I-SceI expression vector (pCBA-I-SceI) expression for 48 h. The recombination efficiency was examined by flow cytometric analysis for measuring GFP+ frequencies.

Immunofluorescence Staining Analysis

For γH2AX, Rad51 and XRCC1 staining, cells were fixed with 4% paraformaldehyde for 30 min at room temperature and were incubated with TBS (50 mM Tris-HCl, pH 7.4, 150 mM NaCl) plus 0.3% Triton X-100 for 5 min. The coverslips

TABLE 4

| shRNA and siRNA targeting sequence | | |
|---|---|---|
| | Targeting Sequence | |
| LacZ shRNA | CTACACAAATCAGCGATTT | SEQ ID NO: 1 |
| TMPK shRNA | ACACGACTTTGAACTGGAA | SEQ ID NO: 2 |
| TS shRNA | GGATATTGTCAGTCTTTAGG | SEQ ID NO: 3 |
| UNG shRNA | GTCTACAGACATAGAGGATTT | SEQ ID NO: 4 |
| dUTPase shRNA | GCGCTCCCTTCTGGGTGTTAT | SEQ ID NO: 5 |
| R2 siRNA | ACCGGAAAGAAAATGCT | SEQ ID NO: 6 |
| Real-time PCR and RT-PCR primer | | |
| Description | Sequence | |
| Oligos for Real-Time PCR repair assay: | | |
| I-PpoI site at Chromosome I | 5'-TCACTGAAGACTTGGTGGGA-3' | SEQ ID NO: 7 |
| (flanking the I-PpoI site) | 5'-AAACCATACGTGGCAGAGTG-3' | SEQ ID NO: 8 |
| GAPDH site | 5'-GCTTGCCCTGTCCAGTTAAT-3' | SEQ ID NO: 9 |
| | 5'-TAGCTCAGCTGCACCCTTTA-3' | SEQ ID NO: 10 |
| Oligos for RT-PCR | | |
| UNG gene | 5'-TCGTGCCCATCAAGCCAACT-3' | SEQ ID NO: 11 |
| | 5'-GGGAGGGATGAGCCGTCTGT-3' | SEQ ID NO: 12 |
| TMPK gene | 5'-AAATCGCTGGGAACAAGTGCCGT-3' | SEQ ID NO: 13 |
| | 5'-TTTGGGAAGGCCCACGTCTGG-3' | SEQ ID NO: 14 |
| GAPDH gene | 5'-CCATGTTCGTCATGGGTGT-3' | SEQ ID NO: 15 |
| | 5'-CCAGGGGTGCTAAGCAGTT-3' | SEQ ID NO: 16 |

Construction of Expression Plasmids and Site-Directed Mutagenesis pEGFP-hTMPK was constructed by insertion of hTMPK cDNA at HindIII site of pEGFP-N1 (Clontect). pEGFP-hTMPK (D15R) mutant were generated by using QuickChange XL site-directed mutagenesis kit (Stratagene). Expression vector of mCherry-R2 was generated by inserting cDNA of R2 into the Bgl II site of mCherry plasmid. pEGFP-dUTPase (WT) was generated by in-frame insertion of the nuclear form of dUTPase cDNA at the EcoRI-BamHI site of pEGFP-C1 (Clontech). Catalytic-dead (KD) mutant of pEGFP-dUTPase were blocked with MAXblock™ (Active Motif) for 1 h at 37° C., followed by staining with primary antibodies: anti-γH2AX monoclonal antibody (1:1000), anti-Rad51 polyclonal antibody (1:500) or anti-XRCC1 monoclonal antibody (1:500) overnight at 4° C. After extensive washing, cells were stained with secondary antibodies and Hoechst 33342 for 1 h at room temperature. After mounting, cells were analyzed and photographed with a Carl Zeiss fluorescence microscope equipped with AxioCam digital camera and Axio Vision Rel. 4.8 imaging software.

Quantitative Chromatin Immunoprecipitation Assay

HEK293T cells ($1\times10^7$) were transfected with pEGFP-I-Ppol expression vector. After transfection for 18 h, cells were crosslinked with formaldehyde at a final concentration of 1% at room temperature for 10 min and ChIP was performed as described (Berkovich et al., 2007). Precipitated DNA was re-suspended in 50 µl of TE buffer and analyzed by quantitative real-time PCR with the ABI StepOne system using Fast SYBR Green PCR Master Mix (Applied Biosystems). Sequences of primers near the I-Ppol site in chromosome I and GAPDH were described in Table 4.

Laser-Micro-Irradiation and Protein Localization at the DNA Damage Site

Cells were seeded at the appropriated density on glass-bottomed dishes. Cells stained with 2 µg/ml Hochest 33342 for 10 min. Laser micro-irradiation was carried out with a FluoView 1000 confocal microscope (Olympus) and a 405 nm laser diode (fast mode, SIM scanner, 250 msec). For γH2AX, endogenous TMPK and R2 co-staining, cells were washed with CSK buffer (100 mM NaCl, 300 mM sucrose, 10 mM PIPES pH 7.0, 3 mM $MgCl_2$) containing 0.1% of Triton X-100 for 5 min prior to fixation with 2% of paraformaldehyde for 15 min.

TMPK Inhibitor Screening

Luciferase-coupled TMPK assay (Hu and Chang, 2010) was modified and used to screen 21,120 structurally diversified compounds selected from ChemDiv library (San Deigo, USA). These compounds were dissolved in DMSO and 10 µM of each was transferred to a well of 1536-well plates containing 0.25 µg of purified hTMPK protein in a final volume of 4 µl. 5,5-dithio-bis(2-nitrobezoic acid) (DTNB) at final concentration of 10 µM was used as the positive control for TMPK inhibition (Huang et al., 1994). After pre-incubation for 30 min, TMPK reaction was initiated by adding 4 µl of assay buffer containing 100 mM Tris-HCl, pH 7.5, 100 mM KCl, 10 mM MgCl2, 5 µM ATP and 20 µM dTMP for 10 min, followed by addition of 4 µl of luciferase assay buffer (50 mM Glycine, 0.5 mM EDTA and 5 mM EDTA, pH 7.0, 0.1 µg of luciferase, 25 µM luciferin and 0.1% BSA) to each well. Luminescence was acquired by ViewLux detectors (PerkinElmer) and actives of TMPK inhibition were judged by comparing with the positive control.

Molecular Docking

The initial structure of the TMPK was taken from PDB 1E2D and subjected to energy minimization. YMU1 was built and the charge was assigned using Gaussian03 package. AutoDock program was used to identify the binding sites and study the interaction of the YMU1 with the TMPK. Herein, MD simulation was performed by the NAMD program with the CHARMM27 force field. Finally, the system was then subjected to MD simulation to analyze the binding affinity. The non-bonded interactions between TMPK and YMU1 were evaluated to search for the optimized position.

In Vivo Chemotherapy

Female BALB/c AnN.Cg-Foxnl$^{nu}$/Crl Nurl mice 6-8 weeks of age (National Laboratory Animal Center, Taiwan) were used for the tumor xenograft model. HCT-116 p53−/− cells ($1\times10^6$) were subcutaneously implanted in the right flank of each mouse. Treatment began when the tumor was about 0.5-1 mm in diameter. Mice (n=32) were randomly allocated to four groups: Vehicle, 15% TEG; doxorubicin (1.25 mg/kg twice a week), YMU1 (15 mg/kg thrice a week); YMU (15 mg/kg thrice a week) combined with doxorubicin (1.25 mg/kg twice a week). Mice were administered with indicated treatment by intraperitoneal injection for 4 weeks, after which mice grew in drug-free condition for additional 2 weeks. The tumor size was measured every day after initiated drug treatment with an electronic caliper. The tumor volume was estimated using the formula: tumor volume=length (mm)×width$^2$ (mm$^2$)/2.

Cytotoxicity, Apoptosis Assay, and Cell Cycle Analysis

Cells plated into a 96-well plate ($10^3$ cells/well) were treated and cell viability was measured by MTS assay (Promega) (Cory et al., 1991). An annexin V-fluorescein isothiocyanate (FITC) apoptosis kit (Calbiochem) was used to detect apoptosis. The cell cycle analysis was performed by staining cells with propidium iodide (PI) for fluorescence-activated cell sorter (FACS) analysis with CellQuest software.

Immunohistochemistry

Monoclonal $K_i$ 67 antibody (B56) was purchased from BD PharMingen. Paraffin-embedded tumor sections (5 µm) were incubated with the primary antibody, detected with a LSAB™ kit (DakoCytomation) according to the manufacturer's instructions and counterstained with hematoxylin.

Colony Formation Assay

Cells were seeded to 100 mm-dish at 5,000 cells per dish. After 14 days, colonies were fixed and stained by crystal violet and counted.

Statistical Analyses

Two-tailed student's t-test was performed for quantifications of homologous recombination efficiency, percent (%) of cell with H2AX foci >10, Rad51 foci >20 or XRCC1 foci >5, qChIP analysis, tumor size and tumor weight; * indicates $p<0.05$, and ** indicates $p<0.01$. Data are presented as mean±s.d.

Any combination of the above-described elements in all possible variations thereof is encompassed by the invention unless otherwise indicated herein or otherwise clearly contradicted by context.

The terms "a" and "an" and "the" and similar referents as used in the context of de-scribing the invention are to be construed to cover both the singular and the plural, unless otherwise indicated herein or clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

REFERENCES

Agarwal, K. C., Miech, R. P., and Parks, R. E., Jr. (1978). Guanylate kinases from human erythrocytes, hog brain, and rat liver. Methods Enzymol 51, 483-490.

Ahmad, S. I., Kirk, S. H., and Eisenstark, A. (1998). Thymine metabolism and thymineless death in prokaryotes and eukaryotes. Annu Rev Microbiol 52, 591-625.

Arner, E. S., and Eriksson, S. (1995). Mammalian deoxyribonucleoside kinases. Pharmacol Ther 67, 155-186.

Berkovich, E., Monnat, R. J., Jr., and Kastan, M. B. (2007). Roles of ATM and NBS1 in chromatin structure modulation and DNA double-strand break repair. Nat Cell Biol 9, 683-690.

Bessman, M. J., Lehman, I. R., Adler, J., Zimmerman, S. B., Simms, E. S., and Kornberg, A. (1958). Enzymatic Synthesis of Deoxyribonucleic Acid. Iii. The Incorporation of Pyrimidine and Purine Analogues into Deoxyribonucleic Acid. Proc Natl Acad Sci USA 44, 633-640.

Bjorklund, S., Skogman, E., and Thelander, L. (1992). An S-phase specific release from a transcriptional block regulates the expression of mouse ribonucleotide reductase R2 subunit. EMBO J 11, 4953-4959.

Bolderson, E., Richard, D. J., Zhou, B. B., and Khanna, K. K. (2009). Recent advances in cancer therapy targeting proteins involved in DNA double-strand break repair. Clin Cancer Res 15, 6314-6320.

Bunz, F., Dutriaux, A., Lengauer, C., Waldman, T., Zhou, S., Brown, J. P., Sedivy, J. M., Kinzler, K. W., and Vogelstein, B. (1998). Requirement for p53 and p21 to sustain G2 arrest after DNA damage. Science 282, 1497-1501.

Burkhalter, M. D., Roberts, S. A., Havener, J. M., and Ramsden, D. A. (2009). Activity of ribonucleotide reductase helps determine how cells repair DNA double strand breaks. DNA Repair (Amst) 8, 1258-1263.

Chabes, A., and Stillman, B. (2007). Constitutively high dNTP concentration inhibits cell cycle progression and the DNA damage checkpoint in yeast *Saccharomyces cerevisiae*. Proc Natl Acad Sci USA 104, 1183-1188.

Chang, Z. F., Huang, D. Y., and Chi, L. M. (1998). Serine 13 is the site of mitotic phosphorylation of human thymidine kinase. J Biol Chem 273, 12095-12100.

Chang, Z. F., Huang, D. Y., and Hsue, N. C. (1994). Differential phosphorylation of human thymidine kinase in proliferating and M phase-arrested human cells. J Biol Chem 269, 21249-21254.

Cory, A. H., Owen, T. C., Barltrop, J. A., and Cory, J. G. (1991). Use of an aqueous soluble tetrazolium/formazan assay for cell growth assays in culture. Cancer Commun 3, 207-212.

Engstrom, Y., Eriksson, S., Jildevik, I., Skog, S., Thelander, L., and Tribukait, B. (1985). Cell cycle-dependent expression of mammalian ribonucleotide reductase. Differential regulation of the two subunits. J Biol Chem 260, 9114-9116.

Fan, H., Villegas, C., Huang, A., and Wright, J. A. (1998). The mammalian ribonucleotide reductase R2 component cooperates with a variety of oncogenes in mechanisms of cellular transformation. Cancer Res 58, 1650-1653.

Ferraro, P., Franzolin, E., Pontarin, G., Reichard, P., and Bianchi, V. (2010). Quantitation of cellular deoxynucleoside triphosphates. Nucleic Acids Res 38, e85.

Garg, D., Henrich, S., Salo-Ahen, O. M., Myllykallio, H., Costi, M. P., and Wade, R. C. (2010). Novel approaches for targeting thymidylate synthase to overcome the resistance and toxicity of anticancer drugs. J Med Chem 53, 6539-6549.

Hakansson, P., Hofer, A., and Thelander, L. (2006). Regulation of mammalian ribonucleotide reduction and dNTP pools after DNA damage and in resting cells. J Biol Chem 281, 7834-7841.

Harris, J. M., McIntosh, E. M., and Muscat, G. E. (1999). Structure/function analysis of a dUTPase: catalytic mechanism of a potential chemotherapeutic target. J Mol Biol 288, 275-287.

Helleday, T., Petermann, E., Lundin, C., Hodgson, B., and Sharma, R. A. (2008). DNA repair pathways as targets for cancer therapy. Nat Rev Cancer 8, 193-204.

Holthausen, J. T., Wyman, C., and Kanaar, R. (2010). Regulation of DNA strand exchange in homologous recombination. DNA Repair (Amst) 9, 1264-1272.

Hu, C. M., and Chang, Z. F. (2008). Synthetic lethality by lentiviral short hairpin RNA silencing of thymidylate kinase and doxorubicin in colon cancer cells regardless of the p53 status. Cancer Res 68, 2831-2840.

Hu, C. M., and Chang, Z. F. (2010). A bioluminescent method for measuring thymidylate kinase activity suitable for high-throughput screening of inhibitor. Anal Biochem 398, 269-271.

Huang, S. H., Tang, A., Drisco, B., Zhang, S. Q., Seeger, R., Li, C., and Jong, A. (1994). Human dTMP kinase: gene expression and enzymatic activity coinciding with cell cycle progression and cell growth. DNA Cell Biol 13, 461-471.

Jackson, S. P., and Bartek, J. (2009). The DNA-damage response in human biology and disease. Nature 461, 1071-1078.

Jensen, R. A., Page, D. L., and Holt, J. T. (1994). Identification of genes expressed in premalignant breast disease by microscopy-directed cloning. Proc Natl Acad Sci USA 91, 9257-9261.

Jiang, H., Reinhardt, H. C., Bartkova, J., Tommiska, J., Blomqvist, C., Nevanlinna, H., Bartek, J., Yaffe, M. B., and Hemann, M. T. (2009). The combined status of ATM and p53 link tumor development with therapeutic response. Genes Dev 23, 1895-1909.

Kastan, M. B., and Bartek, J. (2004). Cell-cycle checkpoints and cancer. Nature 432, 316-323.

Ke, P. Y., Kuo, Y. Y., Hu, C. M., and Chang, Z. F. (2005). Control of dTTP pool size by anaphase promoting complex/cyclosome is essential for the maintenance of genetic stability. Genes Dev 19, 1920-1933.

Krokan, H. E., Drablos, F., and Slupphaug, G. (2002). Uracil in DNA—occurrence, consequences and repair. Oncogene 21, 8935-8948.

Ladner, R. D., and Caradonna, S. J. (1997). The human dUTPase gene encodes both nuclear and mitochondrial isoforms. Differential expression of the isoforms and characterization of a cDNA encoding the mitochondrial species. J Biol Chem 272, 19072-19080.

Liu, X., Lai, L., Wang, X., Xue, L., Leora, S., Wu, J., Hu, S., Zhang, K., Kuo, M. L., Zhou, L., et al. (2011). Ribonucleotide reductase small subunit M2B prognoses better survival in colorectal cancer. Cancer Res 71, 3202-3213.

Longley, D. B., Harkin, D. P., and Johnston, P. G. (2003). 5-fluorouracil: mechanisms of action and clinical strategies. Nat Rev Cancer 3, 330-338.

Mah, L. J., El-Osta, A., and Karagiannis, T. C. (2010). gammaH2AX: a sensitive molecular marker of DNA damage and repair. Leukemia 24, 679-686.

Mathews, C. K. (2006). DNA precursor metabolism and genomic stability. Faseb J 20, 1300-1314.

Mimeault, M., Hauke, R., and Batra, S. K. (2008). Recent advances on the molecular mechanisms involved in the drug resistance of cancer cells and novel targeting therapies. Clin Pharmacol Ther 83, 673-691.

Miyata, S., Oshima, K., Kakizawa, S., Nishigawa, H., Jung, H. Y., Kuboyama, T., Ugaki, M., and Namba, S. (2003). Two different thymidylate kinase gene homologues, including one that has catalytic activity, are encoded in the onion yellows phytoplasma genome. Microbiology 149, 2243-2250.

Mosbaugh, D. W. (1988). Purification and characterization of porcine liver DNA polymerase gamma: utilization of dUTP and dTTP during in vitro DNA synthesis. Nucleic Acids Res 16, 5645-5659.

Nazarkina, Z. K., Khodyreva, S. N., Marsin, S., Lavrik, O. I., and Radicella, J. P. (2007). XRCC1 interactions with base excision repair DNA intermediates. DNA Repair (Amst) 6, 254-264.

Niida, H., Katsuno, Y., Sengoku, M., Shimada, M., Yukawa, M., Ikura, M., Ikura, T., Kohno, K., Shima, H., Suzuki, H., et al. (2010a). Essential role of Tip60-dependent recruitment of ribonucleotide reductase at DNA damage sites in DNA repair during G1 phase. Genes Dev 24, 333-338.

Niida, H., Shimada, M., Murakami, H., and Nakanishi, M. (2010b). Mechanisms of dNTP supply that play an essential role in maintaining genome integrity in eukaryotic cells. Cancer Sci 101, 2505-2509.

Nilsen, H., Otterlei, M., Haug, T., Solum, K., Nagelhus, T. A., Skorpen, F., and Krokan, H. E. (1997). Nuclear and mitochondrial uracil-DNA glycosylases are generated by alternative splicing and transcription from different positions in the UNG gene. Nucleic Acids Res 25, 750-755.

Nitiss, J. L. (2009). Targeting DNA topoisomerase II in cancer chemotherapy. Nat Rev Cancer 9, 338-350.

Nordlund, P., and Reichard, P. (2006). Ribonucleotide reductases. Annu Rev Biochem 75, 681-706.

Okumura, H., Natsugoe, S., Matsumoto, M., Mataki, Y., Takatori, H., Ishigami, S., Takao, S., and Aikou, T. (2005). The predictive value of p53, p53R2, and p21 for the effect of chemoradiation therapy on oesophageal squamous cell carcinoma. Br J Cancer 92, 284-289.

Ostermann, N., Schlichting, I., Brundiers, R., Konrad, M., Reinstein, J., Veit, T., Goody, R. S., and Lavie, A. (2000). Insights into the phosphoryltransfer mechanism of human thymidylate kinase gained from crystal structures of enzyme complexes along the reaction coordinate. Structure 8, 629-642.

Ostermann, N., Segura-Pena, D., Meier, C., Veit, T., Monnerjahn, C., Konrad, M., and Lavie, A. (2003). Structures of human thymidylate kinase in complex with prodrugs: implications for the structure-based design of novel compounds. Biochemistry 42, 2568-2577.

Pierce, A. J., Johnson, R. D., Thompson, L. H., and Jasin, M. (1999). XRCC3 promotes homology-directed repair of DNA damage in mammalian cells. Genes Dev 13, 2633-2638.

Pontarin, G., Ferraro, P., Rampazzo, C., Kollberg, G., Holme, E., Reichard, P., and Bianchi, V. (2011). Deoxyribonucleotide metabolism in cycling and resting human fibroblasts with a missense mutation in p53R2, a subunit of ribonucleotide reductase. J Biol Chem 286, 11132-11140.

Qiu, W., Zhou, B., Darwish, D., Shao, J., and Yen, Y. (2006). Characterization of enzymatic properties of human ribonucleotide reductase holoenzyme reconstituted in vitro from hRRM1, hRRM2, and p53R2 subunits. Biochem Biophys Res Commun 340, 428-434.

Reichard, P. (1988). Interactions between deoxyribonucleotide and DNA synthesis. Annu Rev Biochem 57, 349-374.

Robert, T., Vanoli, F., Chiolo, I., Shubassi, G., Bernstein, K. A., Rothstein, R., Botrugno, O. A., Parazzoli, D., Oldani, A., Minucci, S., and Foiani, M. (2011). HDACs link the DNA damage response, processing of double-strand breaks and autophagy. Nature 471, 74-79.

San Filippo, J., Sung, P., and Klein, H. (2008). Mechanism of eukaryotic homologous recombination. Annu Rev Biochem 77, 229-257.

Shao, J., Zhou, B., Zhu, L., Qiu, W., Yuan, Y. C., Xi, B., and Yen, Y. (2004). In vitro characterization of enzymatic properties and inhibition of the p53R2 subunit of human ribonucleotide reductase. Cancer Res 64, 1-6.

Traut, T. W. (1994). Physiological concentrations of purines and pyrimidines. Mol Cell Biochem 140, 1-22.

Xu, X., Page, J. L., Surtees, J. A., Liu, H., Lagedrost, S., Lu, Y., Bronson, R., Alani, E., Nikitin, A. Y., and Weiss, R. S. (2008). Broad overexpression of ribonucleotide reductase genes in mice specifically induces lung neoplasms. Cancer Res 68, 2652-2660.

Yanamoto, S., Kawasaki, G., Yoshitomi, I., and Mizuno, A. (2003). Expression of p53R2, newly p53 target in oral normal epithelium, epithelial dysplasia and squamous cell carcinoma. Cancer Lett 190, 233-243.

Yang, T. C., Georgy, K. A., Tavakoli, A., Craise, L. M., and Durante, M. (1996). Radiogenic transformation of human mammary epithelial cells in vitro. Radiat Oncol Investig 3, 412-419.

Zhang, K., Hu, S., Wu, J., Chen, L., Lu, J., Wang, X., Liu, X., Zhou, B., and Yen, Y. (2009). Overexpression of RRM2 decreases thrombspondin-1 and increases VEGF production in human cancer cells in vitro and in vivo: implication of RRM2 in angiogenesis. Mol Cancer 8, 11.

What is claimed:

1. A composition for inhibiting thymidylate kinase (TMPK) comprising a therapeutically effective amount of:

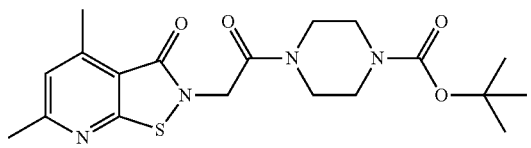

or a pharmaceutically acceptable salt, hydrate or solvate thereof.

2. A pharmaceutical composition comprising a composition of claim 1 and a pharmaceutically acceptable carrier.

3. A method for manufacturing a composition of claim 1 comprising the steps of:

treating pyridinothiazolone 4 with appropriate halides in the presence of $Et_3N$ and $Cs_2CO_3$ to give compound 22

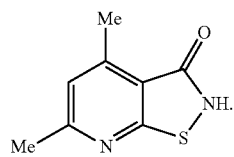

* * * * *